(12) United States Patent
Anfossi et al.

(10) Patent No.: US 9,181,341 B2
(45) Date of Patent: Nov. 10, 2015

(54) ANTI-KIR3D ANTIBODIES

(75) Inventors: Nicolas Anfossi, Francheville (FR); Laurent Gauthier, Marseilles (FR); Yannis Morel, Marseilles (FR); Alessandro Moretta, Genoa (IT); Silvia Parolini, Brescia (IT); Benjamin Rossi, Marseilles (FR)

(73) Assignee: INNATE PHARMA, Marseilles (FR)

( * ) Notice: Subject to any disclaimer, the term of this patent is extended or adjusted under 35 U.S.C. 154(b) by 632 days.

(21) Appl. No.: 13/145,224

(22) PCT Filed: Jan. 15, 2010

(86) PCT No.: PCT/EP2010/050480
§ 371 (c)(1),
(2), (4) Date: Nov. 22, 2011

(87) PCT Pub. No.: WO2010/081890
PCT Pub. Date: Jul. 22, 2010

(65) Prior Publication Data
US 2012/0064081 A1 Mar. 15, 2012

Related U.S. Application Data

(60) Provisional application No. 61/145,635, filed on Jan. 19, 2009.

(51) Int. Cl.
| | | |
|---|---|---|
| A61K 39/00 | (2006.01) | |
| A61K 39/395 | (2006.01) | |
| C07K 16/00 | (2006.01) | |
| C12P 21/08 | (2006.01) | |
| G01N 33/00 | (2006.01) | |
| G01N 33/53 | (2006.01) | |
| G01N 33/567 | (2006.01) | |
| G01N 33/574 | (2006.01) | |
| C07K 16/28 | (2006.01) | |
| C07K 16/30 | (2006.01) | |

(52) U.S. Cl.
CPC ......... *C07K 16/2803* (2013.01); *C07K 16/3061* (2013.01); *A61K 2039/505* (2013.01); *C07K 2317/24* (2013.01); *C07K 2317/41* (2013.01); *C07K 2317/56* (2013.01); *C07K 2317/565* (2013.01); *C07K 2317/73* (2013.01); *C07K 2317/732* (2013.01)

(58) Field of Classification Search
None
See application file for complete search history.

(56) References Cited

U.S. PATENT DOCUMENTS

2011/0256121 A1* 10/2011 Richardson ................ 424/130.1

FOREIGN PATENT DOCUMENTS

WO    WO 02/050122    *  6/2002  ............. C07K 16/28

OTHER PUBLICATIONS

Romagne et al. 'Preclinical characterization of 1-7F9, a novel human anti-KIR receptor therapeutic antibody that augments natural killer-mediated killing of tumor cells.' Blood 114:2667-2677, 2009.*
Ortonne, N. et al. "Significance of circulating T-cell clones in Sézary syndrome" *Blood*, May 15, 2006, pp. 4030-4038, vol. 107, No. 10.
Bouaziz, J. et al. "Circulating Natural Killer Lymphocytes Are Potential Cytotoxic Effectors Against Autologous Malignant Cells in Sezary Syndrome Patients" *The Journal of Investigative Dermatology*, Dec. 2005, pp. 1273-1278, vol. 125, No. 6.
Ruggeri, L. et al. "Donor natural killer cell allorecognition of missing self in haploidentical hematopoietic transplantation for acute myeloid leukemia: challenging its predictive value" *Blood*, Jan. 1, 2007, pp. 433-440, vol. 110, No. 1.
Parolini, S. et al. "The AZ158 mAb specifically reacts with p70 and p140 inhibitory NK receptors for HLA-B and HLA-A alleles" In: *Leucocyte Typing VII, White Cell Differentiation Antigens*, Jan. 1, 2002, pp. 415-417.
Romagnani, C. et al. "CD56$^{bright}$CD16$^-$Killer Ig-Like Receptor$^-$ NK Cells Display Longer Telomeres and Acquire Features of CD56$^{dim}$ NK Cells upon Activation$^1$" *The Journal of Immunology*, Apr. 15, 2007, pp. 4947-4955, vol. 178, No. 8.
Brando, C. et al. "Receptors and lytic mediators regulating antitumor activity by the leukemic killer T cell line TALL-104" *Journal of Leukocyte Biology*, Aug. 2005, pp. 359-371, vol. 78, No. 2.
Pende, D. et al. "The Natural Killer Cell Receptor Specific for HLA-A Allotypes: A Novel Member of the p58/p70 Family of Inhibitory Receptors That Is Characterized by Three Immunoglobulin-like Domains and Is Expressed as a 140-kD Disulphide-linked Dimer" *The Journal of Experimental Medicine*, Aug. 1, 1996, pp. 505-518, vol. 184, No. 2.

* cited by examiner

*Primary Examiner* — Nora Rooney
(74) *Attorney, Agent, or Firm* — Saliwanchik, Lloyd & Eisenschenk

(57) ABSTRACT

The present invention provides antigen-binding proteins capable of binding to KIR3D polypeptides. The antibodies have increased activity in the treatment of disorders characterized by KIR3DL2-expressing cells, particularly CD4+ T cells, including malignancies such as Mycosis Fungoides and Sézary Syndrome.

11 Claims, 16 Drawing Sheets

US 9,181,341 B2

SEQUENCE LISTING

```
<160> NUMBER OF SEQ ID NOS: 31

<210> SEQ ID NO 1
<211> LENGTH: 1857
<212> TYPE: DNA
<213> ORGANISM: homo sapiens
```

<400> SEQUENCE: 1

```
tgtctgcacc ggcagcacca tgtcgctcat ggtcgtcagc atggcgtgtg ttgggttgtt      60
cttggtccag agggccggtc cacacatggg tggtcaggac aaaccccttcc tgtctgcctg    120
gcccagcgct gtggtgcctc gaggaggaca cgtgactctt cggtgtcact atcgtcatag    180
gtttaacaat ttcatgctat acaaagaaga cagaatccac attcccatct ccatggcag     240
aatattccag agagcttca acatgagccc tgtgaccaca gcacatgcag ggaactacac      300
atgtcggggt tcacacccac actcccccac tgggtggtcg gcacccagca accccgtggt    360
gatcatggtc acaggaaacc acagaaaacc ttccctcctg gcccacccag gtcccctggt    420
gaaatcagga gagagagtca tcctgcaatg ttggtcagat atcatgtttg agcacttctt    480
tctgcacaaa gaggggatct ctaaggaccc ctcacgcctc gttggacaga tccatgatgg    540
ggtctccaag gccaatttct ccatcggtcc catgatgctt gcccttgcag ggacctacag    600
atgctacggt tctgttactc acaccccta tcagttgtca gctcccagtg atccctgga     660
catcgtggtc acaggtccat atgagaaacc ttctctctca gcccagccgg gccccaaggt    720
tcaggcagga gagagcgtga ccttgtcctg tagctcccgg agctcctatg acatgtacca    780
tctatccagg gagggggag cccatgaacg taggctccct gcagtgcgca aggtcaacag     840
aacattccag gcagatttcc ctctgggccc tgccacccac ggagggacct acagatgctt    900
cggctctttc cgtcactctc cctacgagtg gtcagacccg agtgacccac tgcttgtttc    960
tgtcacagga aacccttcaa gtagttggcc ttcacccaca gaaccaagct ccaaatctgg   1020
taacccccaga cacctgcaca ttctgattgg gacctcagtg gtcatcatcc tcttcatcct  1080
cctcctcttc tttctccttc atctctggtg ctccaacaaa aaaaatgctg ctgtaatgga   1140
ccaagagcct gcagggaaca gaacagccaa cagcgaggac tctgatgaac aagaccctga   1200
ggaggtgaca tacgcacagt ggatcactg cgttttcaca cagagaaaaa tcactcgccc   1260
ttctcagagg cccaagacac cccctacaga taccatcttg tacacggaac ttccaaatgc   1320
taagcccaga tccaaagttg tctcctgccc atgagcacca cagtcaggcc ttgaggacgt   1380
cttctaggga gacaacagcc ctgtctcaaa accgagttgc cagctcccat gtaccagcag   1440
ctggaatctg aaggcgtgag tcttcatctt agggcatcgc tcctcctcac gccacaaatc   1500
tggtgcctct ctcttgctta caaatgtcta ggtccccact gctgctgga agaaaaacac    1560
actcctttgc ttagcccaca gttctccatt tcacttgacc cctgcccacc tctccaacct   1620
aactggctta cttcctagtc tacttgaggc tgcaatcaca ctgaggaact cacaattcca   1680
aacatacaag aggctccctc ttgacgtggc acttacccac gtgctgttcc accttccctc   1740
atgctgtttc acctttcttc ggactatttt ccagccttct gtcagcagtg aaacttataa   1800
aatttttgt gatttcaatg tagctgtctc ctcttcaaat aaacatgtct gccctca      1857
```

<210> SEQ ID NO 2
<211> LENGTH: 444
<212> TYPE: PRT
<213> ORGANISM: homo sapiens

<400> SEQUENCE: 2

```
Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30
```

-continued

```
Ala Trp Pro Ser Ala Val Val Pro Arg Gly Gly His Val Thr Leu Arg
         35                  40                  45

Cys His Tyr Arg His Arg Phe Asn Asn Phe Met Leu Tyr Lys Glu Asp
 50                  55                  60

Arg Ile His Ile Pro Ile Phe His Gly Arg Ile Phe Gln Glu Ser Phe
 65                  70                  75                  80

Asn Met Ser Pro Val Thr Thr Ala His Ala Gly Asn Tyr Thr Cys Arg
                 85                  90                  95

Gly Ser His Pro His Ser Pro Thr Gly Trp Ser Ala Pro Ser Asn Pro
                100                 105                 110

Val Val Ile Met Val Thr Gly Asn His Arg Lys Pro Ser Leu Leu Ala
                115                 120                 125

His Pro Gly Pro Leu Val Lys Ser Gly Glu Arg Val Ile Leu Gln Cys
        130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
                180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255

Arg Glu Gly Gly Ala His Glu Arg Arg Leu Pro Ala Val Arg Lys Val
                260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
                325                 330                 335

Arg His Leu His Ile Leu Ile Gly Thr Ser Val Val Ile Ile Leu Phe
        340                 345                 350

Ile Leu Leu Leu Phe Phe Leu Leu His Leu Trp Cys Ser Asn Lys Lys
    355                 360                 365

Asn Ala Ala Val Met Asp Gln Glu Pro Ala Gly Asn Arg Thr Ala Asn
370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
                405                 410                 415

Arg Pro Lys Thr Pro Pro Thr Asp Thr Ile Leu Tyr Thr Glu Leu Pro
        420                 425                 430

Asn Ala Lys Pro Arg Ser Lys Val Val Ser Cys Pro
    435                 440
```

<210> SEQ ID NO 3
<211> LENGTH: 1863
<212> TYPE: DNA
<213> ORGANISM: homo sapiens

<400> SEQUENCE: 3

| | | | | | |
|---|---|---|---|---|---|
| tgtctgcacc | ggcagcacca | tgtcgctcac | ggtcgtcagc | atggcgtgcg | ttgggttctt | 60 |
| cttgctgcag | ggggcctggc | cactcatggg | tggtcaggac | aaacccttcc | tgtctgcccg | 120 |
| gcccagcact | gtggtgcctc | gaggaggaca | cgtggctctt | cagtgtcact | atcgtcgtgg | 180 |
| gtttaacaat | ttcatgctgt | acaaagaaga | cagaagccac | gttcccatct | ccacggcag | 240 |
| aatattccag | agagcttca | tcatgggccc | tgtgacccca | gcacatgcag | ggacctacag | 300 |
| atgtcggggt | tcacgcccac | actccctcac | tgggtggtcg | gcacccagca | accccctggt | 360 |
| gatcatggtc | acaggaaacc | acagaaaacc | ttccctcctg | cccacccag | ggcccctgct | 420 |
| gaaatcagga | gagacagtca | tcctgcaatg | ttggtcagat | gtcatgtttg | agcacttctt | 480 |
| tctgcacaga | gagggatct | ctgaggaccc | ctcacgcctc | gttggacaga | tccatgatgg | 540 |
| ggtctccaag | gccaacttct | ccatcggtcc | cttgatgcct | gtccttgcag | gaacctacag | 600 |
| atgttatggt | tctgttcctc | actcccccta | tcagttgtca | gctcccagtg | accccctgga | 660 |
| catcgtgatc | acaggtctat | atgagaaaacc | ttctctctca | gcccagccgg | gccccacggt | 720 |
| tcaggcagga | gagaacgtga | ccttgtcctg | tagctcctgg | agctcctatg | acatctacca | 780 |
| tctgtccagg | gaaggggagg | cccatgaacg | taggctccgt | gcagtgccca | aggtcaacag | 840 |
| aacattccag | gcagactttc | ctctgggccc | tgccacccac | ggagggacct | acagatgctt | 900 |
| cggctctttc | cgtgccctgc | cctgcgtgtg | gtcaaactca | agtgacccac | tgcttgtttc | 960 |
| tgtcacagga | aacccttcaa | gtagttggcc | ttcacccaca | gaaccaagct | ccaaatctgg | 1020 |
| tatctgcaga | cacctgcatg | ttctgattgg | gacctcagtg | gtcatcttcc | tcttcatcct | 1080 |
| cctcctcttc | tttctccttt | atcgctggtg | ctccaacaaa | aagaatgctg | ctgtaatgga | 1140 |
| ccaagagcct | gcgggggaca | gaacagtgaa | taggcaggac | tctgatgaac | aagaccctca | 1200 |
| ggaggtgacg | tacgcacagt | tggatcactg | cgttttcata | cagagaaaaa | tcagtcgccc | 1260 |
| ttctcagagg | cccaagacac | ccctaacaga | taccagcgtg | tacacggaac | ttccaaatgc | 1320 |
| tgagcccaga | tccaaagttg | tctcctgccc | acgagcacca | cagtcaggtc | ttgaggggt | 1380 |
| tttctaggga | gacaacagcc | ctgtctcaaa | accaggttgc | cagatccaat | gaaccagcag | 1440 |
| ctggaatctg | aaggcatcag | tctgcatctt | aggggatcgc | tcttcctcac | accacgaatc | 1500 |
| tgaacatgcc | tctctcttgc | ttacaaatgc | ctaaggtcgc | cactgcctgc | tgcagagaaa | 1560 |
| acacactcct | ttgcttagcc | cacaagtatc | tatttcactt | gacccctgcc | cacctctcca | 1620 |
| acctaactgg | cttacttcct | agtcctactt | gaggctgcaa | tcacactgag | gaactcacaa | 1680 |
| ttccaaacat | acaagaggct | ccctcttaac | acggcactta | cacacttgct | gttccacctt | 1740 |
| ccctcatgct | gttccacctc | ccctcagact | atctttcagc | cttctgtcat | cagtaaaatt | 1800 |
| tataaatttt | ttttataact | tcagtgtagc | tctctcctct | tcaaataaac | atgtctgccc | 1860 |
| tca | | | | | | 1863 |

<210> SEQ ID NO 4
<211> LENGTH: 455
<212> TYPE: PRT
<213> ORGANISM: homo sapiens

```
<400> SEQUENCE: 4

Met Ser Leu Thr Val Val Ser Met Ala Cys Val Gly Phe Phe Leu Leu
1               5                  10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
    370                 375                 380

Arg Gln Asp Ser Asp Glu Gln Asp Pro Gln Glu Val Thr Tyr Ala Gln
385                 390                 395                 400
```

```
Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 5
<211> LENGTH: 1740
<212> TYPE: DNA
<213> ORGANISM: homo sapiens

<400> SEQUENCE: 5
ccggcagcac catgtcgctc atggtcgtca gcatggcgtg tgttgggttg ttcttggtcc      60
agagggccgg tccacacatg ggtggtcagg acaagccctt cctgtctgcc tggcccagcg     120
ctgtggtgcc tcgcggagga cacgtgactc ttcggtgtca ctatcgtcat aggtttaaca     180
atttcatgct atacaaagaa gacagaatcc acgttcccat cttccatggc agaatattcc     240
aggagggctt caacatgagc cctgtgacca cagcacatgc agggaactac acatgtcggg     300
gttcacaccc acactccccc actgggtggt cggcacccag caaccccatg gtgatcatgg     360
tcacaggaaa ccacagaaaa ccttccctcc tggcccaccc aggtccctg gtgaaatcag      420 gagagagagt catcctgcaa tgttggtcag atatcatgtt tgagcacttc tttctgcaca     480
aagagtggat ctctaaggac ccctcacgcc tcgttggaca gatccatgat ggggtctcca     540
aggccaattt ctccatcggt tccatgatgc gtgcccttgc agggacctac agatgctacg     600
gttctgttac tcacaccccc tatcagttgt cagctcccag tgatccctg gacatcgtgg      660 tcacaggtct atatgagaaa ccttctctct cagcccagcc gggccccaag gttcaggcag     720
gagagagcgt gaccttgtcc tgtagctccc ggagctccta tgacatgtac catctatcca     780
ggaggggggg agcccatgaa cgtaggctcc ctgcagtgcg caaggtcaac agaacattcc     840
aggcagattt ccctctgggc cctgccaccc acggagggac ctacagatgc ttcggctctt     900
tccgtcactc tccctacgag tggtcagacc cgagtgaccc actgcttgtt tctgtcacag     960
gaaacccttc aagtagttgg ccttcaccca cagaaccaag ctccaaatct ggtaacctca    1020
gacacctgca cattctgatt gggacctcag tggtcaaaat cccctttcacc atcctcctct   1080 tctttctcct tcatcgctgg tgctccaaca aaaaaaatgc tgctgtaatg gaccaagagc    1140
ctgcagggaa cagaagtgaa cagcgaggat tctgatgaac aagaccatca ggaggtgaca    1200
tacgcataat tggaacactg tgttttcaca cagagaaaaa tcactcgccc ttctcagagg    1260
cccaagacac ccccaacaga taccagcatg tacatagaac ttccaaatgc tgagcccaga    1320
tccaaagttg tcttctgtcc acgagcacca cagtcaggcc ttgagggat cttctaggga     1380 gacaacagcc ctgtctcaaa actgggttgc cagttcccat gtaccagcag ctggaatctg    1440
aaggcatcag tcttcatctt agggcatcgc tcttcctcac accacaaatc tgaatgtgcc    1500
tctcacttgc ttacaaatgt ctaaggtccc cactgcctgc tggagaaaaa acacactcct    1560
ttgcttagcc cacagttctc catttcactt gaccctgcc cacctctcca acctaactgg     1620
cttacttcct agtctacttg aggctgcaat cacactgagg aactcacaat tccacacata    1680
caagaggctc cgtcttaacg cagcacttag acacgtgctg ttccaccttc cctcatgctg    1740
```

<210> SEQ ID NO 6
<211> LENGTH: 387
<212> TYPE: PRT
<213> ORGANISM: homo sapiens

<400> SEQUENCE: 6

Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
        35                  40                  45

Cys His Tyr Arg His Arg Phe Asn Asn Phe Met Leu Tyr Lys Glu Asp
    50                  55                  60

Arg Ile His Val Pro Ile Phe His Gly Arg Ile Phe Gln Glu Gly Phe
65                  70                  75                  80

Asn Met Ser Pro Val Thr Thr Ala His Ala Gly Asn Tyr Thr Cys Arg
                85                  90                  95

Gly Ser His Pro His Ser Pro Thr Gly Trp Ser Ala Pro Ser Asn Pro
            100                 105                 110

Met Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
    130                 135                 140

Trp Ser Asp Ile Met Phe Glu His Phe Phe Leu His Lys Glu Trp Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Ser Met Met Arg Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Leu Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Leu
                325                 330                 335

Arg His Leu His Ile Leu Ile Gly Thr Ser Val Val Lys Ile Pro Phe
            340                 345                 350

Thr Ile Leu Leu Phe Phe Leu Leu His Arg Trp Cys Ser Asn Lys Lys
        355                 360                 365

Asn Ala Ala Val Met Asp Gln Glu Pro Ala Gly Asn Arg Ser Glu Gln
    370                 375                 380

```
Arg Gly Phe
385

<210> SEQ ID NO 7
<211> LENGTH: 369
<212> TYPE: DNA
<213> ORGANISM: Mus musculus

<400> SEQUENCE: 7
caggtgcagc tgaaggagtc aggacctggc ctggtggcgc cctcacagag cctgtccatc      60
acttgcactg tctctgggtt ttcattaacc agctttggtg tacactgggt tcgccagcct     120
ccaggaaagg gtctggagtg gctgggagta atatgggctg gtggaagcac aaattataat     180
tcggctctca tgtccagact gagcatcagc aaagacaact ccaagagcca agttttctta     240
aaaatgaaca gtctgcaaaa tgatgacaca gccatgtact actgtgccag aggaaattcg     300
aatcactacg ttagtagctt ctactacttt gactactggg gccaaggcac cactctcaca     360
gtctcctca                                                             369

<210> SEQ ID NO 8
<211> LENGTH: 123
<212> TYPE: PRT
<213> ORGANISM: Mus musculus

<400> SEQUENCE: 8

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Phe
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Asn Asp Asp Thr Ala Met Tyr Tyr Cys Ala
                85                  90                  95

Arg Gly Asn Ser Asn His Tyr Val Ser Ser Phe Tyr Tyr Phe Asp Tyr
            100                 105                 110

Trp Gly Gln Gly Thr Thr Leu Thr Val Ser Ser
        115                 120

<210> SEQ ID NO 9
<211> LENGTH: 318
<212> TYPE: DNA
<213> ORGANISM: Mus musculus

<400> SEQUENCE: 9
gacatccaga tgacacagtc tccatcctca ctgtctgcat ctctgggagg caaagtcacc      60
atcacttgca aggcaagcca agacattaac aagtatatag cttggtacca acacaagcct     120
ggaaaaggtc ctaggctgct catacattac acatctacat tacagccagg catcccatca     180
aggttcagtg aagtgggtc tgggagagat tattccttca gcatcagcaa cctggagcct     240
gaagatatta caacttatta ttgtctacag tatgataatc tgtggacgtt cggtggaggc     300
accaagctgg aaatcaaa                                                   318
```

```
<210> SEQ ID NO 10
<211> LENGTH: 106
<212> TYPE: PRT
<213> ORGANISM: Mus musculus

<400> SEQUENCE: 10

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Thr Thr Tyr Tyr Cys Leu Gln Tyr Asp Asn Leu Trp Thr
                85                  90                  95

Phe Gly Gly Gly Thr Lys Leu Glu Ile Lys
            100                 105

<210> SEQ ID NO 11
<211> LENGTH: 10
<212> TYPE: PRT
<213> ORGANISM: Mus musculus

<400> SEQUENCE: 11

Gly Phe Ser Leu Thr Ser Phe Gly Val His
1               5                   10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 15
<212> TYPE: PRT
<213> ORGANISM: Mus musculus

<400> SEQUENCE: 13

Gly Asn Ser Asn His Tyr Val Ser Ser Phe Tyr Tyr Phe Asp Tyr
1               5                   10                  15

<210> SEQ ID NO 14
<211> LENGTH: 11
<212> TYPE: PRT
<213> ORGANISM: Mus musculus

<400> SEQUENCE: 14

Lys Ala Ser Gln Asp Ile Asn Lys Tyr Ile Ala
1               5                   10

<210> SEQ ID NO 15
<211> LENGTH: 7
<212> TYPE: PRT
<213> ORGANISM: Mus musculus
```

<400> SEQUENCE: 15

Tyr Thr Ser Thr Leu Gln Pro
1               5

<210> SEQ ID NO 16
<211> LENGTH: 8
<212> TYPE: PRT
<213> ORGANISM: Mus musculus

<400> SEQUENCE: 16

Leu Gln Tyr Asp Asn Leu Trp Thr
1               5

<210> SEQ ID NO 17
<211> LENGTH: 1419
<212> TYPE: DNA
<213> ORGANISM: Mus musculus

<400> SEQUENCE: 17

```
atggctgtcc tggtgctgtt cctctgcctg gttgcatttc caagctgtgt cctgtcccag      60
gtgcagctga aggagtcagg acctggcctg gtggcgccct cacagagcct gtccatcact     120
tgcactgtct ctgggttttc attaaccagc tttggtgtac actgggttcg ccagcctcca     180
ggaaagggtc tggagtggct gggagtaata tgggctggtg aagcacaaa ttataattcg      240
gctctcatgt ccagactgag catcagcaaa gacaactcca gagccaagt tttcttaaaa     300
atgaacagtc tgcaaaatga tgacacagcc atgtactact gtgccagagg aaattcgaat     360
cactacgtta gtagcttcta ctactttgac tactggggcc aaggcaccac tctcacagtc     420
tcctcagcta gcaccaaggg cccatcggtc ttccccctgg caccctcctc caagagcacc     480
tctgggggca gcggccct gggctgcctg gtcaaggact acttccccga accggtgacg      540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccca aaacccaagg acaccctcat gatctcccgg      840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaataa                           1419
```

<210> SEQ ID NO 18
<211> LENGTH: 472
<212> TYPE: PRT
<213> ORGANISM: Mus musculus

```
<400> SEQUENCE: 18

Met Ala Val Leu Val Leu Phe Leu Cys Leu Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
            35                  40                  45

Thr Ser Phe Gly Val His Trp Val Arg Gln Pro Pro Gly Lys Gly Leu
    50                  55                  60

Glu Trp Leu Gly Val Ile Trp Ala Gly Gly Ser Thr Asn Tyr Asn Ser
65              70                  75                  80

Ala Leu Met Ser Arg Leu Ser Ile Ser Lys Asp Asn Ser Lys Ser Gln
                85                  90                  95

Val Phe Leu Lys Met Asn Ser Leu Gln Asn Asp Asp Thr Ala Met Tyr
            100                 105                 110

Tyr Cys Ala Arg Gly Asn Ser Asn His Tyr Val Ser Ser Phe Tyr Tyr
            115                 120                 125

Phe Asp Tyr Trp Gly Gln Gly Thr Thr Leu Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415
```

```
Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 19
<211> LENGTH: 702
<212> TYPE: DNA
<213> ORGANISM: Mus musculus

<400> SEQUENCE: 19
atgagaccgt ctattcagtt cctggggctc ttgttgttct ggcttcatgg tgctcagtgt    60
gacatccaga tgacacagtc tccatcctca ctgtctgcat ctctgggagg caaagtcacc   120
atcacttgca aggcaagcca agacattaac aagtatatag cttggtacca acacaagcct   180
ggaaaaggtc ctaggctgct catacattac acatctacat tacagccagg catcccatca   240
aggttcagtg gaagtgggtc tgggagagat tattccttca gcatcagcaa cctggagcct   300
gaagatatta caacttatta ttgtctacag tatgataatc tgtggacgtt cggtggaggc   360
accaagctgg aaatcaaacg tacggtggct gcaccatctg tcttcatctt cccgccatct   420
gatgagcagt tgaaatctgg aactgcctct gttgtgtgcc tgctgaataa cttctatccc   480
agagaggcca agtacagtgg aaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agttcgcccg tcacaaagag cttcaacagg ggagagtgtt aa                      702

<210> SEQ ID NO 20
<211> LENGTH: 233
<212> TYPE: PRT
<213> ORGANISM: Mus musculus

<400> SEQUENCE: 20

Met Arg Pro Ser Ile Gln Phe Leu Gly Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Thr Thr Tyr Tyr Cys Leu Gln Tyr Asp
            100                 105                 110

Asn Leu Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140
```

-continued

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

```
<210> SEQ ID NO 21
<211> LENGTH: 117
<212> TYPE: PRT
<213> ORGANISM: homo sapiens

<400> SEQUENCE: 21

Pro Leu Met Gly Gly Gln Asp Lys Pro Phe Leu Ser Ala Arg Pro Ser
1               5                   10                  15

Thr Val Val Pro Arg Gly His Val Ala Leu Gln Cys His Tyr Arg
                20                  25                  30

Arg Gly Phe Asn Asn Phe Met Leu Tyr Lys Glu Asp Arg Ser His Val
            35                  40                  45

Pro Ile Phe His Gly Arg Ile Phe Gln Glu Ser Phe Ile Met Gly Pro
        50                  55                  60

Val Thr Pro Ala His Ala Gly Thr Tyr Arg Cys Arg Gly Ser Arg Pro
65                  70                  75                  80

His Ser Leu Thr Gly Trp Ser Ala Pro Ser Asn Pro Leu Val Ile Met
                85                  90                  95

Val Thr Gly Asn His Arg Lys Pro Ser Leu Leu Ala His Pro Gly Pro
            100                 105                 110

Leu Leu Lys Ser Gly
        115
```

```
<210> SEQ ID NO 22
<211> LENGTH: 100
<212> TYPE: PRT
<213> ORGANISM: homo sapiens

<400> SEQUENCE: 22

Thr Val Ile Leu Gln Cys Trp Ser Asp Val Met Phe Glu His Phe Phe
1               5                   10                  15

Leu His Arg Glu Gly Ile Ser Glu Asp Pro Ser Arg Leu Val Gly Gln
                20                  25                  30

Ile His Asp Gly Val Ser Lys Ala Asn Phe Ser Ile Gly Pro Leu Met
            35                  40                  45

Pro Val Leu Ala Gly Thr Tyr Arg Cys Tyr Gly Ser Val Pro His Ser
        50                  55                  60

Pro Tyr Gln Leu Ser Ala Pro Ser Asp Pro Leu Asp Ile Val Ile Thr
65                  70                  75                  80

Gly Leu Tyr Glu Lys Pro Ser Leu Ser Ala Gln Pro Gly Pro Thr Val
                85                  90                  95

Gln Ala Gly Glu
            100
```

```
<210> SEQ ID NO 23
<211> LENGTH: 102
<212> TYPE: PRT
<213> ORGANISM: Homo sapiens

<400> SEQUENCE: 23

Asn Val Thr Leu Ser Cys Ser Ser Trp Ser Ser Tyr Asp Ile Tyr His
1               5                   10                  15

Leu Ser Arg Glu Gly Glu Ala His Glu Arg Arg Leu Arg Ala Val Pro
            20                  25                  30

Lys Val Asn Arg Thr Phe Gln Ala Asp Phe Pro Leu Gly Pro Ala Thr
        35                  40                  45

His Gly Gly Thr Tyr Arg Cys Phe Gly Ser Phe Arg Ala Leu Pro Cys
    50                  55                  60

Val Trp Ser Asn Ser Ser Asp Pro Leu Leu Val Ser Val Thr Gly Asn
65                  70                  75                  80

Pro Ser Ser Ser Trp Pro Ser Pro Thr Glu Pro Ser Ser Lys Ser Gly
                85                  90                  95

Ile Cys Arg His Leu His
            100

<210> SEQ ID NO 24
<211> LENGTH: 72
<212> TYPE: DNA
<213> ORGANISM: Artificial
<220> FEATURE:
<223> OTHER INFORMATION: PCR primer

<400> SEQUENCE: 24
aagctagcgg taagcctatc cctaaccctc tcctcggtct cgattctacg ctcatgggtg      60
gtcaggacaa ac                                                          72

<210> SEQ ID NO 25
<211> LENGTH: 29
<212> TYPE: DNA
<213> ORGANISM: Artificial
<220> FEATURE:
<223> OTHER INFORMATION: PCR primer

<400> SEQUENCE: 25
aaggatccct ctcctgattt cagcagggt                                        29

<210> SEQ ID NO 26
<211> LENGTH: 71
<212> TYPE: DNA
<213> ORGANISM: Artificial
<220> FEATURE:
<223> OTHER INFORMATION: PCR primer

<400> SEQUENCE: 26
aagctagcgg taagcctatc cctaaccctc tcctcggtct cgattctacg acagtcatcc      60
tgcaatgttg g                                                           71

<210> SEQ ID NO 27
<211> LENGTH: 29
<212> TYPE: DNA
<213> ORGANISM: Artificial
<220> FEATURE:
<223> OTHER INFORMATION: PCR primer

<400> SEQUENCE: 27
aaggatccct ctcctgcctg aaccgtggg                                        29
```

```
<210> SEQ ID NO 28
<211> LENGTH: 71
<212> TYPE: DNA
<213> ORGANISM: Artificial
<220> FEATURE:
<223> OTHER INFORMATION: PCR primer

<400> SEQUENCE: 28
aagctagcgg taagcctatc cctaaccctc tcctcggtct cgattctacg aacgtgacct      60
tgtcctgtag c                                                          71

<210> SEQ ID NO 29
<211> LENGTH: 29
<212> TYPE: DNA
<213> ORGANISM: Artificial
<220> FEATURE:
<223> OTHER INFORMATION: PCR primer

<400> SEQUENCE: 29
aaggatccat gcaggtgtct gcagatacc                                       29

<210> SEQ ID NO 30
<211> LENGTH: 90
<212> TYPE: DNA
<213> ORGANISM: Artificial
<220> FEATURE:
<223> OTHER INFORMATION: CD24-GPI anchor

<400> SEQUENCE: 30
actaatgcca ccaccaaggc ggctggtggt gccctgcagt caacagccag tctcttcgtg      60
gtctcactct ctcttctgca tctctactct                                      90

<210> SEQ ID NO 31
<211> LENGTH: 30
<212> TYPE: PRT
<213> ORGANISM: Artificial
<220> FEATURE:
<223> OTHER INFORMATION: CD24-GPI Anchor

<400> SEQUENCE: 31

Thr Asn Ala Thr Thr Lys Ala Ala Gly Gly Ala Leu Gln Ser Thr Ala
1               5                   10                  15

Ser Leu Phe Val Val Ser Leu Ser Leu Leu His Leu Tyr Ser
            20                  25                  30
```

ANTI-KIR3D ANTIBODIES

CROSS-REFERENCE TO RELATED APPLICATION

This application is the U.S. national stage application of International Patent Application No. PCT/EP2010/050480, filed Jan. 15, 2010, which claims the benefit of U.S. Provisional Patent Application No. 61/145,635, filed Jan. 19, 2009, the disclosures of which are hereby incorporated by reference in their entireties, including all figures, tables and amino acid or nucleic acid sequences.

FIELD OF THE INVENTION

The present invention provides antigen-binding proteins capable of binding to KIR3DL2 polypeptides. The antibodies have increased activity in the treatment of disorders characterized by KIR3DL-expressing cells, particularly CD4+ T cells, including malignancies such as Mycosis Fungoides and Sézary Syndrome.

BACKGROUND

Killer immunoglobulin-like receptors (KIR) are a family of receptors that, along with C-type lectin receptors (CD94-NKG2), are used by human NK cells and T-lymphocyte subsets to specifically recognize MHC class I molecules. Certain inhibitory and activating KIR have highly similar extracellular domains and are recognised by the same monoclonal antibody, e.g. KIR2DL1 and KIR2DS1 are both recognised by EB6, and 2DL2 and 2DS2 by GL183. Three criteria (number of extracellular Ig-like domains (domains D0, D1, D2), cytoplasmic tail length, and sequence analogy) have been used to categorise the KIR proteins into 13 groups, namely KIR3DL1-2, KIR3DS1, KIR2DL1-5, and KIR2DS1-5. The nomenclature 2D for 2 domains or 3D for 3 domains give the number of Ig-like domains; receptors with either long or short cytoplasmic domains are further classified as L or S. (Pascal V. et al., 2007 J. Immunol. 179:1625-1633) The inhibitory receptors possess long (L) cytoplasmic tails (i.e., KIR2DL or KIR3DL) containing a canonical ITIM that becomes tyrosine phosphorylated upon KIR engagement of their HLA class I ligands. The phosphorylated ITIM recruits the Src homology 2 domain containing protein tyrosine phosphatases Src homology 2 domain-containing phosphatase 1 and/or Src homology 2 domain-containing phosphatase 2, which dephosphorylate cellular substrates, thus aborting the NK activation signal, i.e., sparing target cells with appropriate self-MHC class I expression. Receptors with short (S) cytoplasmic tails lack ITIMs (i.e., KIR2DS or KIR3DS). These activating KIR contain a charged residue within their transmembrane domain facilitating interaction with the signaling chain KARAP/DAP12. Engagement of the KIR2DS family of receptors has been shown to lead to a cascade of KARAP/DAP12-mediated signaling events culminating in increased NK cell cytolytic activity and the production of proinflammatory cytokines such as IFN-γ (Pascal et al. 2007) J. Immunol. 179: 1625-1633). Mature NK cells are predicted to acquire at least one inhibitory receptor specific for a self-MHC class I molecule, which generally functionally prevails over potentially auto-reactive activating molecules. It is proposed that the response of NK cells represents the integrated outcome of both activating and inhibitory signalling by KIR and other receptors.

X-ray crystallographic analysis has provided high-resolution images of KIR2DL2 bound to HLA-Cw3 and of KIR2DL1 bound to HLA-Cw4 (Boyington, et al. (2000) Nature. 405:537-543). In both complexes loops from the Ig-like domains D1 and D2 of KIR2D are involved in binding to HLA molecules. In comparison to the interactions of KIR2D with HLA-C, little is known of the interaction between KIR3D and their ligands HLA-B or HLA-A. The KIR2D genes encoding HLA-C receptors form part of a larger group of KIR called lineage III KIR and all KIR2D genes of lineage III contain a pseudoexon encoding a D0 domain that is not incorporated into mature RNA. KIR2D genes are thus believed to have evolved from KIR3D genes. Human KIR specific for HLA-A and B form part of KIR lineage II which is comprised solely of KIR3D which all comprise a D0 domain. The D0 domain is the most N-terminal Ig-like domain in KIR3D proteins. While some reports suggest that the D0 domain is not involved in ligand-induced signalling (e.g., Snyder et al. (1999) Proc. Natl. Acad. Sci. USA. 96:3864-3869, others have proposed models where D0 domain does not participate in ligand binding it may have an enhancing role in signaling. Khakoo et al., (2002) (J. Exp. Med. 196(7):911-921) reported that various point mutations in the D1 and D2 domains of KIR3DL1, but none of 15 different point mutations in D0, abrogated KIR3DL1 binding to Bw4+ HLA-B.

It has been reported that several malignancies, autoimmune or inflammatory disorders involve CD4+ T cells that express KIR3D receptors. However, the functional role of KIR in T cells is largely unknown, and KIR-mediated signalling has been reported only in CD8+ T and NK cells, in which case KIR have been involved in regulating effector cell cytotoxicity. The little knowledge of KIR signalling in CD4+ T cells has been limited to activatory KIR (e.g. KIRDS polypeptides), and these have been reported only to have a co-activatory role, rather than the true activatory role in NK cells (see e.g. Namekawa 2000, supra). The lack of true activatory function for KIRDS was reported to be due to missing "DAP12" signalling adaptors in T cells (Snyder et al. (2003) J. Exp. Med. 197(4):437-49).

The existence of numerous anti-KIR antibodies has been reported in the scientific literature. Shin et al (1999) Hybridoma 18(6): 521-527 for example report a study of KIR antibodies. The majority of the antibodies that bound the KIR did not appear to inhibit the signal transduction mediated by the KIR and were therefore non-functional. Watzl C. et al., (2000) Tissue Antigens; 56: 240-247, identified "Lig1" antibodies that bind a common epitope on KIR2D receptors, (except for KIR2DL4) but did not bind any KIR3D polypeptides. However, the Watzl et al. antibodies were not functional in their ability to block KIR-ligand mediated inhibition of NK cell cytotoxicity, nor did they inhibit binding of KIR-Ig fusion proteins to MHC class I-expressing cells. Other publications cite the existence of antibodies reactive against various KIR3D polypeptides. None of these antibodies are reported to distinguish KIR3D polypeptides from KIR2D polypeptides by binding all KIR3D (i.e. KIR3DL1, KIR3DL2 and KIR3DS1) yet no KIR2D polypeptides. Two anti-KIR3DL2 antibodies have been reported: Q241 and Q66 (Pende, et al. (1996) J Exp Med 184:505-518). These two antibodies are of the IgM isotype and will be expected to have low ADCC activity, or if their variable regions were placed in the context of a bivalent IgG type antibody, their affinity would generally decrease to the extent that significant ADCC induction would be precluded. The existence of a further KIR3DL2 antibody referred to only by the name of the "AZ158" cells producing it was reported (Parolini, S., et al. (2002) In Leucocyte typing VII. D. Mason, editor. Oxford University Press, Oxford. 415-417). Several antibodies have been reported to bind the monomeric KIR3DL1 but not dimeric p140-KIR3DL2 (e.g. clone Z27 from the A. Moretta group and DX9 from the L. Lanier group, both available from Becton Dickinson). While KIR3DL1 and KIR3DS1 share high sequence identity (KIR3DS1 is an activating form of the KIRDL1 gene), KIR3DL2 and KIR3DL1 differ in that KIR3DL2 are dimeric and share lower amino acid identity with KIR3DL1, including within the ECD (86% identity). KIR3DL1 recognize the MHC class I molecules HLA-B while KIR3DL2 recognize HLA-A.

Despite great deal of research into the KIR family, and despite the existence of research reagents binding to various KIR, the role of certain KIR such as KIR3D polypeptides remained to be elucidated. There therefore remained a need for improving anti-KIR based therapies.

SUMMARY OF THE INVENTION

The present invention results, inter alia, from the discovery of antibodies that bind the D0 domain of KIR3D polypeptides. The D0 domain is located at amino acid residues 22 to 145, with reference to the KIR3DL2 polypeptide of SEQ ID NO 4. It was furthermore observed that the antibody having such functionality bound not only KIR3DL2, but also KIR3DL1 and KIR3DS1, and that the antibody bound a common determinant in domain D0 of these KIR3D proteins. The invention further results from the discovery that antibodies that bind KIR3DL2 polypeptides, and in particular the D0 domain of KIR3D polypeptides, are able to directly slow the proliferation of KIR3DL2-expressing CD4+ T cells, i.e. by inducing a KIR3DL2-mediated inhibitory signal. Previously only the D1 and D2 domains have been reported to be essential in signaling induced by binding of HLA molecule ligands to KIR3DL polypeptides. Additionally, it is shown that it is possible to obtain antibodies that are selective for the D0 domain over the D1 and D2 Ig-like domains, providing a means to specifically target, identify and modulate the activity of the D0 domain of KIR3D polypeptides. It was furthermore discovered that the anti-KIR3D antibodies having Fc portions that bind Fc receptors were capable of mediating NK cell mediated ADCC toward KIR3DL2-expressing cells, independently of or in addition to any KIR3DL2-signalling effect. It was also observed that the antibodies' ability to mediate ADCC toward KIR3DL2-expressing cells could be significantly improved by modification of the Fc portion of the antibody by producing it in a cell line which generates hypofucosylated antibodies.

The present invention further provides antigen-binding compounds, e.g. antibodies, that bind a common determinant or epitope shared by the KIR3DL2 in dimeric or monomeric form, as well as the monomeric KIR3DL1 and KIR3DS1. The antigen-binding compounds thereby provide a means to distinguish the KIR3D polypeptides from the KIR2D polypeptides. As shown in the Examples herein, an antibody that binds all KIR3D but not KIR2D polypeptides recognized slightly more than about half of NK cells from an individual donor. An antibody that recognizes all KIR (or at least KIR2DL1 and KIR2DL2/3) on the other hand will bind each NK cell, as observed in polyclonal NK populations from different donors (Watzl et al. 2000, supra), since every NK cell in every donor is believed to express a KIR2D receptor. Additionally, expression of KIR3D receptors on NK cells, particularly KIR3DS1, is believed to be at a relatively low level, which may, without wishing to be bound by theory, have precluded significant ADCC-mediated depletion of NK cells by an IgG1 antibody. As a result, the KIR3D-specific antigen-binding compounds have a degree of selectivity for its cellular targets and can deplete KIR-expressing T cells via NK-cell mediated ADCC. Moreover, NK cell-mediated ADCC activity can be augmented to high levels by modifying the Fc region of the antibody.

In another embodiment, encompassed is an isolated antigen-binding compound, e.g. an antibody, that specifically binds an epitope present on a KIR3DL2 polypeptide and inhibits proliferation of KIR3DL2-expressing cells, e.g. human T lymphocytes, tumor cells, T lymphocyte tumor cells. In one embodiment, the invention provides an isolated antigen-binding compound that specifically binds an epitope present on a KIR3DL (e.g. KIR3DL1 or KIR3DL2) polypeptide and induces KIR3 DL (e.g. KIR3DL1 or KIR3DL2) signaling on a KIR3DL-expressing cell, e.g. a T lymphocyte. Such compounds can be used to inhibit the proliferation or activity (e.g. proinflammatory activity, cytokine production) of tumor cells or cells involved in autoimmunity or inflammation, e.g. T cells.

In another aspect, the invention provides an isolated antigen-binding compound that specifically binds an epitope present on a KIR3DL (e.g. KIR3DL1 or KIR3DL2) polypeptide and induces KIR3DL (e.g. KIR3DL1 or KIR3DL2) signaling in a KIR3DL-expressing cell, wherein the compound does not substantially induce ADCC of a KIR3D-expressing target cell. Examples of such a compound includes antibodies that do not comprise an Fc region that has substantial binding to Fc receptors such as CD16, e.g. antibodies comprising an Fc region that has low or no binding to Fc receptors such as IgG4 isotypes or IgG isotypes modified to decrease binding to Fc receptors. Such compounds can be used to inhibit the proliferation of activity (e.g. proinflammatory activity, cytokine production) of cells involved in autoimmunity or inflammation, e.g. T cells, without killing the cells.

In one embodiment, the invention provides an antigen-binding compound that binds an Ig-like domain 0 of SEQ ID NO 21. Optionally said antigen-binding compound binds domain 0 of SEQ ID NO 21 selectively compared to KIR3DL2 domain 1 of SEQ ID NO 22 or KIR3DL2 domain 2 of SEQ ID NO 23. Preferably, the binding compound binds domain 0 of SEQ ID NO 21 with a binding affinity that is at least 1-log, 2-log, 3-log or 4-log greater (optionally a dissociation constant (KD) of at 1-log, 2-log, 3-log or 4-log less) than its binding to a KIR3DL2 domain 1 of SEQ ID NO 22 or KIR3DL2 domain 2 of SEQ ID NO 23. Optionally, said compound does not substantially bind Ig-like domain 1 of SEQ ID NO 22 and/or Ig-like domain 2 of SEQ ID NO 23. In one aspect, any of the antigen-binding compounds of the invention binds a common determinant present on KIR3DL1 and KIR3DL2, preferably a common determinant present in domain D0 of KIR3D receptors. Optionally, in any of the embodiments, the antigen-binding compound induces signaling by a KIR3DL polypeptide. In one aspect, any of the antigen-binding compounds of the invention binds a common determinant present on KIR3DL2 and KIR3DS1. Optionally, said antigen-binding compound binds a common determinant present on KIR3DL1, KIR3DL2 and KIR3DS1. Optionally said KIR3DL2 is a monomer or a homodimer, e.g. present on the surface of a cell such as an NK cell, T cell, a cell transfected with DNA encoding KIR3DL2 polypeptides. Preferably said KIR3D polypeptide(s) is a human polypeptide.

Significantly, in certain embodiments, since antigen-binding compounds that bind a KIR3DL2 polypeptide, particularly in the case when antibodies are used, will not depend exclusively on immune cell mediated cell killing (e.g. ADCC), it is expected that antigen-binding compounds that bind a KIR3DL2 polypeptide can be used effectively in patients having a deficient or suppressed immune system, and/or in combination with additional anti-tumor agents, anti-inflammatory agents, particularly therapeutic agents which are known to have adverse impacts on the immune system. For example, immunocompromised patients (e.g., with HIV infection), patients taking anti-inflammatory or immunosuppressive drugs (e.g., subsequent to transplantation or as treatment for autoimmune disorders, agents for the treatment of an autoimmune or inflammatory conditions), or patients taking chemotherapeutic agents are particularly good candidates for treatment with such compounds.

Additionally, since antigen-binding compounds of the invention that bind a KIR3DL2 polypeptide and have an ADCC or anti-proliferative effect can eradicate or stop the growth of proliferating cells, it may be desirable to combine the antigen-binding compounds disclosed herein with other anti-proliferative and/or ADCC agents in the in vitro and in vivo methods provided herein, such that the respective ADCC or anti-cell proliferation activities are enhanced, and also so that the cells can be, e.g., first subjected to growth arrest and then eradicated by the ADCC compounds.

In a preferred embodiment, the antigen-binding compound of any of the embodiments herein is "naked" and is not functionalized with a radioactive isotope, toxic peptide or toxic small molecule (e.g. a "naked" antibody). In another embodiment, the antigen-binding compound is a cytotoxic antigen-binding compound and comprises an element selected from the group consisting of radioactive isotope, toxic peptide, and toxic small molecule. In another embodiment, the radioactive isotope, toxic peptide, or toxic small molecule is directly attached to the antigen-binding compound.

Preferably the antigen-binding compound binds to the same epitope on a KIR3DL polypeptide (e.g. KIR3DL2) as antibody chAZ158. In one embodiment, the antigen-binding compound competes for binding with antibody chAZ158 to a KIR3DL2 polypeptide (e.g. to an isolated polypeptide or to a cell expressing it). Optionally, the antigen-binding compound further competes for binding with antibody chAZ158 to a KIR3DL1 and/or KIR3DS1 polypeptide.

In any of the embodiments herein, the antigen binding compound specifically binds to malignant human CD4+ T cells. In any of the embodiments herein, the antigen binding compound causes the elimination of malignant human KIR3DL2-expressing CD4+ T cells. In any of the embodiments herein, the antigen binding compound inhibits the proliferation of malignant human KIR3DL2-expressing CD4+ T cells. Optionally the CD4+ T cells are from individuals having Sezary Syndrome or Mycosis Fungoides, or from individuals having an autoimmune or inflammatory condition.

In another embodiment, the antigen-binding compound of any of the embodiments herein is an antibody, e.g., a bivalent chimeric or humanized antibody. In one such embodiment, the antibody comprises the variable (antigen-binding) domains of antibody chAZ158, e.g. the variable regions or part of all of the CDRs of chAZ158.

In another embodiment of any of the embodiments herein, the antibodies are not substantially internalized by KIR3DL2-expressing cells, e.g., Cou-L cells, and as such are capable of inducing cell mediated killing (ADCC) of target (KIR3DL2-expressing) cells.

In one aspect of any of the embodiments herein, the antibody comprises an Fc tail, optionally an Fc tail that is hypofucosylated. In one embodiment the invention provides an antibody composition comprising a plurality of antibodies according to any of the embodiments herein, wherein at least 40% of antibodies have a common N-linked oligosaccharide structure of a biantennary-type that comprises long chains with terminal GlcNac that are highly galactosylated and non-fucosylated.

In one aspect of any of the embodiments herein, the anti-KIR3DL2 antibodies have a binding affinity to KIR3DL2-epitopes, preferably the epitope specifically recognized by chAZ158, on e.g. KIR3DL2, of 50, 40, 30, 20, 10, 5, 1, or less nanomolar. In other preferred embodiments, the antibody is an antibody other than murine AZ158, Q66 or Q241, each of which are antibodies having murine Fc regions, or having non-human Fc regions.

Accordingly, the present invention provides a method of treating a patient with a T cell lymphoma, e.g. CTCL, SS, MF), the method comprising administering to the patient a pharmaceutically effective amount of an antigen-binding compound according to the invention that specifically binds to a KIR3DL2 polypeptide.

In another embodiment, the present invention provides a method of treating a patient with an autoimmune or pro-inflammatory disorder mediated at least in part by KIR3D-expressing T cells, the method comprising administering to the patient a pharmaceutically effective amount of an antigen-binding compound according to the invention that specifically binds to a KIR3D polypeptide.

The present invention also provides a method of treating a patient, the method comprising:
a) determining whether the patient has pathogenic KIR3DL-expressing cells, optionally KIR3DL-expressing CD4+ T cells, and
b) if the patient is determined to patient have pathogenic KIR3DL-expressing cells, administering an antigen-binding compound (e.g., antibody) of the invention that specifically binds a KIR3DL (e.g. KIR3DL2) polypeptide and that is capable of inducing ADCC and/or inhibiting the activity, growth or proliferation of a KIR3DL-expressing cell. Preferably, the antigen-binding compound activates KIR3DL (e.g. KIR3DL2).

In one embodiment, the invention provides a method of producing an antigen-binding compound, said method comprising: i) providing an antigen-binding compound that specifically binds to a KIR3D polypeptide, optionally by immunizing a non-human animal with a KIR polypeptide or by producing a library of antigen-binding compounds, ii) testing the ability of the antigen-binding compound for binding to an epitope within domain 0 of a KIR3D polypeptide and to an epitope within domain 1 and/or 2 of a KIR3D polypeptide; iii) selecting the antigen-binding compound if it is determined that the antigen-binding compound binds to an epitope within domain 0 of a KIR3D polypeptide but not within domains 1 and/or 2 of a KIR3D polypeptide; and optionally iv) testing the ability to the antigen-binding compound to modulate an activity of the KIR3D polypeptide and selecting the antigen-binding compound if it is determined that the antigen-binding compound modulates an activity of the KIR3D polypeptide. The method may optionally further comprise a step of producing a quantity of the selected antigen-binding compound.

In one embodiment, the invention provides a method of producing an antigen-binding compound suitable for use in the treatment of disorders characterized by pathogenic KIR3DL-expressing cells, said method comprising: i) providing an antigen-binding compound that specifically binds to a KIR3DL2 polypeptide, ii) testing the ability of the antigen-binding compound for ADCC (e.g. in a cytotoxicity assay) and/or activate KIR3DL (e.g. in a cell proliferation assay, signal transduction assay); iii) selecting the antigen-binding compound if it is determined that the antigen-binding compound has ADCC and/or activate KIR3DL; and optionally iv)

producing a quantity of the selected antigen-binding compound. In one embodiment, the compound selected in step iii) is an antibody and is made suitable for human administration prior to step iv), for example by humanizing or chimerizing it. Optionally, a plurality of antigen-binding compounds are provided in step i), and they are each tested in step ii) for their ability to induce ADCC and/or activate KIR3DL or inhibit the proliferation of a cell expressing a KIR3DL polypeptide. Typically, step ii) will involve standard assays in which cells, e.g. KIR3DL-expressing cells, will be contacted with the compound and the proliferation, survival and/or activity (KIR signal transduction, proliferation) of the cells will be assessed. When testing ADCC, step ii) may involve standard assays where ability of the antibody to induce NK cell mediated cytotoxicity, markers of NK cell activation, of the KIR3DL-expressing cells is tested. The cells may be for example T lymphoma cells such as Cou-L cells, cells taken from a patient with a T cell malignancy or a T cell mediated autoimmune or inflammatory disorder, e.g. CD4+CD28− T cells. In preferred embodiments, the antigen-binding compound is an antibody, optionally the antibody is an IgG. Additionally, the antibody is preferably bivalent. Preferably the antibody selected induces at least 30, 40 or 50% lysis of KIR3DL-expressing target cells in a cytoxocity assay. In preferred embodiments, the antibody is IgG. Additionally, the antibody is preferably bivalent (and comprises an Fc tail). In other preferred embodiments, the antibody is hypofucosylated.

In another embodiment, the invention provides a method of producing an antigen-binding compound suitable for use in the treatment of a disorder characterized by pathogenic KIR3DL-expressing cells, said method comprising: i) producing a quantity of an antigen-binding compound that specifically binds to a KIR3DL2 polypeptide, ii) testing a sample from said quantity of antigen-binding compound for ADCC and/or activate KIR3DL (e.g. in a cell proliferation assay, signal transduction assay); iii) selecting the quantity for use as a medicament and/or in the manufacture of a medicament if it is determined that the antigen-binding compound has ADCC and/or KIR3DL signaling activity; and optionally iv) preparing the quantity for administration to a human, optionally formulating a quantity of the selected antigen-binding compound with a pharmaceutically acceptable carrier.

In another embodiment, the invention provides a method of producing an antigen-binding compound, comprising: i) providing an antigen-binding compound that specifically binds to cells expressing a KIR3DL (e.g. KIR3DL2) polypeptide taken from one or more patients with a disorder characterized by pathogenic KIR3DL-expressing cells; ii) testing the antigen-binding compound for ADCC and/or activation of KIR3DL (e.g. KIR3DL2) in cells taken from one or more patients with a disorder characterized by a pathogenic expansion of KIR3DL-expressing cells, e.g. T cell lymphoma, SS or MF, an inflammatory or autoimmune disorder; iii) if the antigen-binding compound induces ADCC towards or activates KIR3DL in a substantial number of KIR3DL-expressing cells taken from one or more of the patients, making the antigen-binding compound suitable for human administration; and iv) optionally producing a quantity of the human-suitable antigen-binding compound.

In one embodiment of any of the methods of the invention, the method may comprise a step of immunizing a non-human mammal (e.g. a mouse, rat, rabbit, mouse transgenic for human Ig genes, etc.) with a KIR3DL polypeptide (e.g. a purified polypeptide or a cell expressing the polypeptide) prior to step i). In another embodiment, the method comprises a step of generating a library of antigen-binding compound (e.g. via phage display methods and the like) and selecting an antigen-binding compound that binds KIR3DL polypeptide prior to step i).

In one embodiment of any of the methods of the invention, the antigen-binding compound or antibody of step i) and/or step ii) does not comprise a cytotoxic agent such as a radioactive isotope, a toxic polypeptide, or a toxic small molecule.

Testing the ability of each of the antigen-binding compound or antibodies to induce ADCC of a cell or to activate KIR3DL2 in a cell (e.g. inhibit the cell's proliferation) can be carried out according to any of a variety of available methods. For example, testing ADCC may comprise without limitation detecting death (e.g. lysis, cytokine production, mobilization of cytoxicity markers) of a target cell (e.g. malignant cell, Cou-L cell, cell expressing a KIR3DL2 polypeptide) or increases and/or decreases in cytokines or generally proteins involved in ADCC. Testing for activation of KIR3DL2 may comprise without limitation detecting cell growth inhibition or phosphorylation of signal transduction components such as SHP-1. For example, any of the assays in the Examples section herein can be used. Optionally, testing activation of KIR3DL2 is carried out in the absence of immune effector cells, particularly NK cells.

In one embodiment of any of the methods of the invention, making the antigen-binding compound suitable for administration to a human comprises making an anti-KIR3D antibody chimeric, human, or humanized. Making the compound suitable for administration to a human can also comprise formulating the compound with a pharmaceutically acceptable carrier.

In one embodiment of any of the methods of the invention, producing a quantity of antigen-binding compound comprises culturing a cell expressing the antigen-binding compound in a suitable medium and recovering the antigen-binding compound. Optionally, the cell is a recombinant host cell made to express the antigen-binding compound. In one embodiment, the compound is a monoclonal antibody and the cell is a hybridoma.

In one embodiment of any of the methods of the invention, the antigen-binding compound, particularly the antigen-binding compound produced by the method does not comprise a cytotoxic agent such as a radioactive isotope, a toxic polypeptide, or a toxic small molecule. In one embodiment, the antigen-binding compound is an antibody that specifically binds a KIR3D polypeptide. In one embodiment of any of the methods of the invention, the antigen-binding compound competes for binding with antibody chAZ158 to a KIR3D polypeptide. In one embodiment of any of the methods of the invention, the compound is an antibody other than AZ158. In another embodiment of any of the methods of the invention the compound is a chimeric, human, or humanized antibody.

In one embodiment of any of the methods of the invention, the antigen-binding compound, preferably an antibody, has an Fc receptor binding portion, preferably a heavy chain constant region of an IgG isotype, optionally of a human IgG isotype. In a preferred embodiment, the antibody is an IgG1 antibody; such antibodies will be able to mediate ADCC and/or crosslink KIR3DL receptors so as to induce receptor signaling. The invention also encompasses fragments and derivatives of antibodies having substantially the same antigen specificity and activity (e.g., which can bind to the same antigens as the parent antibody). Such fragments include, without limitation, Fab fragments, Fab'2 fragments, CDR and ScFv. When the compound is an antibody, the antibody will typically be, for example, chimeric, humanized or human. In one preferred embodiment, the antibody is a recombinant chimeric antibody.

In certain embodiments, the compounds of the invention are multimeric (i.e. cross-linked) IgG antibodies. In preferred embodiments, the antibodies are tetrameric (two heavy and two light chains) and are thus bivalent. In particularly preferred embodiments, the antibodies are capable of inducing ADCC or activating KIR3DL (e.g. KIR3DL2). In other particularly preferred embodiments, the antibodies are capable of inducing KIR3DL signaling in cells expressing KIR3DL, and are also able to induce ADCC of cells expressing KIR3DL. In other preferred embodiments, the antibodies are capable of inducing at least 20%, 30, 40 or 50% cell lysis, in a cytoxicity assay, e.g. of cells from SS patients or SS cell lines (e.g., Cou-L cells).

In another embodiment, the invention encompasses an antigen-binding compound produced according to any of the methods of the invention.

The invention also encompasses pharmaceutical formulations comprising any of the antigen binding compounds and in particular any of the antibodies of the invention and a pharmaceutically acceptable carrier are also provided, as are kits. Kits may for example comprise the compound and instructions for its use and/or a carrier composition e.g., in the treatment of CTCL, autoimmune or inflammatory disorders. Kits may comprise the compound and a carrier; kits may comprise the compound in a manufactured (e.g. glass, plastic or other) container. Cells expressing the antibodies, e.g., hybridomas, are also encompassed.

In one embodiment, the antigen-binding compound or antibody of the invention competes for binding with antibody chAZ158 to a KIR3DL2 polypeptide. The invention also encompasses fragments and derivatives of the antibodies having substantially the same antigen specificity and activity as antibody chAZ158 (e.g., which can bind to the same antigens as the parent antibody). Such fragments include, without limitation, Fab fragments, Fab'2 fragments, CDR and ScFv.

Accordingly, in another embodiment, the invention provides an antibody, preferably an isolated antibody, which binds to a KIR3DL2 polypeptide and which is capable of inducing ADCC and/or activating KIR3DL2 in a cell which expresses a KIR3DL2 polypeptide, wherein the antibody competes for binding with antibody chAZ158 to a KIR3DL2 polypeptide.

In another embodiment, the invention provides a bivalent antibody comprised of two heavy chains and two light chains, wherein the heavy chains comprise an IgG heavy chain constant region capable of binding to an Fc receptor, and wherein the antibody: (a) is capable of activating KIR3DL in cells (e.g. inhibiting the proliferation of the cells, receptor signaling) expressing a KIR3DL polypeptide; (b) is capable of inducing cell-mediated killing (ADCC) of KIR3DL-expressing cells; and (c) competes for binding with antibody chAZ158 to a KIR3DL polypeptide.

In another embodiment, the invention provides a bivalent antibody comprising: (a) a heavy chain comprising a variable region comprising one or more CDRs derived from the amino acid sequence of SEQ ID NO: 8 fused to a human IgG chain constant region; and (b) a light chain comprising a variable region comprising one or more CDRs derived from the amino acid sequence of SEQ ID NO: 10, optionally fused to human kappa chain constant region.

In another embodiment, any of the antibodies herein can further be characterized as having a heavy chain constant region of an IgG isotype, optionally of a human IgG or IgG1 isotype. In another embodiment, any of the antibodies herein can further be characterized by being tetrameric. In another embodiment, any of the antibodies herein can further be characterized as being bivalent. In another embodiment, any of the antibodies herein can further be characterized as being a chimeric, human or humanized antibody. In another embodiment, any of the antibodies herein can further be characterized as being hypofucosylated.

The invention also encompasses a cell expressing any of the antigen-binding compounds of the invention. In one aspect the cell is a hybridoma which produces an antibodies of the invention. In another aspect the cell is a recombinant host cell which produces an antibody of any one of the preceding claims. Optionally the host cell is an avian cell, preferably a chicken or duck cell, preferably further an avian embryonic derived stem cell line. Optionally the cell produces antibodies having hypofucosylated Fc regions. The invention also encompasses methods of producing an antibody comprising culturing a host cell and recovering the antibody produced by said host cells.

The invention also encompasses a pharmaceutical composition comprising any of the herein-described antigen-binding compounds or antibodies, and a pharmaceutically acceptable carrier. In another aspect, the invention encompasses a kit comprising an antigen-binding compound or an antibody of the invention, and instructions for using said antigen-binding compound or antibody in the treatment or diagnosis of a KIR3DL-expressing pathology. In another embodiment, cells, e.g., hybridomas, are also provided. In another aspect, the invention encompasses a method of treating an individual (e.g. a human) having a disorder characterized by KIR3D (e.g. KIR3DL2) expressing cells, particularly a T cell malignancy, a cardiovascular disorder, an autoimmune disorder or an inflammatory disorder, the method comprising administering to said individual an antigen binding compound, antibody or pharmaceutical composition of the invention.

In other aspects, provided is a method of inducing the ADCC and/or inhibiting the activity or proliferation of a pathogenic KIR3DL-expressing cell, and/or of treating a patient or individual with a disorder selected from the group consisting of a T cell malignancy, an autoimmune disorder and an inflammatory disorder, the method comprising: a) determining if a pathogenic KIR3DL-expressing cell is suitable for treatment with a ADCC and/or KIR3DL activating agent, and b) in the case of a positive determination that the pathogenic KIR3DL-expressing cell is suitable for treatment with a ADCC and/or KIR3DL activating agent, contacting the pathogenic KIR3DL-expressing cell with an effective amount of any of the antigen-binding compounds of the invention. In yet another aspect, the invention provides a method of inducing the ADCC and/or inhibiting the activity or proliferation of a pathogenic KIR3DL-expressing cell, and/or of treating a patient or individual with a disorder selected from the group consisting of a T cell malignancy, an autoimmune disorder and an inflammatory disorder, the method comprising: a) determining if pathogenic cells (e.g. CD4+ T cells, CD4+ T lymphoma cells, CD4+ cells involved in inflammation or autoimmunity) from the patient express a KIR3DL polypeptide, and b) in the case of a positive determination that pathogenic cells expresses a KIR3DL polypeptide, contacting pathogenic cells with an effective amount of an antigen-binding compound of any one of the above claims. Optionally, in these methods, the step of contacting the pathogenic cells comprises administering to the patient a pharmaceutically effective amount of an antigen-binding compound of the invention. Preferably, the pharmaceutically effective amount is an amount effective to induce ADCC or inhibit the activity or proliferation of pathogenic cell(s) in the patient. In certain embodiments, in assessment of inhibition of cell proliferation the contacting is carried out in the absence or relative paucity of immune effector cells, e.g., NK cells, for example when such methods are carried out in vitro or when they are carried out in patients with deficient immune systems (e.g., due to conditions such as AIDS, to conditions that decrease NK cell levels, to the administration of chemotherapeutic agents, or to the use of immunosuppressive agents, for example in conjunction with a transplantation procedure or treatment of autoimmune disorders).

In another aspect, the invention provides a method of inducing the ADCC of and/or inhibiting the activity or proliferation of a KIR3DL polypeptide-expressing cell, comprising bringing said cell into contact with an antigen-binding compound of the invention in an amount effective to induce ADCC and/or inhibit the activity or proliferation of the cell. Optionally, when inhibiting cell proliferation directly (i.e. inducing KIR signaling), said bringing into contact is in the absence or relative paucity of immune effector cells, e.g., NK cells, and/or is carried out in vitro. Optionally the method further comprises determining whether the antigen-binding compound is capable of inducing ADCC and/or inhibiting the proliferation of the cell. Optionally, the compound is an antibody that is capable of inducing the cell-mediated killing (ADCC) of KIR3DL-expressing cells, in the presence of immune effector (e.g., NK) cells.

These and additional advantageous aspects and features of the invention may be further described elsewhere herein.

DETAILED DESCRIPTION OF THE INVENTION

Introduction

Figure 1:
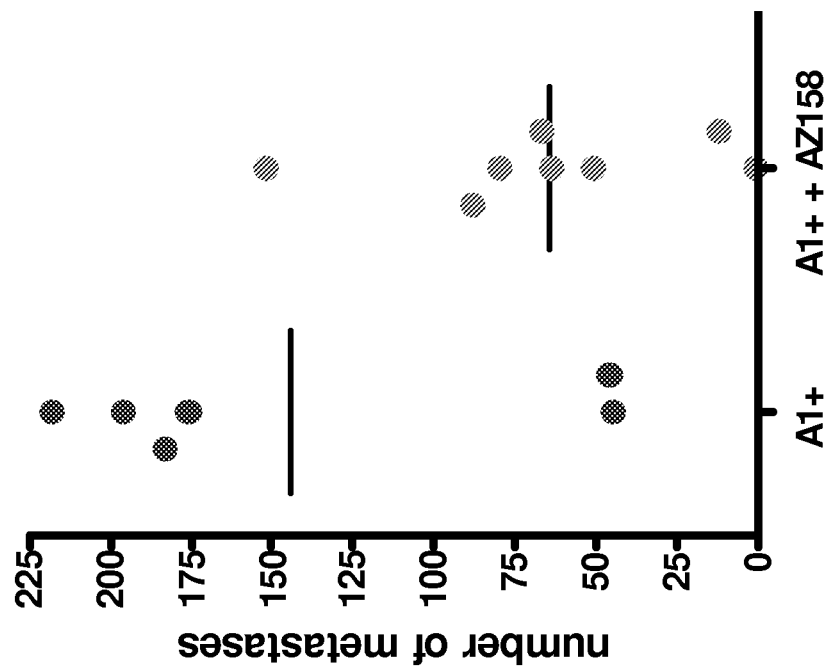
FIGS. 1 to 3 together show three series of treatment of C57B16 mice bearing B16 melanoma cells with AZ158 on days −1, 1, 5 and 7, as assessed by counting the number of lung metastases at day 20. Results in FIGS. 1 to 3 demonstrate that AZ158 decreased the number of metastases significantly compared to mice not receiving AZ158.

The present invention results, inter alia, from the discovery that antigen-binding compounds that bind KIR3DL2 polypeptides are able to slow the proliferation of KIR3DL2-expressing CD4+ T cells. The KIR3DL2-binding compounds of the invention are capable of directly inhibiting the proliferation of KIR3DL2-expressing cells, particularly CD4+ T cells, in the absence of effector cells, accessory cells, or compositions having co-stimulatory function. This inhibition is believed to occur as a result of the activation of KIRDL2 signalling by the antigen-binding protein, whereby the KIR3DL2 protein transmits an inhibitory signal with the net result of inhibiting cell growth. The finding is surprising in part because there have not been any reports CD4+ T cells with functional inhibitory KIR, and also because KIR-mediated signalling has until now, in CD8+ T and NK cells, been involved in regulating effector cell cytotoxicity and not cell proliferation. The knowledge of KIR signalling in CD4+ T cells has been limited to activatory KIR (e.g. KIRDS polypeptides), and these have been reported only to have a co-activatory role, rather than the true activatory role in NK cells. The lack of true activatory function was reported to be due to missing "DAP12" signalling adaptors in T cells. It was furthermore discovered that the anti-KIR3DL2 antibodies that inhibited cell proliferation directly were additionally capable of mediating ADCC toward KIR3DL2-expressing cells when containing Fc portions that bind Fc receptors. The anti-KIR3DL2 antibodies were furthermore capable of binding their target with high affinity even when present in a less than decavalent (e.g. as would be the case for an IgM) form. Notably, KIR3DL2 antibodies of the invention in bivalent form were capable of mediating ADCC of KIR3DL2-expressing cells demonstrating that they are of substantially high affinity.

The particular antibodies disclosed herein bind a common determinant or epitope shared by the monomeric KIR3DL1 and KIR3DS1 and the dimeric KIR3DL2. The identification that the antibodies are capable of acting directly on KIR3DL2, e.g. to transmit an inhibitory signal intracellularly, in a KIR3DL2-expressing T cell indicates that the antibody will be suitable to increase therapeutic activity compared to other anti-KIR3DL2 antibodies. The antibody's anti-KIR3DL1 binding ability may provide further therapeutic activity in the treatment, e.g. of CD4+ T cells that express KIR3DL1, where the antibody may directly inhibit KIR3DL1-mediated proliferation and/or cytokine production or cytotoxicity, as well as mediate ADCC-mediated elimination of KIR3DL1-expressing cells.

It was also observed, independently of any effect of inhibition of proliferation, that the antibodies' ability to mediate ADCC toward KIR3DL2-expressing cells could be significantly improved by modification of the Fc portion of the antibody by producing it in a cell line which generates antibodies having a glycosylation profile different from e.g. typical CHO cells lines used to produce therapeutic recombinant antibodies. These modified Fc portions are hypofucosylated, believed to increase their binding to Fc receptors, e.g. Fcγ receptors on effector cells.

Importantly, the compounds of the invention are able to directly target KIR3D-expressing CD4+ T cells, particularly KIR3DL-expressing cells, and inhibit their activity, and in particular inhibit their proliferation. Significantly, as these effects depend solely on the interaction of the compound with the KIR3DL polypeptide, they can occur with "naked" compounds (particularly antibodies), i.e. compounds that have not been modified or derivatized with toxic compounds. Further, when the compounds are antibodies, they can effectively target tumor cells even without relying on immune cell mediated killing of the tumor cells (ADCC) (although it should be emphasized that ADCC can also take place in many contexts, further enhancing the efficacy of the treatment). Accordingly, the present compounds are particularly useful for patients with a compromised immune system, e.g., patients with AIDS, patients taking chemotherapy, or patients taking immunosuppressive drug regimens.

Although the compounds of the invention can be any type of molecular entity (e.g. polypeptide, small molecule) that can specifically bind to KIR3DL2-expressing cells and thereby inhibit their growth and proliferation, preferred compounds of the invention are antibodies. The compounds will preferably act as agonists at KIR3DL2, e.g. as may be present on CD4+ T cells, where the agonism of KIR3DL2 results in a net inhibition of proliferation or other activity (e.g. cytokine production, cytotoxicity) of the cell. Particularly preferred antibodies are bivalent IgG antibodies, as they can typically not only directly decrease target cell number by inhibiting cell proliferation, but also comprise Fc tails and have sufficient binding affinity to induce the killing of the cells through ADCC. Accordingly, by selecting the proper antibodies (bivalent IgG antibodies that target KIR3DL2 having modified Fc tails, most preferably the KIR3DL2 epitope recognized by antibody chAZ158), it is possible to target KIR3DL2-expressing tumor cells through two independent mechanisms (growth inhibition and ADCC). Together, these discoveries therefore provide unexpected ways to produce particularly efficacious antigen-binding compounds, most preferably antibodies, that have, inter alia, desired ADCC or anti-cell proliferation properties as well as, typically, ADCC-inducing effects. Methods of producing and using such antigen-binding compounds, as well as exemplary antigen-binding compounds, are described.

The invention provides methods of using the antigen-binding compounds; for example, the invention provides a method for inhibiting cell proliferation or activity and/or inducing ADCC, comprising exposing a cell, such as a T cells which expresses a KIR3DL polypeptide, to an antigen-binding compound that binds a KIR3DL2 polypeptide in an amount effective to induce ADCC and/or inhibit cell proliferation. It will be appreciated that for the purposes of the present invention, "cell proliferation" can refer to any aspect of the growth or proliferation of cells, e.g., cell growth, cell division, or any aspect of the cell cycle. The cell may be in cell culture or in a mammal, e.g. a mammal suffering from a KIR3DL-expressing pathology. The invention also provides a method for inducing ADCC of or inhibiting the proliferation of a cell which expresses a KIR3DL polypeptide, comprising exposing the cell to an antigen-binding compound (e.g. exogenous antibody) that binds a KIR3DL2 polypeptide as described herein in an amount effective to induce ADCC or inhibit the proliferation of the cell. Thus, the invention provides a method for treating a mammal suffering from a condition characterized by a pathogenic expansion of cells expressing of a KIR3DL polypeptide, e.g. KIR3DL1 or KIR3DL2, comprising administering a pharmaceutically effective amount of an antigen-binding compound disclosed herein to the mammal. Examples of such conditions include Sezary Syndrome, Mycosis Fungoides, CTCL, and autoimmune or inflammatory conditions, e.g. arthritis, cardiovascular disease. In preferred embodiments, the compound is an antibody, e.g. a bivalent IgG antibody and is effective at inducing ADCC of the cells.

The present invention provides methods for producing antigen-binding compounds, particularly antibodies, that specifically bind a KIR3DL2 polypeptide and that are useful for the treatment of T cell lymphomas (e.g. CTCL, Sezary Syndrome and Mycosis Fungoides), autoimmune disorders and inflammatory disorders, particularly when mediated at least in part by CD4+ T cells. The antigen-binding compounds produced using the present methods are capable of specifically targeting T lymphoma cells or other cells expressing a KIR3DL polypeptide, particularly an epitope on a KIR3DL2 polypeptide recognized by antibody chAZ158. The antigen-binding compound can limit the pathological effects of cell proliferation and/or activity by inhibiting the proliferation or activity of the cells and/or by targeting them for destruction by the immune system (e.g., via ADCC).

Several KIR3DL-expressing disorders, particularly T cell mediated disorders can be treated using the methods and compositions of the invention. The disorders may be for example CD4+ T cell malignancies such as CTCL, MF or SS, or autoimmune or inflammatory disorders where the elimination or inhibiting the activity and/or proliferation of CD4+ T cells would be useful. CD4+ T cells includes for example activated CD4+ T cells, CD4+ T cells expressing or not one or more other markers (e.g. CD2+, CD3+, CD5+, CD8−, CD28$^+$, CD28$^−$, CD45RO+ and TCRαβ+). CD4+CD28− T cells, for example, are known to express KIR3DL and are present in high frequencies of clonally expanded cells in some autoimmune and inflammatory disorders but are rare in healthy individuals. These T cells can be cytotoxic, secrete large amounts of IFN-gamma, and proliferate upon stimulation with autologous adherent mononuclear cells.

Cutaneous and circulating MF/SS cells have been reported to not express preferential alleles among nine KIR3DL2 alleles tested. Thirteen alleles have also been described to date. Whereas the p140-KIR3DL2 receptor is expressed on a minor subset of NK cells and on rare CD8+ T cells in healthy persons, it appears to be restricted to CTCL tumor CD4+ T cells in MF/SS patients. Other receptors that are usually observed at the surface of NK cells (such as p58.1, p58.2, p70KIRs, CD94/NKG2A) are not found at the surface of malignant CD4+ T cells (Bahler D. W. et al., (2008) Cytometry B Clin Cytom. 74(3):156-62). SS cells are also typically characterized, in addition to CD4+, by having a mature T lymphocyte phenotype, CD2+, CD3+, CD5+, CD8−, CD28+, CD45RO+ and TCRαβ+.

The methods and compositions of the invention can also be used in the treatment of autoimmune and inflammatory conditions characterized by KIR3DL expression. For example, it has been shown that several such disorders are mediated at least in part by CD4+ T cells, including particular CD4+ CD28null T cells. Activation of CD4+ T cells is generally thought to be governed by interplay between stimulatory and inhibitory receptors, where a predominance of stimulatory signals favors autoimmune reactions. Chan et al. ((2005) Arthrit. Rheumatism 52(11): 3586-3595 report that increased number of peripheral blood and synovial fluid CD4+ T cells and NK cells express KIR3DL2 in spondylarthritis. In patients with rheumatoid arthritis, expression of the critical costimulatory molecule, CD28, is frequently lost. Instead, a CD4$^+$ T cell population which lacks CD28 (CD4$^+$CD28$^-$ T cells) express killer immunoglobulin-like receptors (KIRs). CD4+CD28$^{null}$ T cells in particular have been reported to express KIR3D polypeptides. Compared with their CD28$^+$ counterparts, CD4+CD28– cells produce significantly higher levels of IFN-γ giving them the ability to function as proinflammatory cells. CD4$^+$CD28$^{null}$ T cell clones persist for years in circulation. These T cells are known to differ from CD28$^+$ T cells by being resistant to Fas-mediated apoptosis upon cross-linking of CD3. CD28$^{null}$ T cells progress through the cell cycle, and cells at all stages of the cell cycle are resistant to apoptosis, unlike their CD28$^+$ counterparts. Dysregulation of apoptotic pathways in CD4$^+$CD28$^{null}$ T cells has been shown to favor their clonal outgrowth and maintenance in vivo. Namekawa et al. ((2000) J. Immunol. 165:1138-1145 report that KIR, including KIR3DL2, was present on CD4+ CD28null T cells expanded in rheumatoid arthritis. Rheumatoid arthritis involves lymphocyte infiltrates, inflammatory mediators, and synovial hyperplasia resulting from aggressive proliferation of fibroblast-like synoviocytes and macrophages. Prognoses of joint erosions and disease severity correlate with high frequencies of clonally expanded CD4$^+$ CD28$^-$ T cells. Lamprecht et al. (2001) Thorax 56:751-757 report recruitment of CD4$^+$CD28$^-$ T cells in Wegener's granulomatosis. Markovic-Plese et al. (2001) J Clin Invest. 108: 1185-1194 report the presence of CD4+CD28– costimulation-independent T cells in the CNS, and their associate with multiple sclerosis. The methods and compositions of the invention can therefore be used in the treatment or prevention of Wegener's granulomatosis, multiple sclerosis or other central nervous system inflammatory or autoimmune disorders, arthritis, or other rheumatic disorders characterized by inflammation.

CD4$^+$CD28$^-$ T cells have also been associated with cardiovascular disorders. Betjes et al. (2008) Kidney International 74, 760-767 report that the increased risk for atherosclerotic disease in patients with Cytomegalovirus (CMV) seropositivity is associated with age-dependent increase of CD4$^+$ CD28$^-$ T cells, which can comprise over half of the circulating CD4 T cells in individuals. Patients over 50 years of age were reported to have a 50-fold higher percentage of CD4$^+$ CD28$^-$ T cells compared to CMV seronegative patients and a 5-fold higher percentage when compared to seropositive healthy controls. Nakajima et al. ((2003) Circ. Res. 93:106-113) report de novo expression of KIR in acute coronary syndrome, where CD4+ T cells from patients with acute coronary syndrome (ACS) express multiple KIR whereas normal CD4+CD28null T cells from healthy donors do not express KIR. Yen et al. Journal of Experimental Medicine, Volume 193, Number 10, May 21, 2001 1159-1168 studied CD4$^+$CD28$^{null}$ T cell clones established from patients with rheumatoid vasculitis for the expression of inhibitory and stimulatory KIR by RT-PCR. In patients with rheumatoid arthritis and a patient with ACS, the expression patterns favored the inhibitory KIR, including KIR3DL2, whereas expression of stimulatory receptors was highly restricted to KIR2DS2. The methods and compositions of the invention can therefore be used in the treatment or prevention of cardiovascular disorders, e.g. ACS, atherosclerotic disease, rheumatoid vasculitis, characterized by inflammation.

The present invention provides novel methods for producing and using antibodies and other compounds suitable for the treatment of disorders (e.g. cancers) where slowing the growth of and/or eliminating KIR3DL2-expressing cells would be useful. Antibodies, antibody derivatives, antibody fragments, and hybridomas are encompassed, as are methods of producing the same and methods of treating patients using the antibodies and compounds.

DEFINITIONS

As used herein, "T" cells refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art.

Within the context of this invention, "active" or "activated" T cells designate biologically active T cells, more particularly T cells having the capacity of cytolysis or of stimulating an immune response by, e.g., secreting cytokines. Active cells can be detected in any of a number of well known methods, including functional assays and expression-based assays such as the expression of cytokines such as TNF-alpha.

Within the context of this invention a "common determinant" designates a determinant or epitope that is shared by several gene products of the human inhibitory KIR3D receptors (e.g. share by at least two KIR3D receptors, shared by all KIR3D receptors). More preferably, the determinant is shared by at least KIR3DL1 and KIR3DL2, and optionally further by KIR3DS1. The determinant or epitope may represent a peptide fragment or a conformational epitope shared by said members. In a more specific embodiment, the antibody of this invention specifically binds to substantially the same epitope recognized by monoclonal antibody chAZ158. This determinant is present on KIR3DL1, KIR3DL2 and KIR3DS1. Within the context of this invention, the term antibody that "binds" a common determinant designates an antibody that binds said determinant with specificity and/or affinity.

KIR3DL2 (CD158k) is a disulphide-linked homodimer of three-Ig domain molecules of about 140 kD, described in Pende et al. (1996) J. Exp. Med. 184: 505-518, the disclosure of which is incorporated herein by reference. KIR3DL1 (CD158e1) is a monomeric molecule of about 70 kD, described in Colonna and Samaridis (1995) Science 268 (5209), 405-408. As used herein, "KIR3D" refers to any KIR3D receptor (e.g. KIR3DL1, KIR3DL2, KIR3DS1) individually or collectively, and the term "KIR3D" may be substituted by the term "KIR3DL1, KIR3DL2 and/or KIR3DS1". Similarly, "KIR3DL" refers to any KIR3DL receptor (e.g. KIR3DL1, KIR3DL2) individually or collectively, and the term "KIR3DL" may be substituted by the term "KIR3DL1 and/or KIR3DL2". The terms "KIR3D", "KIR3DL", "KIR3DL1", "KIR3DL2", "KIR3DS1" each furthermore include any variant, derivative, or isoform of the KIR3D gene or encoded protein(s) to which they refer. Several allelic variants have been reported for KIR3D polypeptides (e.g. KIR3DL2), each of these are encompassed by the respective terms. Sequences of human KIR3DL1 are also shown in SEQ ID NOS 1 and 2 for human cDNA and amino acid sequences, respectively, corresponding to Genbank accession nos. L41269 and AAA69870. Sequences of human KIR3DL2 are also shown in SEQ ID NOS 3 and 4 for human cDNA and amino acid sequences, respectively, corresponding to Genbank accession nos. L41270 and AAA69871. Sequences of human KIR3DS1 (CD158e2) are also shown in SEQ ID NOS 5 and 6 for human cDNA and amino acid sequences, respectively, corresponding to Genbank accession nos. L76661 and AAB36589. Also encompassed are any nucleic acid or protein sequences sharing one or more biological properties or functions with wild type, full length KIR3DL or KIR3DS, respectively, and sharing at least 70%, 80%, 90%, 95%, 96%, 97%, 98%, 99%, or higher nucleotide or amino acid identity.

As used herein "KIR3DL signaling" or "KIR3DL2 signaling" refers to an ability of a KIR3DL or KIR3DL2 polypeptide, respectively, to activate or transducer an intracellular signaling pathway. Changes in KIR3DL signaling activity can be measured, for example, by assays designed to measure changes in KIR3DL signaling pathways, e.g. by monitoring phosphorylation of signal transduction components such as SHP-1, assays to measure the association of certain signal transduction components with other proteins or intracellular structures, or in the biochemical activity of components such as kinases, or assays designed to measure expression of reporter genes under control of KIR3DL-sensitive promoters and enhancers, or indirectly by a downstream effect mediated by the KIR3DL polypeptide (e.g. inhibition of cell proliferation). Reporter genes can be naturally occurring genes (e.g. monitoring cytokine production) or they can be genes artificially introduced into a cell. Other genes can be placed under the control of such regulatory elements and thus serve to report the level of KIR3DL signaling.

As used herein, the terms "stimulating" or "activating" with respect to the effect of the herein-described compounds on KIR3DL refers to the ability of the compounds to bind to KIR3DL (e.g. KIR3DL2) present on the surface or in a cytoplasmic compartment of a cell, and to induce KIR3DL (e.g. KIR3DL2) signaling. Any detectable difference in KIR3DL signaling can indicate that a compound stimulates or activates a KIR3DL receptor. Regardless of the assay used, an alteration of 10%, 20%, 30%, 40%, 50%, 60%, 70%, 80%, 90%, 100%, 200%, 300%, 400%, 500%, 1000%, or more in any aspect of KIR3DL signaling may be indicative of stimulation or activation.

The terms "depleting", with respect to KIR3DL-expressing cells means a process, method, or compound that can kill, eliminate, lyse or induce such killing, elimination or lysis, so as to negatively affect the number of KIR3DL-expressing cells present in a sample or in a subject.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. KIR3DL2, as assessed using either recombinant forms of the proteins, epitopes therein, or native proteins present on the surface of isolated T cells or other target cells. Competitive binding assays and other methods for determining specific binding are further described below and are well known in the art.

When an antibody or agent is said to "compete" or "bind to substantially the same epitope" as a particular monoclonal antibody (e.g. the bivalent antibody comprising a heavy chain variable region comprising SEQ ID NO 8 and a light chain variable region comprising SEQ ID NO 10), it means that the antibody or agent competes with the monoclonal antibody in a binding assay using either recombinant KIR3D (e.g. KIR3DL2) molecules or surface expressed KIR3D (e.g. KIR3DL2) molecules. For example, if a test antibody or agent reduces the binding of a bivalent antibody comprising a heavy chain variable region comprising SEQ ID NO 8 and a light chain variable region comprising SEQ ID NO 10 to a KIR3D (e.g. KIR3DL2) polypeptide in a binding assay, the antibody or agent is said to "compete" with chAZ158, respectively.

By "immunogenic fragment," it is herein meant any polypeptidic or peptidic fragment that is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

"Toxic" or "cytotoxic" peptides or small molecules encompass any compound that can slow down, halt, or reverse the proliferation of cells, decrease their activity in any detectable way, or directly or indirectly kill them. Preferably, toxic or cytotoxic compounds work by directly killing the cells, by provoking ADCC or otherwise. As used herein, a toxic "peptide" can include any peptide, polypeptide, or derivative of such, including peptide- or polypeptide-derivatives with unnatural amino acids or modified linkages. A toxic "small molecule" can includes any toxic compound or element, preferably with a size of less than 10 kD, 5 kD, 1 kD, 750 D, 600 D, 500 D, 400 D, 300 D, or smaller.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet. 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample, or tissue sample (for example bone marrow or tissue biopsy including mucosal tissue such as from the gut, gut lamina propria, or lungs).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The terms "Fc domain", "Fc portion", "Fc tail" and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

"Autoimmune" disorders include any disorder, condition, or disease in which the immune system mounts a reaction against self cells or tissues, due to a breakdown in the ability to distinguish self from non-self or otherwise. Examples of autoimmune disorders include rheumatoid arthritis, rheumatoid vascularitis, systemic lupus erythematosus, multiple sclerosis, Wegener's granulomatosus, spondylarthritis, and others. An "inflammatory disorder" includes any disorder characterized by an unwanted immune response. Autoimmune and inflammatory disorders can involve any component of the immune system, and can target any cell or tissue type in the body.

Producing Anti-KIR3DL2 Antibodies

The antibodies of this invention specifically bind to KIR3DL2 polypeptides, e.g., KIR3DL2 polypeptides on the surface of human cells. The ability of the antibodies to bind KIR3DL2 polypeptides makes them useful for numerous applications, e.g., purifying human or other primate cells, or specifically labeling human or other primate cells in vitro, in vivo, or ex vivo. The ability to specifically purify and label cells is useful for, inter alia, diagnostic purposes (e.g. to detect human malignant CD4+ T cells involved in autoimmune or inflammatory disorders such as arthritis, cardiovascular disease). In certain embodiments, the antibodies also specifically bind to KIR3DL1 and/or KIR3DS1 polypeptides in addition to KIR3DL2, e.g., KIR3DL1 and/or KIR3DS1 polypeptides on the surface of human cells. Preferably the antibodies comprise a constant region capable of crosslinking receptors (e.g. antibody having a constant region of human IgG1 subtype, or other subtype having the ability to bind Fc receptors). Such antibodies can readily be modified so as to have properties of depleting KIR3DL-expressing cells, particularly via ADCC. The antibodies can be prepared so as to have an Fc portion that binds CD16 and induces ADCC. Optionally the Fc region is modified (e.g. glycosylation modified, hypofucsylated, comprising amino acid modifications, etc.) so as to have increased ADCC activity compared to a reference Fc portion.

As such, the present antibodies are useful for, inter alia, treating or preventing disorders characterized by a pathogenic expansion of KIR3D-expressing cells, e.g., conditions resulting from an increase in the number or activity of KIR3D- expressing cells, or conditions that can be prevented or ameliorated by decreasing the number or activity of KIR3DL-expressing cells.

In a preferred embodiment, the invention provides an antibody that binds a human KIR3DL2 dimer, modulates the activity or proliferation of T cells, and competes with monoclonal antibody chAZ158 for binding to human KIR3DL2. Optionally, said antibody is a chimeric, human, or humanized antibody. Depending on the antibodies or particular derivative or fragment used, the antibodies of the invention can either increase or decrease the activity of T cells.

In an advantageous aspect, the invention provides an antibody that competes with the bivalent antibody comprising a heavy chain variable region comprising SEQ ID NO 8 and a light chain variable region comprising SEQ ID NO 10 and recognizes, binds to, or has immunospecificity for substantially or essentially the same, or the same, epitope or "epitopic site" on a KIR3DL2, KIR3DL1 and/or KIR3DS1 molecule. In other embodiments, the monoclonal antibody consists of, or is a derivative or fragment thereof.

The antibodies of this invention may be produced by a variety of techniques known in the art. Typically, they are produced by immunization of a non-human animal, preferably a mouse, with an immunogen comprising a KIR3DL polypeptide, preferably a cell expressing at its surface a human KIR3DL2 dimer. The KIR3DL polypeptide may comprise the full length sequence of a human KIR3DL polypeptide, or a fragment or derivative thereof, typically an immunogenic fragment, i.e., a portion of the polypeptide comprising an epitope exposed on the surface of cells expressing a KIR3DL polypeptide. Such fragments typically contain at least about 7 consecutive amino acids of the mature polypeptide sequence, even more preferably at least about 10 consecutive amino acids thereof. Fragments typically are essentially derived from the extra-cellular domain of the receptor. In a preferred embodiment, the immunogen comprises a wild-type human KIR3DL2 polypeptide in a lipid membrane, typically at the surface of a cell. In a specific embodiment, the immunogen comprises intact SS or MF cells, particularly intact human malignant CD4+ T cells, or CD4+CD28-T cells, optionally treated or lysed. In another preferred embodiment, the polypeptide is a recombinant dimeric KIR3DL2 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with KIR3DL2 polypeptides.

In an alternate embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to KIR3DL polypeptides. The assay is typically a colorimetric ELISA-type assay, although any assay may be employed that can be adapted to the wells that the hybridomas are grown in. Other assays include and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to substantially or essentially the same epitope as the anti-KIR3DL2 monoclonal antibodies described herein can be readily determined using any one of variety of immunological screening assays in which antibody competition can be assessed. A number of such assays are routinely practiced and well known in the art (see, e.g. U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (for example chAZ158, which is a bivalent antibody comprising a heavy chain variable region comprising SEQ ID NO 8 and a light chain variable region comprising SEQ ID NO 10) and test antibodies are admixed (or pre-adsorbed) and applied to a sample containing KIR3DL polypeptides. Protocols based upon Western blotting and the use of BIACORE analysis are suitable for use in such simple competition studies.

In certain embodiments, one pre-mixes the control antibodies (chAZ158, for example) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e.g. by using separation or washing techniques to eliminate unbound antibodies) and chAZ158 from the test antibodies (e.g., by using species-specific or isotype-specific secondary antibodies or by specifically labeling chAZ158 with a detectable label) one can determine if the test antibodies reduce the binding of chAZ158 to the antigens, indicating that the test antibody recognizes substantially the same epitope as chAZ158. The binding of the (labeled) control antibodies in the absence of a completely irrelevant antibody can serve as the control high value. The control low value can be obtained by incubating the labeled (chAZ158) antibodies with unlabelled antibodies of exactly the same type (chAZ158), where competition would occur and reduce binding of the labeled antibodies. In a test assay, a significant reduction in labeled antibody reactivity in the presence of a test antibody is indicative of a test antibody that recognizes substantially the same epitope. Any test antibody that reduces the binding of chAZ158 to KIR3DL2 antigens by at least about 50%, such as at least about 60%, or more preferably at least about 70% (e.g., about 65-100%), at any ratio of chAZ158:test antibody between about 1:10 and about 1:100 is considered to be an antibody that binds to substantially the same epitope or determinant as chAZ158. Preferably, such test antibody will reduce the binding of chAZ158 to the KIR3DL2 antigen by at least about 90% (e.g., about 95%).

Competition can be assessed by, for example, a flow cytometry test. In such a test, cells bearing a KIR3DL2 polypeptide can be incubated first with chAZ158, for example, and then with the test antibody labeled with a fluorochrome or biotin. The test antibody can be assessed in the same way for competition chAZ158 for KIR3DL1 and KIR3DS1. The antibody is said to compete with chAZ158 if the binding obtained upon preincubation with a saturating amount of chAZ158 is about 80%, preferably about 50%, about 40% or less (e.g., about 30%) of the binding (as measured by mean of fluorescence) obtained by the antibody without preincubation with chAZ158. Alternatively, an antibody is said to compete with chAZ158 if the binding obtained with a labeled chAZ158 antibody (by a fluorochrome or biotin) on cells preincubated with a saturating amount of test antibody is about 80%, preferably about 50%, about 40%, or less (e.g., about 30%) of the binding obtained without preincubation with the antibody.

A simple competition assay in which a test antibody is pre-adsorbed and applied at saturating concentration to a surface onto which a KIR3DL2 antigen is immobilized may also be employed. The surface in the simple competition assay is preferably a BIACORE chip (or other media suitable for surface plasmon resonance analysis). The control antibody (e.g., chAZ158) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody recognizes substantially the same epitope as the control antibody. Any test antibody that reduces the binding of control (such as chAZ158) antibody to a KIR3DL2 antigen by at least about 30% or more, preferably about 40%, can be considered to be an antibody that binds to substantially the same epitope or determinant as a control (e.g., chAZ158). Preferably, such a test antibody will reduce the binding of the control antibody (e.g., chAZ158) to the KIR3DL2 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal and (1995) J. Immunol. Methods 183: 33-41, the disclosure of which is incorporated herein by reference.

Preferably, monoclonal antibodies that recognize a KIR3DL2 epitope will react with an epitope that is present on a substantial percentage of or even all relevant cells, e.g malignant CD4+ T cells, cells from a SS or MF patient, but will not significantly react with other cells, i.e., immune or non-immune cells that do not express KIR3DL2. In one aspect, the anti-KIR3DL2 antibodies of the invention bind KIR3DL2 but do not bind KIR3DL1 and/or KIR3DS1. In another aspect, monoclonal antibodies that recognize a KIR3DL2 epitope bind a common determinant present on KIR3DL1 and KIR3DL2, and optionally further a common determinant present on KIR3DS1.

In preferred embodiments, the antibodies will bind to KIR3DL2-expressing cells from an individual or individuals with a disease characterized by expression of KIR3DL2-positive cells, i.e. an individual that is a candidate for treatment with one of the herein-described methods using an anti-KIR3DL2 antibody of the invention. Accordingly, once an antibody that specifically recognizes KIR3DL2 on cells is obtained, it can be tested for its ability to bind to KIR3DL2-positive cells (e.g. malignant CD4+ T cells) taken from a patient with a disorder such as SS or MF. In particular, prior to treating a patient with one of the present antibodies, it will be beneficial to test the ability of the antibody to bind malignant cells taken from the patient, e.g. in a blood sample, to maximize the likelihood that the therapy will be beneficial in the patient.

In one embodiment, the antibodies of the invention are validated in an immunoassay to test their ability to bind to KIR3DL2-expressing cells, e.g. malignant CD4+ T cells, pro-inflammatory CD4+ cells. For example, peripheral blood lymphocytes (PBLs) are taken from a plurality of patients, and CD4+ T cells are enriched from the PBLs, e.g., by flow cytometry using relevant antibodies (for malignant CD4+ cells see, e.g., Bagot et al. (2001) Blood 97:1388-1391, the disclosure of which is incorporated herein by reference), or CD4+CD28− cell fractions are isolated by magnetic separation on a MACS column (Miltenyi Biotec). The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express KIR3DL2, e.g. T cells, from a significant percentage of individuals or patients (e.g., 5%, 10%, 20%, 30%, 40%, 50% or more) are suitable for use in the present invention, both for diagnostic purposes to determine the presence or level of malignant T cells in a patient or for use in the herein-described therapeutic methods, e.g., for use to increase or decrease malignant T cell number or activity. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). Such methods are well known to those of skill in the art.

While described in the context of chAZ158 for the purposes of exemplification, it will be appreciated that the herein-described immunological screening assays and other assays can also be used to identify antibodies that compete with other anti-KIR3DL2 antibodies, and other antibodies described herein or obtained according to the teachings of the present specification.

Determination of whether an antibody binds within one of the epitope regions defined above can be carried out in ways known to the person skilled in the art. As one example of such mapping/characterization methods, an epitope region for an anti-KIR3DL2 antibody may be determined by epitope "footprinting" using chemical modification of the exposed amines/carboxyls in the KIR3DL2 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst, Schering Res Found Workshop. 2004; (44): 149-67; Huang et al. Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downard, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to KIR3DL2 or o/n digestion at and pH 7-8, followed by mass spectrometry (MS) analysis for peptide identification. The peptides protected from trypsin cleavage by the anti-KIR3DL2 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc. also or alternatively can be used in similar epitope characterization methods. Moreover, enzymatic digestion can provide a quick method for analyzing whether a potential antigenic determinant sequence is within a region of the KIR3DL2 polypeptide that is not surface exposed and, accordingly, most likely not relevant in terms of immunogenicity/antigenicity.

Upon immunization and production of antibodies in a vertebrate or cell, particular selection steps may be performed to isolate antibodies as claimed. In this regard, in a specific embodiment, the invention also relates to methods of producing such antibodies, comprising: (a) immunizing a non-human mammal with an immunogen comprising a KIR3DL2 polypeptide; and (b) preparing antibodies from said immunized animal, wherein said antibodies bind said KIR3DL2 polypeptide. In one embodiment, the method further comprises step (c), selecting antibodies of (b) that are capable of depleting or inhibiting the proliferation of KIR3DL2-expressing cells, or that activate KIR3DL2 (e.g. induce receptor signaling).

In preferred embodiments, the antibodies prepared according to the present methods are monoclonal antibodies. In preferred embodiments, the non-human animal used to produce antibodies according to the methods of the invention is a mammal, such as a rodent, bovine, porcine, horse, rabbit, goat, or sheep.

According to an alternate embodiment, the DNA encoding an antibody that binds an epitope present on KIR3DL2 polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, or chimeric antibodies comprising the antigen recognition portion of the antibody.

DNA encoding the monoclonal antibodies can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, preferred host cells include avian host cells, as well as any other cells capable of producing hypofucosylated antibodies. The DNA sequences described herein can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, pp. 151 (1992). The invention therefore provides a host cell capable of expressing an antibody that binds an epitope present on KIR3DL2 polypeptides, including but not limited to a recombinant host cell which has been transformed with a nucleic acid encoding an antibody that binds an epitope present on a KIR3DL2 polypeptide.

Testing the Compounds for Activity

Once an antigen-binding compound is obtained it will generally be assessed for its ability to interact with, affect the activity of, and/or induce ADCC towards and/or inhibit the proliferation of target cells or activate KIR3DL2 (e.g. induce receptor signaling). Assessing the antigen-binding compound's ability to induce ADCC or activate KIR3DL2, whether directly by monitoring signal transduction pathways or indirectly by monitoring inhibition of the proliferation of target cells, can be carried out at any suitable stage of the method, and examples are provided herein. This assessment can be useful at one or more of the various steps involved in the identification, production and/or development of an antibody (or other compound) destined for therapeutic use. For example, ADCC, receptor signaling or anti-cell proliferation activity may be assessed in the context of a screening method to identify candidate antigen-binding compounds, or in methods where an antigen-binding compound is selected and made human suitable (e.g. made chimeric or humanized in the case of an antibody), where a cell expressing the antigen-binding compound (e.g. a host cell expressing a recombinant antigen-binding compound) has been obtained and is assessed for its ability to produce functional antibodies (or other compounds), and/or where a quantity of antigen-binding compound has been produced and is to be assessed for activity (e.g. to test batches or lots of product). Generally the antigen-binding compound will be known to specifically bind to a KIR3DL2 polypeptide. The step may involve testing a plurality (e.g., a very large number using high throughput screening methods or a smaller number) of antigen-binding compounds for their ADCC induction or anti-cell proliferation activity, or testing a single compound.

Typically, analysis of the anti-KIR3DL2 antibody's activity in activating KIR3DL2 by monitoring signal transduction, e.g. the inhibitory signalling cascade, involves monitoring KIR3DL2-induced phosphorylation patterns. Preferably, phosphorylation of molecules implicated in KIR inhibitory signalling such as SHP-1 is followed. Upon signalling, SHP-1 appears phosphorylated upon KIR3DL2 engagement as it has been previously shown for other inhibitory receptors (Vely F, (1997) Eur. J. Immunol. 27(8): 1994-2000; Yusa S, (2002) J. Immun. 168(10):5047-57; Long E O, (2001) Immunol. Rev. 181:223-33; and Carretero M, (1998) Eur. J. Immunol. 28(4):1280-91). The experiment is carried out with an anti-KIR3DL2 antibody (e.g. chAZ158) binding to KIR3DL2 with different cell lines or freshly sorted human cells. Each these references for assays are herein incorporated by reference in their entirety.

Other preferred assays include indirect approaches to detect KIR3DL2 receptor signalling. In one example, the effect chAZ158 antibody on the inhibition of phosphorylation of molecules implicated in the activation cascade under TCR/CD3 activation is evaluated. Many molecules such as SLP-76, LAT, vav-1 or ZAP-70 are implicated in the TCR/CD3 activating pathway (Leo A, (2001) Current Opinions Immunol. 13(3):307-16; Horejsi V, (2004) Nature Reviews 4(8):603-16). As the AZ158 chimeric antibody can also be assessed for its ability to inhibit the proliferation of cells previously activated by anti-CD3 antibodies, by monitoring a decrease in the phosphorylation of key molecules implicated in the TCR/CD3 activation pathway. These biochemical experiments are performed in presence or not of the anti-KIR3DL2 antibody (e.g. chAZ158) antibody as previously described for different membrane receptors (Chen X, (2007) PNAS 104(15):6329-34; Fourmentraux-Neves E, (2008) Blood 112(6):2381-9; Nikolova M, (2002) Blood 100(3): 1019-25; Stebbins C, (2003) Mol Cell Biol. 23(17):6291-9). The localization of the different molecules implicated in the KIR3DL2 inhibitory cascade or in the TCR/CD3 signalisation cascade are monitored by confocal microscopy (Liu Y, (2007) J. Leukocyte Biology 82: 742-751; Fourmentraux-Neves E, (2008)). This is done by incubating cell lines or freshly sorted human cells with free AZ158 antibodies or AZ158 coated beads to create a synaptic platform. Another indirect approach involves monitoring cellular effects of signalling, including cytokine production, cell proliferation or growth, markers of cytoxicity, etc. Each these references for assays are herein incorporated by reference in their entirety.

Examples of assays for assessing KIR3DL2 signalling includes the assays described herein in Example 5; cells expressing KIR3DL2, optionally further not expressing other KIR3D polypeptides (e.g. Sezary Syndrome cells which express KIR3DL2 but not other KIRs), are brought into contact with an anti-KIR3DL2 antibody (e.g. chAZ158 antibody)

in the absence of effector cells, and the cells' proliferation is assessed. Optionally cells express KIR3DL2 and additionally other KIR3D receptors to which an anti-KIR3D antibody binds. To measure cell proliferation or growth, any suitable method such as determining cell number or density, including the methods used in the Example 5 section herein (CellTiter-Glo Luminescent Cell Viability Assay, Promega) or determining the mitotic index, or any other method to determine the number of cells or their position in the cell cycle can be used. In vivo assays can be used as well, e.g. administering the antibodies to animal models, e.g., mice, containing target cells, and detecting the effect of the antibody administration on the survival, growth or activity of the target cells over time. In certain embodiments, an assay comprises detecting inhibition of cell proliferation in the absence of effector (e.g. NK) cells, where the antibody is capable of producing a decrease of at least 10%, 20%, 30%, 40%, 50% in the number of target cells or compared to target cells incubated in the absence of antibody. Target cells may be, for example, KIR3DL2-expressing cells, e.g. CD4+ T cells, Cou-L cells or malignant T cells from a SS or MF patient, CD4+CD28− T cells.

Testing antibody-dependent cellular cytotoxicity (ADCC) typically involves assessing cell-mediated cytotoxicity in which a KIR3DL-expressing target cell (e.g. a Cou-L cell, Sezary Syndrome cell or other KIR3DL-expressing cell) with bound anti-KIR3DL2 antibody is recognized by an effector cell bearing Fc receptors, without the involvement of complement. A cell which does not express a KIR3DL antigen can optionally be used as a control. Several exemplary ADCC assay is described in Example 5 herein. Activation of NK cell cytotoxicity is assessed by measuring an increase in cytokine production (e.g. IFN-γ production) or cytotoxicity markers (e.g. CD107 mobilization). Preferably the antibody of the invention will induce an increase in cytokine production, expression of cytotoxicity markers, or target cell lysis of at least 20%, 50%, 80%, 100%, 200% or 500% in the presence of target cells, compared to a control antibody (e.g. an antibody not binding to KIR3DL, a KIR3DL2 antibody having murine constant regions, a KIR3DL2 antibody produced in CHO cells and not hypofucosylated, etc.). In another example, lysis of target cells is detected, e.g. in a chromium release assay, preferably the antibody of the invention will induce lysis of at least 10%, 20%, 30%, 40% or 50% of target cells. Where an antigen-binding compound is tested for both its ability to (a) induce both ADCC and (b) induce KIR3DL2 activation (receptor signaling), the assays of (a) and (b) can be carried out in any order.

Fragments and Derivatives of the Present Monoclonal Antibodies

Fragments and derivatives of antibodies of this invention (which are encompassed by the term "antibody" or "antibodies" as used in this application, unless otherwise stated or clearly contradicted by context), preferably a chAZ158-like antibody, can be produced by techniques that are known in the art. "Fragments" comprise a portion of the intact antibody, generally the antigen binding site or variable region. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Examples of preferred antibody fragments also include any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Various types of antibody fragments have been described or reviewed in, e.g., Holliger and Hudson, (2005) Nat. Biotech. 23: 1126-1136; WO2005040219; and published U.S. Patent Applications 20050238646 and 20020161201

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of this invention may be modified so as to encode a fragment of this invention. The modified DNA is then inserted into an expression vector and used to transform or transfect an appropriate cell, which then expresses the desired fragment.

In certain embodiments, the DNA of a hybridoma producing an antibody of this invention can be modified prior to insertion into an expression vector, for example, by substituting the coding sequence for human heavy- and light-chain constant domains in place of the homologous non-human sequences (e.g., Morrison et al., Proc. Natl. Acad. Sci. U.S. pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

In one particularly preferred embodiment, the antibodies of this invention are humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine or other non-human immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. For further details see Jones et al. (1986) Nature 321: 522; Reichmann et al. (1988) Nature 332: 323; Verhoeyen et al. (1988) Science 239:1534 (1988); Presta (1992) Curr. Op. Struct. Biol. 2:593; each of which is herein incorporated by reference in its entirety.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al. (1993) J. Immun., 151:2296; Chothia and Lesk (1987) J. Mol. Biol. 196:901). Another method uses a particular framework from the consensus sequence of all human antibodies of a particular subgroup of light or heavy chains. The same framework can be used for several different humanized antibodies (Carter et al. (1992) PNAS 89:4285; Presta et al. (1993) J. Immunol. 51:1993)).

It is further important that antibodies be humanized while retaining their high affinity for KIR3DL2, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

In one example, the invention provides human, chimeric or humanized anti-KIR3DL2 antibodies having a half-life of at least 5, 6, 8, 9, 10, 15 or 20 days, and which substantially bind human FcgammaRIIIa (CD16) (e.g. via their constant region). For example an antibody having a constant region of the IgG1 type, or a F(ab')2 fragment will typically have CD16 binding). More preferably, the antibody is a human, chimeric or humanized activating anti-KIR3DL2 antibody which competes with antibody chAZ158 for binding to human KIR3DL2. For the purpose of illustration with preferred antibodies suitable for use according to the methods herein, a chAZ158 antibody can be used to prepare a humanized antibody. Preferred humanized antibodies according to the invention comprise a human framework, at least one CDR from a non-human antibody, and in which any constant region present is substantially identical to a human immunoglobulin constant region, e.g., at least about 60-90%, preferably at least 95% identical. Hence, all parts of a humanized antibody, except possibly the CDR's, are substantially identical to corresponding parts of one or more native human antibody sequences. In some instances, the humanized antibody, in addition to CDRs from a non-human antibody, would include additional non-human residues in the human framework region.

The design of humanized antibodies can be carried out as follows. When an amino acid falls under the following categories, the framework amino acid of a human antibody to be used (acceptor antibody) is replaced by a framework amino acid from a CDR-providing non-human antibody (donor antibody): (a) the amino acid in the human framework region of the acceptor antibody is unusual for human antibody at that position, whereas the corresponding amino acid in the donor antibody is typical for human antibody in that position; (b) the position of the amino acid is immediately adjacent to one of the CDR's; or (c) the amino acid is capable of interacting with the CDR's in a tertiary structure antibody model (see, C. Queen et al. Proc. Natl. Acad. Sci. USA 86, 10029 (1989), and Co et al., Proc. Natl. Acad. Sci. USA 88, 2869 (1991) the disclosures of which are incorporated herein by reference).

For further detailed description of the production of humanized antibody, See Queen et al., op. cit. and Co et al, op. cit. and U.S. Pat. Nos. 5,585,089; 5,693,762, 5,693,761, and 5,530,101, the disclosures of which are incorporated herein by reference. Usually, the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized antibody. Occasionally, substitutions of CDR regions can enhance binding affinity. Other than for the specific amino acid substitutions discussed above, the framework regions of humanized antibodies are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized antibody. The antigen binding region of the humanized antibody (the non-human portion) can be derived from an antibody of nonhuman origin, referred to as a donor antibody, having specificity for KIR3DL2. For example, a suitable antigen binding region can be derived from a chAZ158 monoclonal antibody. Other sources include KIR3DL2-specific antibodies obtained from nonhuman sources, such as rodent (e.g., mouse and rat), rabbit, pig, goat or non-human primate (e.g., monkey) or camelid animals (e.g., camels and llamas). Additionally, other polyclonal or monoclonal antibodies, such as antibodies which bind to the same or similar epitope as a chAZ158 antibody, can be made (e.g., Kohler et al., Nature, 256:495-497 (1975); Harlow et al., 1988, Antibodies: A Laboratory Manual, (Cold Spring Harbor, N.Y.); and Current Protocols in Molecular Biology, Vol. 2 (Supplement 27, Summer '94), Ausubel et al., Eds. (John Wiley & Sons: New York, N.Y.), Chapter 11 (1991)).

In one embodiment, the humanized antibody having binding specificity for human KIR3DL2 (optionally further binding KIR3DL1 and/or KIR3DS1) comprises at least one CDR of nonhuman origin. For example, a humanized antibody having a binding specificity for human KIR3DL2 comprises a heavy chain and a light chain. The light chain can comprise a CDR derived from an antibody of nonhuman origin which binds KIR3DL2 and a FR derived from a light chain of human origin. For example, the light chain can comprise CDR1, CDR2 and/or CDR3 which have the amino acid sequence similar or substantially the same as that of the respective CDR of a chAZ158 antibody such that the antibody specifically binds to the human KIR3DL2. The heavy chain can comprise a CDR derived from an antibody of nonhuman origin which binds KIR3DL2 and a FR derived from a heavy chain of human origin. For example, the heavy chain can comprise CDR1, CDR2 and CDR3 which have the amino acid sequence set forth below or an amino acid similar or substantially the same as that of the respective CDR of the chAZ158 antibody such that the antibody specifically binds to the human KIR3DL2.

An embodiment of the invention is a humanized antibody which specifically binds to human KIR3DL2, wherein the antibody binds a common determinant also present on KIR3DL1 and/or KIR3DS1, and wherein the antibody comprises a humanized light chain comprising three light chain CDRs from a chAZ158 antibody and a light chain variable region framework sequence from a human antibody light chain. The invention further comprises a humanized heavy chain that comprises three heavy chain CDRs from a chAZ158 antibody and a heavy chain variable region framework sequence from a human antibody heavy chain.

The portion of the humanized antibody or antibody chain which is of human origin (the human portion) can be derived from any suitable human antibody or antibody chain. For example, a human constant region or portion thereof, if present, can be derived from the kappa or lambda light chains, and/or the gamma (e.g., gamma1, gamma2, gamma3, gamma4), μ, alpha (e.g., alpha1, alpha2), delta or epsilon heavy chains of human antibodies, including allelic variants. A particular constant region, variants or portions thereof can be selected to tailor effector function. The latter constant regions, or portions therefore can be selected to have increased or decreased binding to Fcgamma receptors (e.g., CD16 on NK cells). If present, human FRs are preferably derived from a human antibody variable region having sequence similarity to the analogous or equivalent region of the antigen binding region donor. Other sources of FRs for portions of human origin of a humanized antibody include human variable consensus sequences (See, Kettleborough, C. A. et al., Protein Engineering 4:773-783 (1991); Queen et al., U.S. Pat. Nos. 5,585,089, 5,693,762 and 5,693,761, the teachings all of which are incorporated by reference herein in their entirety). For example, the sequence of the antibody or variable region used to obtain the nonhuman portion can be compared to human sequences as described in Kabat, E. A., et al., Sequences of Proteins of Immunological Interest, Fifth Edition, U.S. Department of Health and Human Services, U.S. Government Printing Office (1991). In a preferred embodiment, the FRs of a humanized antibody chain are derived from a human variable region having at least about 60% overall sequence identity, and preferably at least about 80% overall sequence identity, with the variable region of the nonhuman donor (e.g., chAZ158 antibody).

Amino acids from the variable regions of the mature heavy and light chains of antibodies are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalent position to an amino acid position L50 of a mouse antibody. From N-terminal to C-terminal, both light and heavy chain variable regions comprise alternating framework and (CDRs)" FR1, CDR1, FR2, CDR2, FR3, CDR3 and FR4. The assignment of amino acids to each region is in accordance with the definitions of Kabat (1987) and (1991), supra and/or Chothia & Lesk, J. Mol. Biol. 196:901-917 (1987); Chothia et al., Nature 342:878-883 (1989).

Binding and/or adhesion assays or other suitable methods can also be used in procedures for the identification and/or isolation of humanized antibodies (e.g., from a library) with the requisite specificity (competition assays for example).

The antibody portions of nonhuman and human origin for use in the invention include light chains, heavy chains and portions of light and heavy chains. These antibody portions can be obtained or derived from antibodies (e.g., by de novo synthesis of a portion), or nucleic acids encoding an antibody or chain thereof having the desired property (e.g., binds KIR3DL2, sequence similarity, for example with the chAZ158 antibody) can be produced and expressed. Humanized antibodies comprising the desired portions (e.g., antigen binding region, CDR, FR, C region) of human and nonhuman origin can be produced using synthetic and/or recombinant nucleic acids to prepare genes (e.g., cDNA) encoding the desired humanized chain. To prepare a portion of a chain, one or more stop codons can be introduced at the desired position. For example, nucleic acid sequences coding for newly designed humanized variable regions can be constructed using PCR mutagenesis methods to alter existing DNA sequences (see e.g., Kamman, M., et al., Nucl. Acids Res. 17:5404 (1989)). PCR primers coding for the new CDRs can be hybridized to a DNA template of a previously humanized variable region which is based on the same, or a very similar, human variable region (Sato, K., et al., Cancer Research 53:851-856 (1993)). If a similar DNA sequence is not available for use as a template, a nucleic acid comprising a sequence encoding a variable region sequence can be constructed from synthetic oligonucleotides (see e.g., Kolbinger, F., Protein Engineering 8:971-980 (1993)). A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C. A., Protein Engineering 4:773-783 (1991)). Using these methods, methods described herein or other suitable methods, variants can be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogengoom et al., WO 93/06213, published Apr. 1, 1993)).

The invention also relates to isolated and/or recombinant (including, e.g., essentially pure) nucleic acids comprising sequences which encode a humanized antibody or humanized antibody light or heavy chain of the present invention.

Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. Human antibodies may also be produced according to various other techniques, such as by using, for immunization, other transgenic animals that have been engineered to express a human antibody repertoire (Jakobovitz et Nature 362 (1993) 255), or by selection of antibody repertoires using phage display methods. Such techniques are known to the skilled person and can be implemented starting from monoclonal antibodies as disclosed in the present application.

The antibodies of the present invention, preferably a chAZ158-like antibody, may also be derivatized to "chimeric" antibodies (immunoglobulins) in which a portion of the heavy light chain is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. U.S.A., pp. 6851 (1984)).

Other derivatives within the scope of this invention include functionalized antibodies, i.e., antibodies that are conjugated or covalently bound to a toxin, such as ricin, diphtheria toxin, abrin and *Pseudomonas* exotoxin; to a detectable moiety, such as a fluorescent moiety, a radioisotope or an imaging agent; or to a solid support, such as agarose beads or the like. Methods for conjugation or covalent bonding of these other agents to antibodies are well known in the art.

Conjugation to a toxin is useful for targeted killing cells displaying KIR3DL receptors on its cell surface, e.g. malignant T cells. Once the antibody of the invention binds to the cell surface of such cells, it is internalized and the toxin is released inside of the cell, selectively killing that cell.

Conjugation to a detectable moiety is useful, inter alia, when an antibody of the invention is used for diagnostic purposes. Such purposes include, but are not limited to, assaying biological samples, e.g., a blood sample or tissue biopsy, for the presence of KIR3DL-expressing cells, and detecting the presence, level, or activity of KIR3DL-expressing cells in an individual. Such assay and detection methods are also alternate embodiments of the present invention. Such method are useful, e.g., for diagnosing conditions caused by or associated with an increase in KIR3DL-expressing cell activity or number. Labeled antibodies of the invention can also be used in FACS sorting to purify or isolate KIR3DL-expressing cells from a biological sample.

Conjugation of an antibody of this invention to a solid support is useful as a tool for affinity purification of cells bearing a KIR3DL on their cell surface from a biological sample, such as a blood sample or mucosal tissue biopsy from an individual. This method of purification is another alternate embodiment of the present invention, as is the resulting purified population of cells.

In an alternate embodiment, an antibody that binds an epitope of a KIR3DL2 polypeptide, wherein said antibody is capable of modulating T cell activity, may be incorporated into liposomes ("immunoliposomes"), alone or together with another substance for targeted delivery to an animal. Such other substances include, but are not limited to, nucleic acids for the delivery of genes for gene therapy or for the delivery of antisense RNA, or siRNA for suppressing a gene in a T cell, or toxins or drugs for the targeted killing of cells.

Structural Properties of Recombinant AZ158 Antibodies

In one preferred embodiment, the antibody of the invention is a chimeric or humanized IgG antibody prepared using the variable domain sequences (e.g. the entire variable domain, a portion thereof, or part or all of the CDRs) of the chAZ158 antibody (or another antibody that binds to the same epitope as chAZ158). Preferred antibodies of the invention are the bivalent monoclonal antibodies comprising the variable region or CDRs of chAZ158 as produced, isolated, and structurally and functionally characterized and described herein. In one example the antibody is a chimeric bivalent antibody derived from AZ158, comprising a heavy chain variable region comprising SEQ ID NO 8 and a light chain variable region comprising SEQ ID NO 10 (chAZ158), described herein in the section titled Examples; in another example, the antibody is the alternative bivalent chimeric antibody made of the (two) heavy chain(s) comprising the heavy chain variable region of chAZ158 fused to a human IgG1 constant region and the (two) light chain(s) comprising the light chain variable region of chAZ158 fused to a human IgL Kappa constant region. Full-length, variable, and CDR sequences of these antibodies are set forth in Table 1. Additional sequences include the AZ158 VH region DNA (SEQ ID NO 7), AZ158 VL region DNA (SEQ ID NO 9), Leader-VH-AZ158-HuIgG1 DNA (SEQ ID NO 17) and Leader-VL-AZ158-HuIgL Kappa DNA (SEQ ID NO 19).

TABLE 1

| Antibody portion | SEQ ID NO: | Sequence | | | |
|---|---|---|---|---|---|
| AZ158 VH region amino acid | 8 | QVQLKESGPG PGKGLEWLGV KMNSLQNDDT VSS | LVAPSQSLSI IWAGGSTNYN AMYYCARGNS | TCTVSGFSLT SALMSRLSIS NHYVSSFYYF | SFGVHWVRQP KDNSKSQVFL DYWGQGTTLT |
| AZ158 VL region amino acid | 10 | DIQMTQSPSS GKGPRLLIHY EDITTYYCLQ | LSASLGGKVT TSTLQPGIPS YDNLWTFGGG | ITCKASQDIN RFSGSGSGRD TKLEIK | KYIAWYQHKP YSFSISNLEP |
| AZ158 VH CDR1 amino acid | 11 | GFSLTSFGVH | | | |
| AZ158 VH CDR2 amino acid | 12 | VIWAGGSTNYNSALMS | | | |
| AZ158 VH CDR3 amino acid | 13 | GNSNHYVSSFYYFDY | | | |

TABLE 1 -continued

| Antibody portion | SEQ ID NO: | Sequence |
|---|---|---|
| AZ158 VL CDR1 amino acid | 14 | KASQDINKYIA |
| AZ158 VL CDR2 amino acid | 15 | YTSTLQP |
| AZ158 VL CDR3 amino acid | 16 | LQYDNLWT |
| Leader-VH-AZ158-HuIgG1 amino acid | 18 | MAVLVLFLCL VAFPSCVLSQ VQLKESGPGL VAPSQSLSIT CTVSGFSLTS FGVHWVRQPP GKGLEWLGVI WAGGSTNYNS ALMSRLSISK DNSKSQVFLK MNSLQNDDTA MYYCARGNSN HYVSSFYYFD YWGQGTTLTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| Leader-VL-AZ158-HuIgL Kappa amino acid | 20 | MRPSIQFLGL LLFWLHGAQC DIQMTQSPSS LSASLGGKVT ITCKASQDIN KYIAWYQHKP GKGPRLLIHY TSTLQPGIPS RFSGSGSGRD YSFSISNLEP EDITTYYCLQ YDNLWTFGGG TKLEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |

Accordingly, in one aspect, the invention provides an isolated monoclonal antibody, or antigen binding portion thereof, comprising: (a) a VH region comprising an amino acid sequence selected from the group consisting of SEQ ID NOs: 8 and 11-13, and (b) a VL region comprising an amino acid sequence selected from the group consisting of SEQ ID NOs: 10 and 14-16; wherein the antibody specifically binds a KIR3DL2 polypeptide, preferably wherein the antibody specifically binds a common determinant on KIR3DL1, KIR3DL2 and KIR3DS1. Preferred heavy and light chain combinations include: (a) a heavy chain comprising the amino acid sequence of SEQ ID NO: 8 and (b) a light chain comprising the amino acid sequence of SEQ ID NO: 10; (a) a heavy chain comprising the amino acid sequence of amino acid positions 20 to 472 of SEQ ID NO: 18 and (b) a light chain comprising the amino acid sequence of amino acid positions 21 to 233 of SEQ ID NO: 20; (a) a heavy chain comprising the three CDRs having amino acid sequence of SEQ ID NOS: 11-13, or at least 3, 4, 5, 6, 7 or 8 contiguous amino acid residues thereof and (b) a light chain comprising the three CDRs having amino acid sequence of SEQ ID NOS: 14-16, or at least 3, 4, 5, 6, 7 or 8 contiguous amino acid residues thereof.

In another aspect, the invention provides heavy chain and light immunoglobulin chains that comprise the CDR1s, CDR2s and/or CDR3s of the respective heavy and light chains of chAZ158, or combinations thereof, and antibodies that comprise such heavy and/or light chains. The CDR regions are delineated using the Kabat system (Kabat et al. (1991) Sequences of Proteins of Immunological Interest, Fifth Edition, U.S. Department of Health and Human Services, NIH Publication No. 91-3242). The heavy chain CDRs of chAZ158 are located at amino acids positions 26 to 35 (CDR1), positions 50 to 65 (CDR2) and positions 98 to 112 (CDR3) in SEQ ID NO: 8. The light chain CDRs of chAZ158 are located at amino acids positions 24 to 34 (CDR1), positions 50 to 56, optionally 51 to 56, optionally 51 to 57 (CDR2) and positions 89 to 96 (CDR3) in SEQ ID NO: 10. The respective CDRs are also provided in SEQ ID NOS 11-16. Also encompassed, for each of the heavy and light chains, are CDR sequences comprising at least 3, 4, 5, 6, 7 or 8 contiguous amino acid residues of any the foregoing amino acid positions in the CDRs 1, 2 and 3. Also encompassed, for each of the heavy and light chains, are CDR sequences having at least 50%, 60%, 70%, 80% or 90% sequence identity of any the foregoing amino acid positions in the CDRs 1, 2 and 3. In one aspect, the invention provides a humanized antibody heavy or light chain comprising antigen-binding residues from the CDRs of antibody AZ158, e.g. the three CDRs for each of the heavy and light chains of AZ158, in a human acceptor framework, wherein each CDR comprises at least 3, 4, 5, 6, 7 or 8 contiguous amino acid residues of the respective CDR1s, CDR2s and/or CDR3s of the respective heavy or light chain of AZ158. Optionally, one, two, three or more amino acid residue of any one or more of said CDRs are the same as those in the human acceptor sequence.

Accordingly, in another aspect, the invention provides an immunoglobulin heavy chain, or antigen binding portion thereof comprising: (a) a VH CDR1 comprising an amino acid sequence of SEQ ID NO: 11; (b) a VH CDR2 comprising an amino acid sequence of SEQ ID NO: 12; and (c) a VH CDR3 comprising an amino acid sequence of SEQ ID NO: 13. In another aspect, the invention provides an immunoglobulin light chain, or antigen binding portion thereof comprising (a) a VL CDR1 comprising an amino acid sequence of SEQ ID NO: 14; (b) a VL CDR2 comprising an amino acid sequence of SEQ ID NO:15; and (c) a VL CDR3 comprising an amino acid sequence of SEQ ID NO: 16. Preferably said heavy chain comprises a heavy chain variable region comprising VH CDR1, VH CDR2 and VH CDR3 fused to a human IgG chain constant region. Preferably said light chain variable region comprising VL CDR1, VH CDR2 and VH CDR3 fused to human kappa chain constant region. Preferably said human IgG chain constant region is an IgG1 isotope.

Also provided is an antibody that is a tetramer comprising two of said heavy chains and two of said light chains.

In one aspect, the invention provides an isolated monoclonal antibody, or antigen binding portion thereof, comprising: (a) a VH region described herein (e.g. a variable region, portion thereof, or a variable region comprising VH CDR1, CDR2 and/or CDR3 described herein) fused to a human IgG chain constant region, and (b) a VL region described herein (i.e. a variable region, portion thereof, or a variable region comprising VH CDR1, CDR2 and/or CDR3 described herein) fused to human kappa chain constant region; wherein the antibody specifically binds a KIR3DL2 polypeptide.

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-KIR3DL2 antibodies of the invention. Optionally, the VH domain comprises amino acid modifications of one or more CDR residues, e.g. where the modifications essentially maintain or improve affinity of the antibody. For example, the antibody variant may have one, two, three, or from one to about seven amino acid substitutions in the above VH or VL CDR sequences. For example, the invention provides an isolated monoclonal antibody, or antigen binding portion thereof, comprising a heavy chain variable region and a light chain variable region, wherein: (a) the VH region comprises an amino acid sequence that is at least 50%, 60%, 70%, 80% or 90% identical to an amino acid sequence selected from the group consisting of SEQ ID NOs: 8 and 11-13; (b) the VL region comprises an amino acid sequence that is at least 50%, 60%, 70%, 80% or 90% identical to an amino acid sequence selected from the group consisting of SEQ ID NOs: 10 and 14-16; (c) the antibody specifically binds to a KIR3DL2 polypeptide and exhibits at least one of the functional properties described herein, preferably several of the functional properties described herein.

In other embodiments, the CDR, VH and/or VL, or constant region amino acid sequences may be 50%, 60%, 70%, 80%, 85%, 90%, 95%, 96%, 97%, 98% or 99% identical to the sequences set forth above. An antibody having CDR, VH and/or VL regions having high (i.e., 80% or greater) identity to the CDR, VH and/or VL, or constant region regions of the sequences set forth above, can be obtained by mutagenesis (e.g., site-directed or PCR-mediated mutagenesis) of nucleic acid molecules encoding the CDR, VH and/or VL of SEQ ID NOs: 6 to 16, followed by testing of the encoded altered antibody for retained function (e.g., KIR3DL2 binding affinity, slowing proliferation of KIR3DL2-expressing cells, induction of ADCC).

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm in a sequence analysis software. Protein analysis software matches similar sequences using measures of similarity assigned to various substitutions, deletions and other modifications, including conservative amino acid substitutions.

The percent identity between two amino acid sequences can be determined, e.g., using the Needleman and Wunsch (J. Mol. Biol. 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183: 63-98; Pearson, Methods Mol. Biol. 2000; 132:185-219). The percent identity between two amino acid sequences can also be determined using the algorithm of E. Meyers and W. Miller (Comput. Appl. Biosci., 1988; 11-17) which has been incorporated into the ALIGN program (version 2.0), using a PAM120 weight residue table, a gap length penalty of 12 and a gap penalty of 4.

Another algorithm for comparing a sequence to other sequences contained in a database is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. The protein sequences of the present invention can there be used as a "query sequence" to perform a search against public databases to, for example, identify related sequences. Such searches can be performed using the XBLAST program (version 2.0) of Altschul, et al. 1990 (supra). BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 (supra). When utilizing BLAST and Gapped BLAST programs, the default parameters of the respective programs (e.g., XBLAST and NBLAST) can be used. See http://www.ncbi.nlm.nih.gov.

In certain embodiments, an antibody of the invention comprises a VH region comprising CDR1, CDR2 and CDR3 sequences and a VL region comprising CDR1, CDR2 and CDR3 sequences, wherein one or more of these CDR or variable region sequences comprise specified amino acid sequences based on the preferred antibodies described herein (e.g. chAZ158 and any of SEQ ID NOs 6-16), or conservative modifications thereof, and wherein the antibodies retain the desired functional properties of the anti-KIR3DL2 antibodies of the invention. Conservative sequence modifications can be any amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. "Conservative" amino acid substitutions are typically those in which an amino acid residue is replaced with an amino acid residue having a side chain with similar physicochemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c), (d) and (e) above) using the functional assays described herein.

The nucleic acid sequences encoding the chAZ158 antibody heavy chain and light chain variable regions are shown in SEQ ID NOS 7 and 9, respectively. In one embodiment the invention provides a bivalent monoclonal antibody that comprises the variable heavy chain region of AZ158 transcribed and translated from a nucleotide sequence comprising SEQ ID NO 7 or a fragment thereof (e.g. a sequence encoding CDR1, CDR2 and/or CDR3 of chAZ158 VH region), and the variable light chain region of chAZ158 transcribed and translated from a nucleotide sequence comprising SEQ ID NO 9 or a fragment thereof (e.g. a sequence encoding CDR1, CDR2 and/or CDR3 of the chAZ158 VL region Hypofucosylated Constant Regions In view of the ability of the anti-KIR3DL2 antibodies of the invention to induce ADCC when produced in cells yielding hypofucosylated antibodies, the antibodies of the invention can also be made with modifications that increase their ability to bind Fc receptors. Typical modifications include modified human IgG1 constant regions comprising at least one amino acid modification (e.g. substitution, deletions, insertions), and/or altered types of glycosylation, e.g., hypofucosylation. Such modifications can for example increase binding to FcγRIIIa on effector (e.g. NK) cells.

Certain altered glycosylation patterns in constant regions have been demonstrated to increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety.

Generally, such antibodies with altered glycosylation are "glyco-optimized" such that the antibody has a particular N-glycan structure that produces certain desirable properties, including but not limited to, enhanced ADCC and effector cell receptor binding activity when compared to non-modified antibodies or antibodies having a naturally occurring constant region and produced by murine myeloma NS0 and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennnary structures with very low or no bisecting N-acetyl-glucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trend Biotechnol. 15:26-31(1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

FcγR binding requires the presence of oligosaccharides covalently attached at the conserved Asn297 in the Fc region of human IgG1, IgG2 or IgG3 type. Non-fucosylated oligosaccharides structures have recently been associated with dramatically increased in vitro ADCC activity. "Asn 297" according to the invention means amino acid asparagine located at about position 297 in the Fc region; based on minor sequence variations of antibodies, Asn297 can also be located some amino acids (usually not more than +3 amino acids) upstream or downstream.

Historically, antibodies produced in CHO cells contain about 2 to 6% in the population that are nonfucosylated. YB2/0 (rat myeloma) and Lec13 cell line (a lectin mutant of CHO line which has a deficient GDP-mannose 4,6-dehydratase leading to the deficiency of GDP-fucose or GDP sugar intermediates that are the substrate of alpha6-fucosyltransferase have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

The invention comprises an antibody binding to KIR3DL2 being glycosylated with a sugar chain at Asn297, said antibody showing increased binding affinity via its Fc portion to FcγRIII. In one embodiment of the invention, an antibody will comprise a constant region comprising at least one amino acid alteration in the Fc region that improves antibody binding to FcγRIIIa and/or ADCC.

In one aspect, the antibodies of the invention are hypofucosylated in their constant region. Such antibodies may comprise an amino acid alteration or may not comprise an amino acid alteration but be produced or treated under conditions so as to yield such hypofucosylation. In one aspect, an antibody composition of the invention comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

In one embodiment, the invention comprises an antibody composition of the invention, e.g. a composition comprising antibodies which bind to KIR3DL2, are glycosylated with a sugar chain at Asn297, wherein the antibodies are partially fucosylated. Partially fucosylated antibodies are characterized in that the proportion of anti-KIR3DL2 antibodies in the composition that lack fucose within the sugar chain at Asn297 is between 20% and 90%, preferably between 20% and 80%, preferably between 20% and 50%, 55%, 60%, 70% or 75%, between 35% and 50%, 55%, 60%, 70% or 75%, or between 45% and 50%, 55%, 60%, 70% or 75%. Preferably the antibody is of human IgG1 or IgG3 type.

The sugar chain show can further show any characteristics (e.g. presence and proportion of complex, hybrid and high mannose structures), including the characteristics of N-linked glycans attached to Asn297 of an antibody from a human cell, or of an antibody recombinantly expressed in a rodent cell, murine cell (e.g. CHO cell) or in an avian cell (e.g. EBx® cell)

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al.; and Yamane-Ohnuki et al. (2004) Biotechnol Bioeng 87:614-22, the disclosures of which are incorporated herein by reference). Other examples have included use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotem-modifying glycosyl transferases (e.g., beta(1,4)-N-acetylglucosaminyltransferase III (GnTHI)) such that antibodies expressed in the engineered cell lines exhibit increased bisecting GlcNac structures which results in increased ADCC activity of the antibodies (PCT Publication WO 99/54342 by Umana et al.; and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino, et al. (1975) Biochem. 14:5516-5523). In other examples, a cell line producing an antibody can be treated with a glycosylation inhibitor; Zhou et al. Biotech. and Bioengin. 99: 652-665 (2008) described treatment of CHO cells with the alpha-mannosidase I inhibitor, kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Hypofucosylated glycans can also be produced in cell lines of plant origin, e.g. WO 07/084,926A2 (Biolex Inc.), WO 08/006,554 (Greenovation Biotech GMBH), the disclosures of which are incorporated herein by reference. Other example of cell lines include a variant CHO cell line, Led 3 cells, with reduced ability to attach fucosyl to Asn(297)-linked carbohydrates, also resulting in hypofucosylation of antibodies expressed in that host cell (WO 03/035835 (Presta et al); and Shields, R X. et al. (2002) J. Biol. Chem. 277:26733-26740, the disclosures of which are incorporated herein by reference).

In another embodiment, the antibody is expressed in an avian cell, preferably a cell line which naturally yields antibodies with low fucose content, e.g., WO2008/142124 (Vivalis SA). As demonstrated herein, use of an avian embryonic derived stem cell line EBx® (e.g., EB66 or EB14) yields a large proportion of IgG1 antibodies having a common N-linked biantennary-type oligosaccharide structure that comprises long chains with terminal GlcNac that are highly galactosylated. Approximately half of IgG1 antibodies population contains the N-linked non-fucosylated biantennary-type oligosaccharide structure. The invention thus encompasses methods of producing antibodies, and antibodies produced using such methods, where methods for producing the antibodies comprise expressing the antibody in an avian embryonic derived stem cell EBx®, preferably chicken or duck embryonic derived stem cell (e.g., EBx®) and more preferably chicken EB14 cells or duck EB24 and EB66 cells, genetically engineered to express recombinant anti-KIR3DL antibody.

Avian embryonic cell lines have been generated by several different investigators. For example, U.S. Pat. No. 5,340,740 describes the development of avian embryonic stem cells by culturing avian blastodermal cells in the presence of a mouse fibroblast feeder layer. U.S. Pat. No. 5,656,479 and WO 93/23528 also describe an avian cell culture of undifferentiated avian cells expressing an embryonic stem cell phenotype. U.S. Pat. No. 6,114,168 and WO 96/12793 describe methods for producing avian embryonic stem cells on CEFs using particular media. U.S. Pat. No. 6,280,970 describes transformed avian embryonic fibroblasts that contain SV40 T Ag within their genome. US patent publication no. 2001/0019840A1 describes culture media for producing avian ES cells and methods for producing proteins in ES cells cultured in such medium. WO 00/47717 describes the processes for developing avian embryonic germ cell lines by culturing avian primordial germ cells in culture medium containing particular growth factors and differentiation inhibitory factors. In certain embodiments, such cells include, for example, EB1, EB2, EB3, EB4, EB5, and EB14 cells, obtainable from VIVALIS SA (Nantes, France) and described in FR02/02945, WO 03/07661 and WO2008/129058. These cells were obtained from chick or duck embryos at very early steps of embryogenesis and exhibit a stem cell phenotype. The cells are not genetically modified in their native state and grow up to high cell density in suspension in an animal serum free cell culture medium.

In a preferred embodiment, the avian cell of the present invention is a chicken or duck cell. EBx® cells have been generated using a fully documented two-step process, described along with more general methods for obtaining and preparing avian cells for production of an antibody, are described in U.S. patent application No. 61/032,786, filed Feb. 29, 2008 and International patent publication no. WO2008/142124, filed May 21, 2008 the disclosures of which are incorporated herein by reference.

Examples of chicken EBx® cell lines include suspension chicken cell lines EB14 (see WO 03/076601 and WO05/007840) or EBv13. Examples of duck EBx® cell lines include EB24, EB26, EB66. The term "avian, "bird", "ayes" or "ava" as used herein is intended to have the same meaning, and will be used indistinctly. "Birds" refer to any species, subspecies or race of organism of the taxonomic class "ava". In a preferred embodiment, "birds" refer to any animal of the taxonomic order:—"Anseriformes" (i.e., duck, goose, swan and allies). According to a more preferred embodiment, the bird is a duck, more preferably a Pekin or Moscovy duck. Therefore, the instant invention provides a process for obtaining continuous diploid duck cell lines derived from embryonic stem cells (ES), wherein said duck cell lines do not produce replication competent endogenous retrovirus particles. Example of duck EBx® cell lines of the invention are EB24, EB26, EB66 or their subclones thereof, such as EB24-12.

The process of establishment of continuous diploid avian cell lines, named EBx®, of the invention generally comprises two steps: a) isolation, culture and expansion of embryonic stem (ES) cells from birds that do not contain complete endogenous proviral sequences, or a fragment thereof, susceptible to produce replication competent endogenous retroviral particles, more specifically EAV and/or ALV-E proviral sequences or a fragment thereof, in a complete culture medium containing all the factors allowing their growth and in presence of a feeder layer and supplemented with animal serum; optionally, said complete culture medium may comprise additives, such as additional amino-acids (i.e glutamine, . . . ), sodium pyruvate, betamercaptoethanol, protein hydrolyzate of non-animal origin (i.e yeastolate, plant hydrolyzates, . . . ); b) passage by modifying the culture medium so as to obtain a total withdrawal of said factors, said feeder layer and said serum, and optionally said additives, and further obtaining adherent or suspension avian cell lines, named EBx®, that do not produce replication-competent endogenous retrovirus particles, capable of proliferating over a long period of time, in a basal medium in the absence of exogenous growth factors, feeder layer and animal serum. As will be appreciated by those skilled in the art, the selection of the appropriate vector, e.g., plasmid, components for proper transcription, expression (promoter, control sequences and regulatory sequence), and isolation of proteins produced in cell expression systems is known and routinely determined and practiced by those having skill in the art.

The EBx® cells are typically transfected with at least one expression vector wherein said expression vector comprises at least in the following order:
  a first expression cassette comprising the following DNA sequences in the following order: promoter sequence (e.g. CMV promoter), intronic sequence, DNA sequence (preferably cDNA sequence) encoding the heavy chain of an antibody or a fragment thereof, polyadenylation sequence;
  a second expression cassette comprising the following DNA sequences in the following order: promoter sequence (e.g. CMV promoter), intronic sequence, DNA sequence (preferably cDNA sequence) encoding the light chain of the antibody or a fragment thereof, polyadenylation sequence;
  a third expression cassette comprising the following DNA sequences in the following order: viral promoter, antibiotic resistance gene, polyadenylation sequence, (e.g. SV40 promoter, neomycin resistance gene, polyadenylation sequence);
  optionally, at least one chicken lysozyme 5' MAR element as described in WO02/074969 or a human MAR elements as described in WO 2005/040377. The culturing of said transfected EBx® cells can be performed according to the cell culture techniques well-known by the man skilled in the art.

The antibodies of the invention, when expressed in EBx cells, display a common N-linked oligosaccharide structure of a biantennary-type that comprises long chains with terminal GlcNac that are highly galactosylated and non-fucosylated and which confer strong ADCC activity to antibodies. The proportion of non-fucosylated antibodies represent at least 20%, more preferably at least 35%, and more preferably at least 45%, 50% or 55% of the antibodies or higher. Therefore, the invention provides a recombinant polypeptide, produced by transfected EBx cell line, preferably EB14 or duck EB66 cell lines, wherein the recombinant polypeptide is characterized as having approximately 20%, more preferably approximately 35%, and even more preferably approximately 45% of non-fucosylated N-linked oligosaccharides structures. More precisely, the invention provides a recombinant monoclonal antibody that binds KIR3DL according to any of the embodiments of the present disclosure, produced by a transfected EBx cell line, preferably a duck EB66 cell line, wherein said antibody is characterized as having approximately 45% or more of non-fucosylated N-linked oligosaccharides structures. Said antibody can be characterized as having approximately 35% or more of non-fucosylated N-linked oligosaccharides structures G0, G1 and G2. The invention also relates to an antibody that binds KIR3DL or population of such antibodies, produced in EBx® cell, preferably in duck EB66 cell, and having increased ADCC activity compared to the same antibody produced in hydridoma or wild-type CHO cell line, preferably CHOK1 and CHO-DG44. The anti-KIR3DL antibody population produced in EBx® cells can also be characterized as comprising a large proportion of antibodies wherein the Fc region carry a common N-linked fucosylated oligosaccharide structure of a biantennary-type that comprises long chains with terminal GlcNac that are galactosylated and a large proportion of antibodies wherein the Fc region carry a common N-linked non-fucosylated oligosaccharide structure of a biantennary-type that comprises long chains with terminal GlcNac that are galactosylated. The antibody population is characterized by having approximately 45% of non-fucosylated N-linked oligosaccharides structures. Most of these antibodies, that is to say, more than 60%, 75%, 85%, or 95% of these antibodies of the antibody population produced in EBx cells do not contain sialic acid residues on the N-linked oligosaccharide structure of a biantennary-type that is linked to Fc region. A large proportion of sialic acid residues are N-acetyl-neuraminic acid (NeuAC)—typically more than 80%, 90%, or 95% of sialic acid residues are NeuAc which are known to be non-immunogenic in human. The remaining small proportion of sialic acid residues is composed of N-glycolylneuraminic acid (NeuGc).

While antibodies in underivatized or unmodified form are preferred, particularly of the IgG1 or IgG3 type, or underivatived antibodies comprising a modification in the constant region to improve antibody binding to FcγRIIIa and/or ADCC, it is also possible to prepare derivatized antibodies to make them cytotoxic. When bivalent IgG forms of such derivatived antibodies are used, they can thus target tumor cells in two distinct ways: by ADCC (e.g. when the antibodies bind Fc receptors, for example via their constant regions) and by killing the cell via the cytotoxic moiety. In one embodiment, once the antibodies are isolated and rendered suitable for use in humans, they are derivatized to make them toxic to cells. In this way, administration of the antibody to e.g. CTCL patients will lead to the relatively specific binding of the antibody to KIR3DL2 polypeptide-expressing cancer cells, thereby providing an additional means for directly killing or inhibiting the cells.

Purifying KIR3D Positive Cells Using the Antibodies of the Invention

In certain embodiments, the present antibodies are used to purify KIR3D positive cells from a biological sample. Biological samples can be obtained from a patient, e.g. for diagnostic or ex vivo therapeutic purposes, or from individuals or non-human primates to obtain a source of such cells for research purposes.

KIR3D positive cells can be purified using the present antibodies with any of a number of standard methods. For example, peripheral blood cells can be sorted using a FACS scanner using labeled antibodies specific for KIR3DL2, and optionally to other cell surface molecules typically present on cells, e.g., CD4 for T cells; CD4 CD2+, CD3+, CD5+, CD8−, CD28+, CD45RO+ and/or TCRαβ+ for malignant cells in Sezary Syndrome; CD4+ and CD28− in inflammatory, autoimmune or cardiovascular diseases.

In addition, the antibodies of the invention can be conjugated or covalently linked to a solid support and used to purify KIR3D positive cells or any cells expressing KIR3D from a biological sample, e.g., from a blood sample or mucosal tissue biopsy from a patient or other individual. Specifically, the biological sample is placed into contact with the antibodies under conditions that allow cells within the sample to bind to the antibody, and then the cells are eluted from the solid-support-bound antibody.

Regardless of the method used to isolate or purify the KIR3D positive cells, the ability to do so is useful for numerous purposes, e.g. to diagnose a disorder characterized by a pathogenic expansion of KIR3D-expressing cells, by assessing the number or activity or other characteristics of KIR3D positive cells obtained from a patient, or to evaluate the ability of the antibodies of the invention, or fragments or derivatives thereof, to modulate the activity or behavior of the cells of a patient prior, e.g., to one of the herein-described treatments using the antibodies. Further, purified KIR3D positive cells are useful in a research context, e.g., to better characterize the cells and their various properties and behaviors, as well as to identify compounds or methods that can be used to modulate their behavior, activity, or proliferation. The antibodies of the invention can also be useful in diagnostic methods, for example in methods of detecting KIR polypeptides on cells, e.g., disease cells from a patient. The antibodies that bind all KIR3D polypeptides (KIR3DL1, DL2 and DS1) provide a method to detect all expressed KIR3D polypeptides with a single antibody, and furthermore to distinguish KIR3D from KIR2D polypeptides. The KIR3D antibodies can optionally be used in combination with KIR2D antibodies where the entire range of KIR polypeptides is to be assessed.

Treatment of Disease

The present invention also provides pharmaceutical compositions that comprise an antibody according to the invention which specifically binds to KIR3DL2 polypeptides on the surface of cells, and inhibits the growth or activity of the cells and/or leads to the elimination, preferably via ADCC, of the KIR3DL positive cells. The composition further comprises a pharmaceutically acceptable carrier.

The invention further provides a method of inhibiting the growth or activity of, and/or depleting, KIR3DL-positive cells, particularly KIR3DL2-positive cells, in a patient in need thereof, comprising the step of administering to said patient a composition according to the invention. Such treatment methods can be used for a number of disorders, including, but not limited to CTCL, SS and MF, inflammatory, autoimmune and cardiovascular disorders.

In some embodiments, prior to the administration of the anti-KIR3DL2 antibody or composition, the presence of KIR3DL (e.g. KIR3DL2) on cells of the patient will be assessed, e.g., to determine the relative level and activity of KIR3LD-positive cells in the patient as well as to confirm the binding efficacy of the antibodies to the cells of the patient. This can be accomplished by obtaining a sample of PBLs or cells from the site of the disorder, and testing e.g., using immunoassays, to determine the relative prominence of markers such as CD4, etc., as well as e.g. KIR3DL2 on the cells.

In one embodiment, where it is sought to inhibit the activity or growth of, or deplete, a patient's KIR3DL-positive cells, the ability of the anti-KIR3DL2 antibody to inhibit proliferation of or deplete a patient's KIR3DL-positive cells is assessed. If the KIR3DL-positive cells are inhibited and/or depleted by the anti-KIR3DL2 antibody or composition, the patient is determined to be responsive to therapy with an anti-KIR3DL2 antibody or composition, and optionally the patient is treated with an anti-KIR3DL2 antibody or composition.

In other embodiments, the method may comprise the additional step of administering to said patient an appropriate additional therapeutic agent selected from an immunomodulatory agent, an immunosuppressive agent, a hormonal agent, a chemotherapeutic agent, a second antibody that binds to a KIR3DL2 polypeptide. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

Mycosis fungoides and the more aggressive Sézary syndrome represent the most common forms of CTCL. The clinical course of MF/SS is usually indolent, with pruritic erythematous areas slowly developing over long periods. Eventually, however, the erythematous patches become progressively infiltrated, developing into plaques and finally to ulcerating tumors. The prognosis of MF/SS is based on the extent of disease at presentation. Patients with stage I disease have a median survival of 20 years or more, in comparison with a median survival of approximately 3 to 4 years for patients with stage III/IV disease.

The compositions of the invention can be used for treatment in combination with any agent known to be useful in the treatment of the particular T cell malignancy. Although there is no current standard of care for MF/SS, there is a general tendency to rely on topical interventions for early disease delaying systemic and more toxic therapy until the development of extensive symptoms. Psoralen and ultraviolet A radiation (PUVA), combined or not with low doses of interferon-$\alpha$, is effective in early-stage MF/SS, inducing complete remission (CR) in most patients. Local radiotherapy or total-skin electron-beam irradiation (TSEB) has been used with success to control advanced skin disease. Extra corporeal photopheresis may also be used successfully but is not generally available. Once the disease becomes refractory to topical therapy, interferon-$\alpha$, the rexinoid bexarotene (Targretin®, Ligand Pharmaceuticals, San Diego, Calif.), a synthetic retinoid analog targeting the retinoid X receptor, single-agent chemotherapy or combination chemotherapy may be given. The duration of response is however often less than 1 year, and ultimately all patients have relapses and the disease becomes refractory. The recombinant IL2-diphteria toxin denileukin diftitox (DAB389IL-2, ONTAK®, Ligand Pharmaceuticals, San Diego, Calif.) is active in patients with stage Ib to stage IV CTCL refractory to previous treatments (overall objective response in 30% of 71 patients with a median duration response of 7 months) and appears to have a beneficial effect in symptoms relief and quality of life. More recently, denileukin diftitox have been tested in a Phase I trial in combination with bexarotene, since it induces CD25 up regulation in vitro. The combination was well tolerated and induced objective response in 67% of 14 patients. The most significant adverse events were those already reported with bexarotene alone (hypertriglyceridemia and suppression of thyroid function due to decreased TSH production) and grade 3 or 4 lymphopenia but resolving within one month of cessation of therapy. The time to treatment failure was not reported in this study. In other studies, a chimeric monoclonal anti- CD4 (cM-T412, Centocor, Malvern, Pa.) was administered to 8 patients with MF and induced objective response in 7 of them but with a median response duration of only 5 months. Uvadex® (methoxsalen, Therakos Inc. Exton, Pa.) in extra corporal photopheresis, has also shown signs of efficacy. The humanized monoclonal antibody alemtuzumab (hu-IgG$_1$ anti-CD52 mAb, Campath®, Millennium Pharmaceuticals, Inc. and ILEX Oncology, Inc., marketed and distributed in the US by Berlex Laboratories, Inc., Montville, N.J.) is indicated for the treatment of B-cell chronic lymphocytic leukemia (B-CLL) in patients who have been treated with alkylating agents and who have failed fludarabine therapy. It has been tested in patients with advanced MF/SS (stage III or IV disease) and led to objective responses in at least half of cases (55% of 22 patients). Its side effect profile consists mainly of immunosuppression and infusion reactions. An independent retrospective study described also significant cardiac toxicity in 4 out of 8 patients. With long lasting remissions observed (median time to treatment failure 12 months, range 5 to 32+ months), alemtuzumab therapy appears to be the treatment with the more favorable median response duration compared to all treatments reported to date. Each of these treatments can be used in combination with the antibodies of the invention.

The antibodies produced using the present methods are particularly effective at treating autoimmune and inflammatory disorders, as well as cardiovascular disorders most particularly acute coronary syndrome, arthritis, rheumatoid arthritis, rheumatoid vascularitis, systemic lupus erythematosus, multiple sclerosis and Wegener's granulomatosus, spondylarthritis. In general, the present methods can be used to treat any disorder caused at least in part by the presence or activity of KIR3DL-expressing cells, e.g., T cells such as CD4$^+$CD28$^-$ cells expressing KIR3DL2, and which can therefore be effectively treated by selectively killing or inhibiting the proliferation or activation of KIR3DL2-expressing cells, e.g., by activating KIR3DL2 so as to transmit an inhibitory intracellular signal.

In some embodiments, prior to the administration of the anti-KIR3DL2 antibody, the expression of KIR3DL on cells underlying the particular disorder will be assessed. This can be accomplished by obtaining a sample of PBLs or cells from the site of the disorder (e.g., from the synovium in RA patients), and testing e.g., using immunoassays, to determine the relative prominence of markers such as CD4, CD28, etc., as well as KIR3DL on the cells. Other methods can also be used to detect expression of KIR3DL and other genes, such as RNA-based methods, e.g., RT-PCR or Northern blotting.

The treatment may involve multiple rounds of antibody or compound administration. For example, following an initial round of administration, the level and/or activity of KIR3DL-expressing T cells, e.g., CD4$^+$CD28$^-$ T cells, malignant CD4+ T cells, in the patient will generally be re-measured, and, if still elevated, an additional round of administration can be performed. In this way, multiple rounds of receptor detection and antibody or compound administration can be performed, e.g., until the disorder is brought under control.

The anti-KIR3DL2 antibodies of the invention can be used for treatment in combination with any agent known to be useful in the treatment of the particular inflammatory disorder, autoimmune disorder, or cardiovascular disorder. In view of the anti-KIR3DL2 antibodies' ability to inhibit cell proliferation in the absence of immune effector cells, it may be advantageous to administer KIR3DL2 antibodies in combination with an immunosuppressive treatment. Anti-KIR3DL2 antibodies can be combined for example with steroidal anti-inflammatory agents, non-steroidal anti-inflammatory agents, anti-metabolites and other agents used in treating cardiovascular, inflammatory or autoimmune diseases. In some embodiments, anti-inflammatory agents comprise steroidal anti-inflammatory agents, which include glucocorticosteroids and mineralocorticosteroids. These may be administered by any methods suitable for treating the inflammatory disorders, including, among others, oral, intravenous, intramuscular, dermal, or nasal routes. In some embodiments, the anti-inflammatory agents comprise non-steroidal anti-inflammatory agents. These agents generally act by inhibiting the action of cyclooxygenase and lipoxygenase enzymes, or receptors for mediators generated by these enzymes. The non-steroidal anti-inflammatory compounds include non-selective COX inhibitors, selective COX inhibitors, as well as FLAP antagonists and 5-lipoxygenase antagonists. In some embodiments, the anti-inflammatory agents can comprise anti-metabolites that affect proliferation of cells involved in the immune response. Suitable anti-metabolites include folate analogs, such as methotrexate; inosine monophosphate dehydrogenase (IMPDH) inhibitors, such as mycophenolate mofetil; and azathiopurine. Compounds of this group generally affect production of the substrates necessary for DNA replication, thereby inhibiting the proliferation of cells involved or activated in response to an inflammatory reaction. In some embodiments, the anti-inflammatory agent is an agent that blocks the action of TNF-alpha, the major cytokine implicated in inflammatory disorders. In some embodiments, the anti-TNF is an antibody that blocks the action of TNFalpha. An exemplary anti-TNF antibody is infliximab (Remicade®). In other embodiments, the anti-TNFalpha agent is a receptor construct that binds TNFalpha and prevents its interaction with TNF receptors on present on cells, e.g. entanercept (Enbrel®). In other embodiments, the anti-inflammatory agent is any other agent (e.g. an antibody agent) having immunosuppressive properties and useful in the treatment of the disorder being treated with the KIR3D antibody of the invention.

Pharmaceutical Compositions

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Several monoclonal antibodies have been shown to be efficient in clinical situations, such as Rituxan Herceptin (Trastuzumab) or Xolair (Omalizumab), and similar administration regimens (i.e., formulations and/or doses and/or administration protocols) may be used with the antibodies of this invention. Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 10 mg/m2 and 500 mg/m2. However, it will be appreciated that these schedules are exemplary and that an optimal schedule and regimen can be adapted taking into account the affinity and tolerability of the particular antibody in the pharmaceutical composition that must be determined in clinical trials.

Quantities and schedule of injection of an antibody in a pharmaceutical composition of this invention that saturate KIR3DL2-expressing cells for 24 hours, 48 hours, 72 hours, or a week or a month will be determined considering the affinity of the antibody and the its pharmacokinetic parameters.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of autoimmune disorders, inflammatory disorders or T cell lymphomas, e.g. SS or MF.

Further aspects and advantages of this invention will be disclosed in the following experimental section, which should be regarded as illustrative and not limiting the scope of this application.

EXAMPLES

Example 1

Generation of AZ158 mAbs were generated by immunizing 5 week old Balb C mice with polyclonal IL-2 activated NK population. After different cell fusions, the mAb AZ158 was initially selected for binding subset of NK cells population in different donors and two colour immunofluorescence analysis of polyclonal NK-cell populations indicated that AZ158 mAb reacts with the same cell subset stained by Z27 (anti KIR3DL1/S1) and Q66 (anti-KIR3DL2, IgM, generated in the inventors' laboratory) mAbs. The reactivity of AZ158 was further analyzed on NK cell populations and clones in combination with additional antibodies, including EB6 (anti-p58.2.p50.2, CD158a), GL183 (anti-p58.2/50.2, CD158b), PAX180 (anti-p50.3) and FES172 (anti-p50.3), as well as Z27 and Q66, and it was observed that AZ158 reacted with the same cell subset stained by the anti-KIR3DL1 and anti-KIR3DL2 mAbs. Similar results were also observed using a panel of NK cell clones expressing different HLA class I specific NK receptors.

Example 2

Binding to KIR3D Receptors

A. Binding to KIR3DS1 on PBMC

Binding of antibody AZ158 to human NK cells was assessed. PBMC (thawed and gated for CD3$^-$CD56$^+$ NK lymphocytes) were incubated with mAbs, washed and labeled with PE-GaM, SAV-PE or GAM-IgG M. Flow cytometry was carried out on a XL/MCL cytometer (Beckman Coulter). Acquisition and analysis are performed with EXPO™ 32 v1.2 software (Beckman Coulter). Antibodies used were AZ158, and Z27-PE (specific for KIR3DL1 and KIR3DS1), DX9-PE (specific for KIR3DL1 only) and Q66 (IgM specific for KIR3DL2 only), both previously generated in the inventors' laboratory). Including DX9 in addition to Z27 and Q66 permits the contribution of KIR3DS1 to the binding profile to be assessed. Staining patterns indicated that slightly more than half of NK cell population was stained by including AZ158. Based on staining patterns, antibody AZ158 appeared to stain each of the subsets of NK cells stained by antibodies Z27, Q66 and DX9 indicating that AZ158 binds each of KIR3DL1, KIR3DL2 and KIR3DS1.

Figure 4:
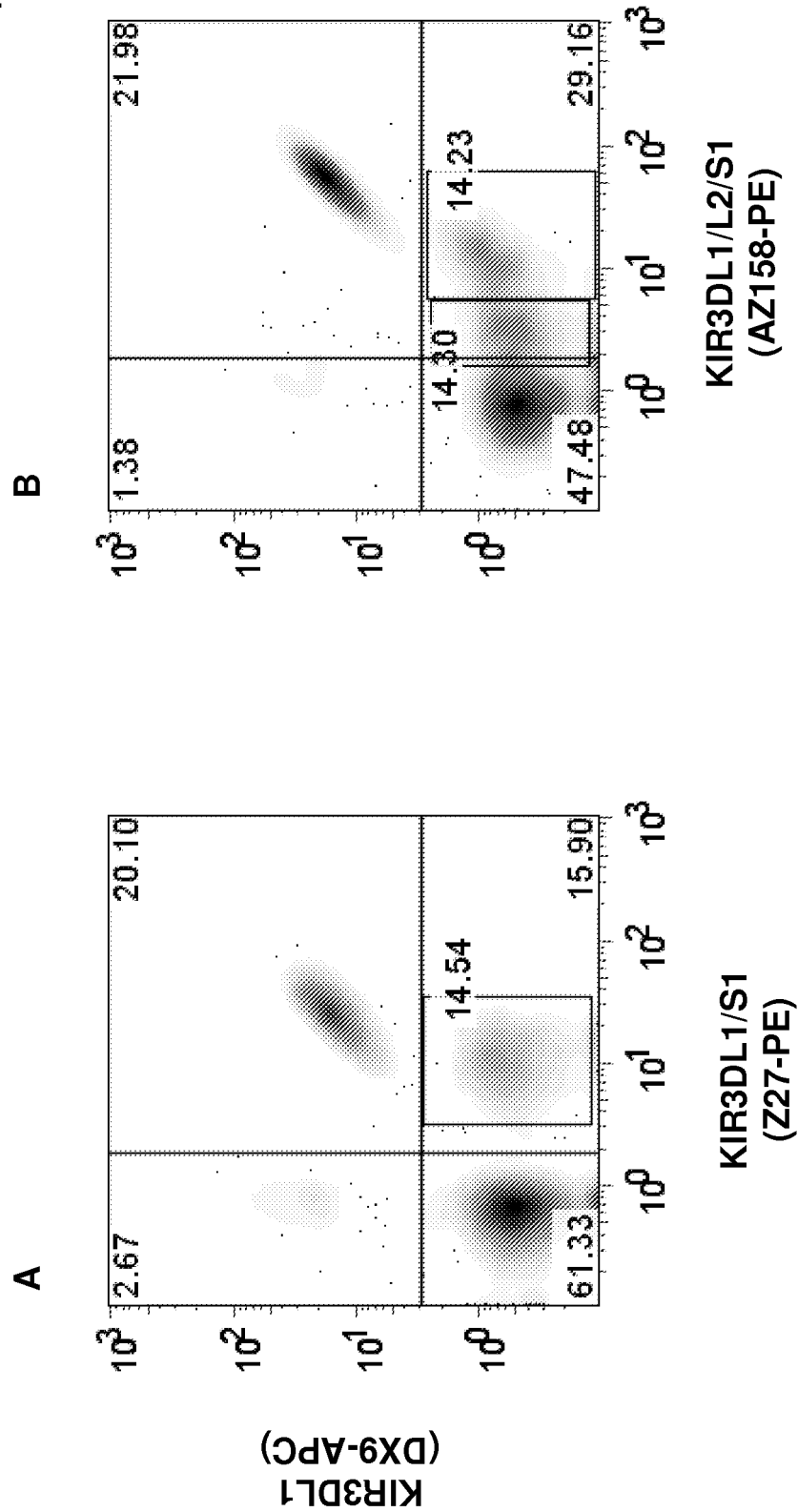
FIG. 4 shows the staining patterns for PBMC from a healthy donor gated on $CD3^-CD56^+$ (NK lymphocytes), incubated with mAbs PE-DX9, PE-Z27 and PE-AZ158, washed and labeled.
Figure 5:
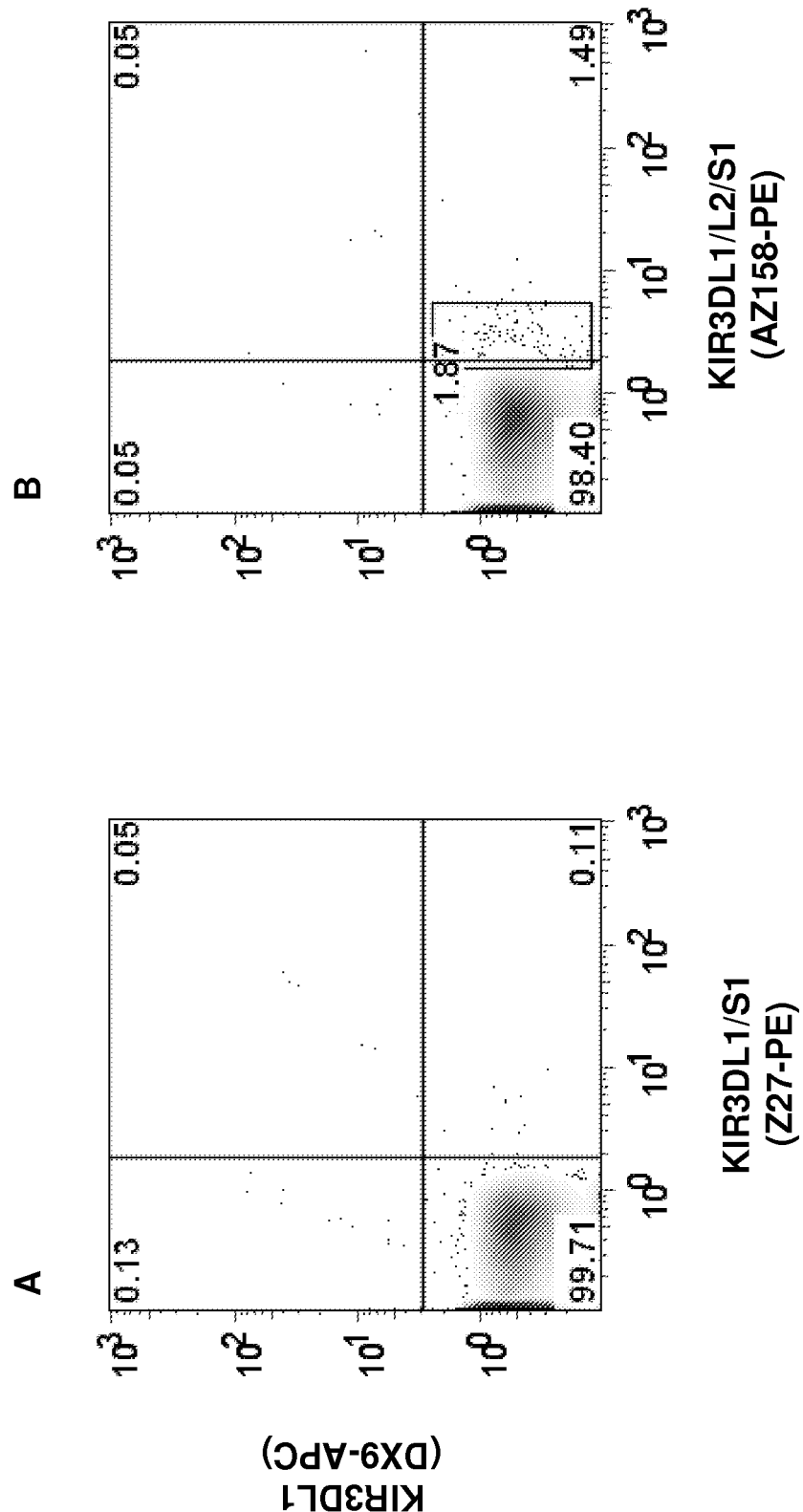
FIG. 5 shows the staining patterns for PBMC from a healthy donor gated on $CD3^+$ (T lymphocytes), incubated with mAbs PE-DX9, PE-Z27 and PE-AZ158, washed and labeled.

Flow cytometry experiments were repeated for a number of individual healthy donors, using different antibodies to discriminate between the different KIR3D populations within T and NK cells. Antibodies Z27-PE (specific for KIR3DL1 and KIR3DS1; Beckman Coulter Corp., CA, product ref. IM3292) and DX9-PE (specific for KIR3DL1 only; Miltenyi Biotec, Germany product ref. 130-092-473), together with AZ158-PE. Results for a representative individual having a genotype that expressed each of the three KIR3D receptors are shown in FIGS. 4 and 5. FIGS. 4A and 4B show the staining patterns for PBMC gated on CD3$^-$CD56$^+$ (NK lymphocytes), incubated with mAbs PE-DX9, PE-Z27 and PE-AZ158, washed and labeled. FIG. 4A shows Z27 staining on the x-axis indicating cells that are KIR3DL1/DS1+ and DX9 staining on the y-axis indicating the KIR3DL1+ cell population. FIG. 4B shows AZ158 staining on the x-axis indicating cells that are KIR3DL1/DL2/DS1+ and DX9 staining on the y-axis indicating the KIR3DL1+ cell population. Comparing FIGS. 4A and 4B one can see an additional population in the lower right quadrant of Figure B that corresponds to the additional KIR3DL2 specificity of AZ158 compared to Z27. On NK cells in this individual, about 14% of NK cells were positive for each of KIR3DL2 and KIR3DS1 while 20-22% of NK cells expressed KIR3DL1.

FIGS. 5A and 5B show the staining patterns for PBMC gated on CD3$^+$ (T lymphocytes), incubated with mAbs PE-DX9, PE-Z27 and PE-AZ158, washed and labeled. FIG. 5A shows Z27 staining on the x-axis indicating cells that are KIR3DL1/DS1+ and DX9 staining on the y-axis indicating the KIR3DL1+ cell population. FIG. 5B shows AZ158 staining on the x-axis indicating cells that are KIR3DL1/DL2/DS1+ and DX9 staining on the y-axis indicating the KIR3DL1+ cell population. Comparing FIGS. 5A and 5B one can see a minor additional population in the lower right quadrant of FIG. 5B that corresponds to the additional KIR3DL2 specificity of AZ158 compared to Z27. On NK cells in this individual, about 2% of NK cells were positive for any of KIR3DS1, KIR3DL2 and KIR3DS1.

B. Binding to Immobilized KIR3DL1 and KIR3DL2 Proteins

Figure 6:
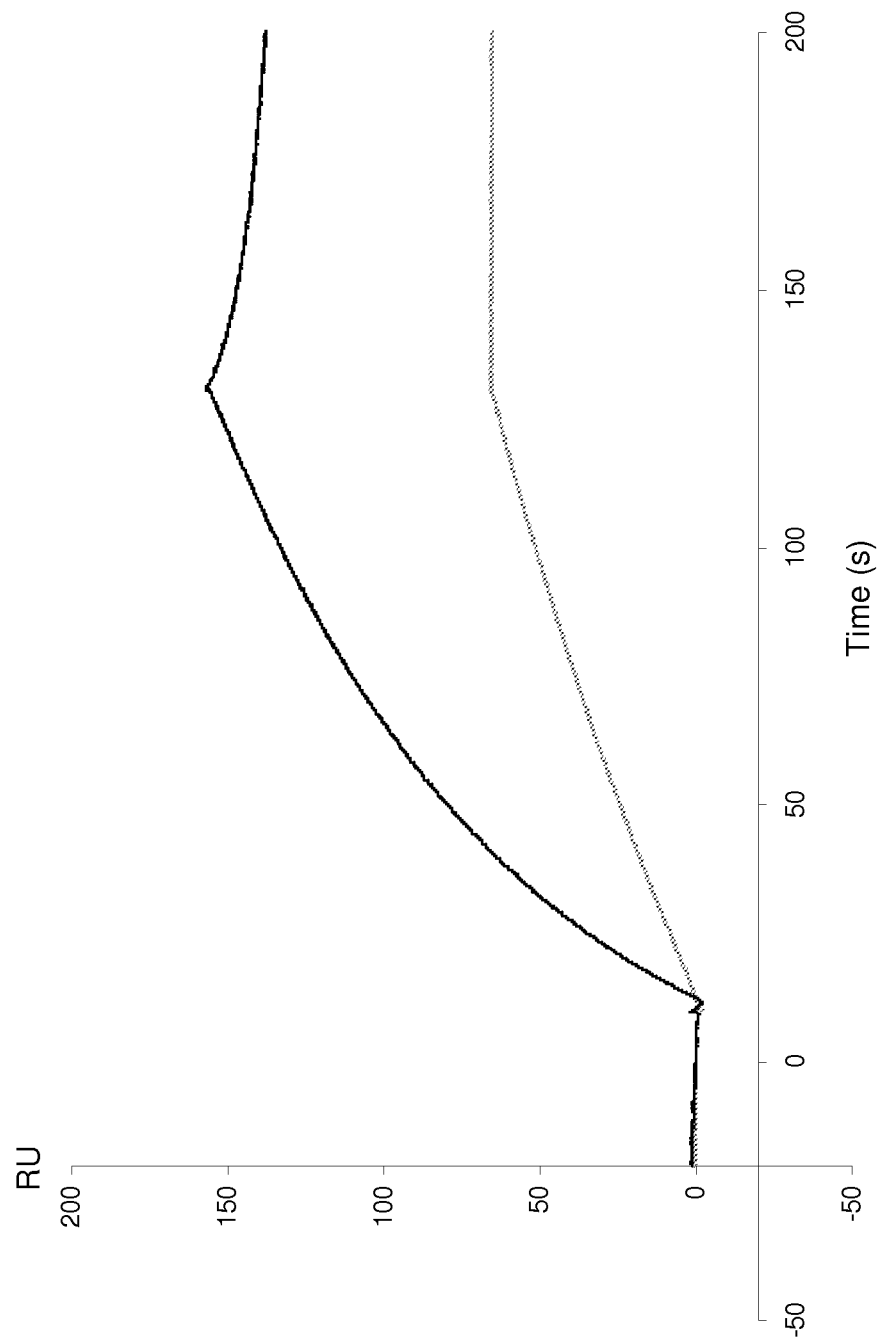
FIG. 6 shows the sensorgrams for the binding of chAZ158 to KIR3DL2 (black; upper line) and KIR3DL1 (grey; lower line) chips, superimposed, with resonance units (RU) on the y-axis and time (seconds) on the x-axis.

The binding of chimeric AZ158 ("chAZ158", see Example 3) to KIR3DL2 and KIR3DL1 recombinant proteins (R&D systems) was analyzed by Surface Plasmon Resonance (SPR) using a Biacore T100 apparatus. FIG. 6 shows the sensorgrams for the binding of chAZ158 to KIR3DL2 (black; upper line) and KIR3DL1 (grey; lower line) chips, superimposed, with resonance units (RU) on the y-axis and time (seconds) on the x-axis. Antibody was injected at a constant concentration of 12 μg/ml over the KIR3DL2 and KIR3DL1 flow-cells. Background signals were subtracted online by co-injecting onto the reference flow cell (dextran alone). Sensorgrams are representative of three independent experiments. The results show that the chAZ158 binds to both KIR3DL1 and KIR3DL2. Additionally, the dissociation phase on the sensorgram indicates that chAZ158 may bind to KIR3DL1 with greater stability to KIR3DL1 and KIR3DL2.

C. chAZ158 Binding Domain on KIR3DL2

Cells and Reagents.

HEK293T/17 cells were cultured in DMEM (Gibco) supplemented with sodium pyruvate (1 mM), penicillin (100 U/ml), streptomycin (100 μg/ml) and 10% heat inactivated FCS (PAN biotech). Lipofectamine 2000 reagent, Trizol, SuperScript II reverse Transcriptase, pcDNA3.1 vector and anti-V5-FITC antibodies were purchased from Invitrogen. Goat anti-Human (H+L)-PE was purchased from Beckman Coulter (PNIM1626).

RNA Extraction and cDNA Preparation.

PBMC ($5 \cdot 10^6$ cells) from *Homo Sapiens* were re-suspended into 1 ml of Trizol reagent. RNA extraction was performed by adding 200 μl chloroform. After centrifugation (15 min, 13.000 rpm), RNA was precipitated from aqueous phase with 500 μl isopropanol. After incubation (10 min, RT) and centrifugation (10 min, 13.000), RNA was washed with 70% ethanol and re-centrifugated (5 min, 13.000 rpm).

RNA was re-suspended in H₂O Rnase free water. cDNA was obtained using SuperScript II reverse Transcriptase using 2 μg of specific RNA and following manufacturer instructions.

Cloning of KIR3DL2 Domain 0, Domain 1 and Domain 2

Human KIR3DL2 (accession number U30272) domain 0, domain 1 and domain 2 sequences are shown in Table 2.

TABLE 2

| Ig-like domain of KIR3DL2 | SEQ ID NO: | Amino acid sequence |
|---|---|---|
| Domain 0 | 21 | PLMGGQDKPF LSARPSTVVP RGGHVALQCH YRRGFNNFML YKEDRSHVPI FHGRIFQESF IMGPVTPAHA GTYRCRGSRP HSLTGWSAPS NPLVIMVTGN HRKPSLLAHP GPLLKSG |
| Domain 1 | 22 | TVILQCWSDV MFEHFFLHRE GISEDPSRLV GQIHDGVSKA NFSIGPLMPV LAGTYRCYGS VPHSPYQLSA PSDPLDIVIT GLYEKPSLSA QPGPTVQAGE |

TABLE 2 -continued

| Ig-like domain of KIR3DL2 | SEQ ID NO: | Amino acid sequence |
|---|---|---|
| Domain 2 | 23 | NVTLSCSSWS SYDIYHLSRE GEAHERRLRA VPKVNRTFQA DFPLGPATHG GTYRCFGSFR ALPCVWSNSS DPLLVSVTGN PSSSWPSPTE PSSKSGICRH LH |

*Homo Sapiens* KIR3DL2 (accession number U30272) domain 0, domain 1 and domain 2 sequences were amplified by PCR reaction from cDNA using 5' AA GCT AGC GGT AAG CCT ATC CCT AAC CCT CTC CTC GGT CTC GAT TCT ACG CTC ATG GGT GGT CAG GAC AAA C (SEQ ID NO 24) (forward) and 3' AA GGA TCC CTC TCC TGA TTT CAG CAG GGT (SEQ ID NO 25) (reverse); 5' AA GCT AGC GGT AAG CCT ATC CCT AAC CCT CTC CTC GGT CTC GAT TCT ACG ACA GTC ATC CTG CAA TGT TGG (SEQ ID NO 26) (forward) and 3' AA GGA TCC CTC TCC TGC CTG AAC CGT GGG (SEQ ID NO 27) (reverse); 5' AA GCT AGC GGT AAG CCT ATC CCT AAC CCT CTC CTC GGT CTC GAT TCT ACG AAC GTG ACC TTG TCC TGT AGC (SEQ ID NO 28) (forward) and 3' AA GGA TCC ATG CAG GTG TCT GCA GAT ACC (SEQ ID NO 29) (reverse) oligonucleotides respectively. After TA-cloning and sequencing, sequences were cloned into pcDNA3.1 vector between NheI and BamHI restriction sites. These constructs were inserted between the CD33 peptide leader and the CD24 GPI anchor (CD24 GPI anchor DNA and amino acid sequences are shown in SEQ ID NOS 30 and 31, respectively) synthesized by MWG Biotech (inserted between BamHI and HindIII restriction sites).

Transfection.

HEK-293T/17 cells were seeded 24 hours prior to transfection into 6 wells plates ($5 \cdot 10^5$ cells/well) in DMEM without antibiotics. Transfections were performed using 5 μg of the different pcDNA3.1/KIR3DL2 domain 0, pcDNA3.1/KIR3DL2 domain 1 or pcDNA3.1/KIR3DL2 domain 2 constructs using Lipofectamine 2000 according to manufacturer instructions. To ensure DNA purity for transfection, Maxiprep endotoxin free kit from Qiagen was used. The Lipofectamine/DNA ratio used was fixed at 2/1. Cells were harvested 48 hours after transfection for flow cytometry experiments.

Flow Cytometry.

Cells were harvested and stained in PBS1×/BSA 0.2%/EDTA 2 mM buffer during 1 H at 4° C. using 5 μg/ml of chiAZ158 antibody. After two washes in staining buffer, cells were stained for 30 min at 4° C. with anti-V5 antibody FITC (0.1 μl per well) and goat anti-human (H+L)-PE antibodies (1/200). After two washes, stainings were acquired on a BD FACS Canto II and analyzed using the FlowJo software.

Results.

In order to determine where the chAZ158 antibody binds on the KIR3DL2 molecule, three constructs were created. They consist of the DNA encoding the extracellular domain 0, 1 or 2 of the KIR3DL2 molecule (SEQ ID NOS 21, 22 and 23, respectively) linked to DNA encoding the CD24-GPI anchor (SEQ ID NO 30) to allow cell surface expression. These constructs are all tagged with the V5 epitope for cell surface detection by flow cytometry.

Figure 7:
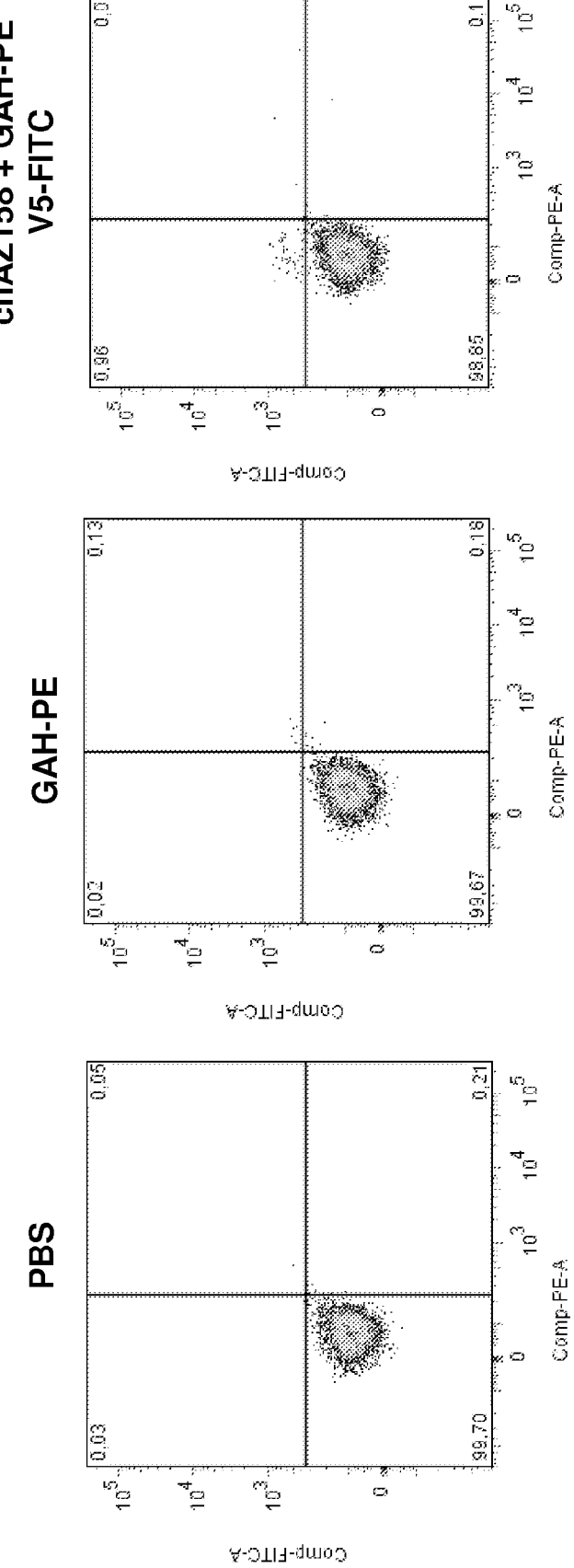
FIGS. 7-10 show staining to untransfected cells (FIG. 7) or cells transfected with DNA encoding the extracellular domain 0 (FIG. 8), domain 1 (FIG. 9) or domain 2 (FIG. 10) of the KIR3DL2 molecule, in each case linked to DNA encoding the CD24-GPI anchor. V5-FITC staining is indicated on the y-axis and chAZ158-GAH-PE on the x-axis. The figures show that chAZ158 binds to cells expressing domain 0 but not to cells expressing domains 1 or 2.
Figure 8:
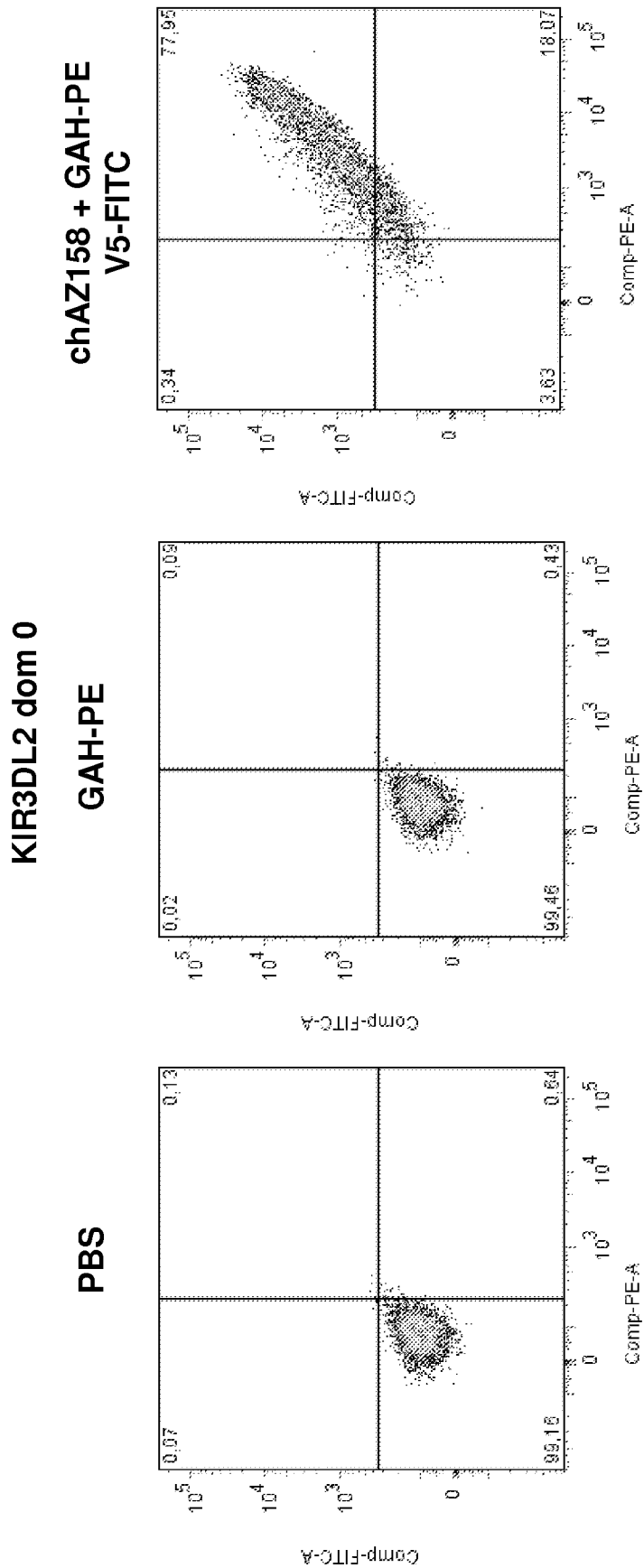
Figure 9:
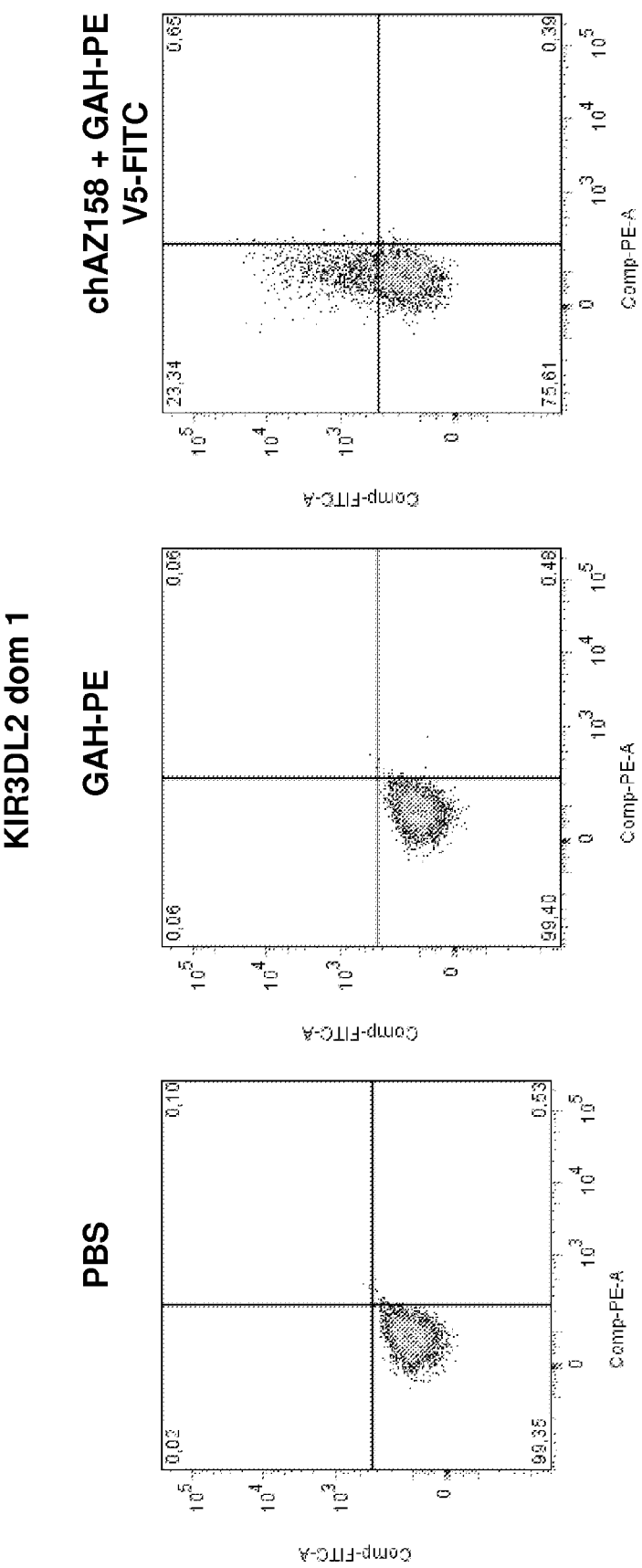
Figure 10:
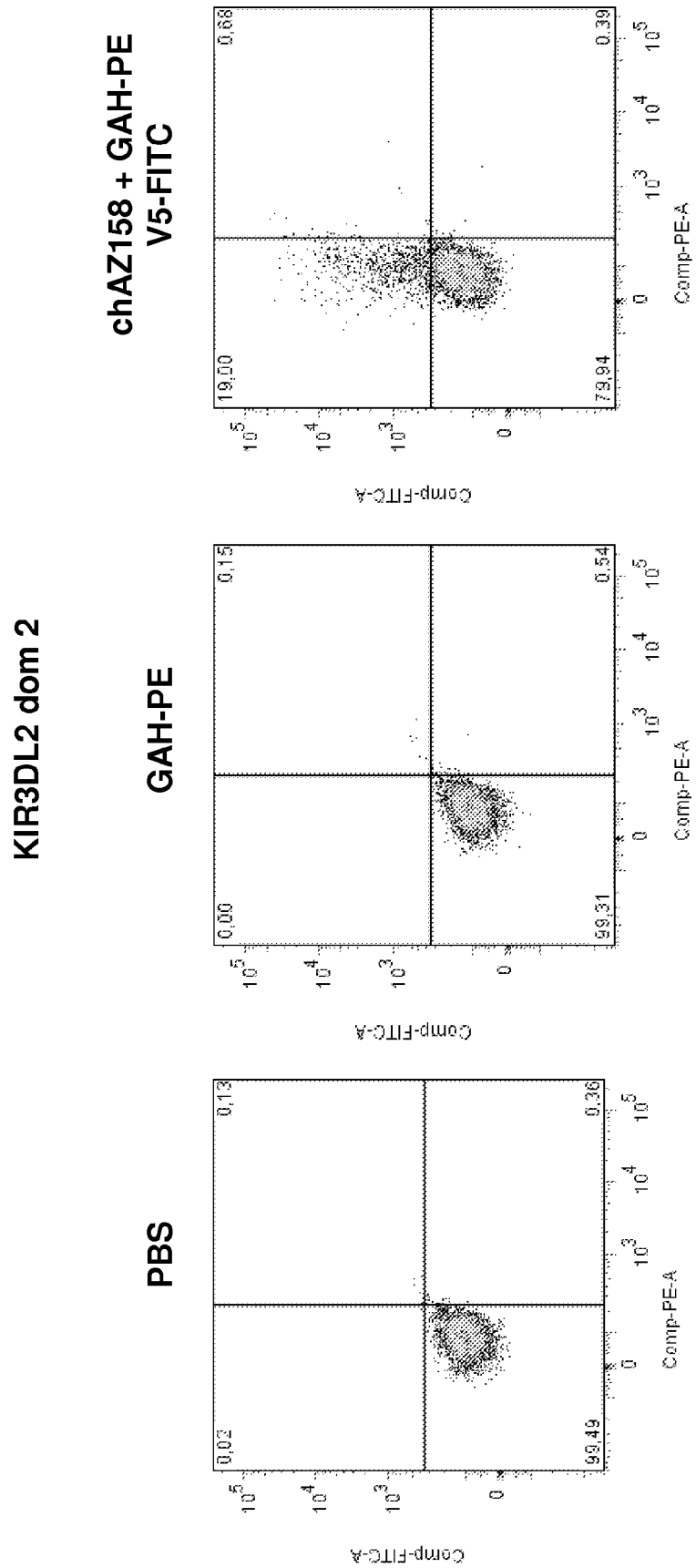

All the three constructs were expressed at the HEK-293T/17 cell surface; V5 positive cells could be detected in all conditions, although more expression of KIR3DL2 domain 0 construct at the cell surface was observed compared with KIR3DL2 domain 1 and domain 2 constructs. Results are shown in FIGS. 7-10, with V5-FITC indicated on the y-axis and chAZ158-GAH-PE on the x-axis. Staining on untransfected cells are shown in FIG. 7. A strong positive signal is observed with the chAZ158 antibody on HEK-293/17 cells transfected with the KIR3DL2 domain 0 construct (FIG. 8). No binding of the chiAZ158 antibody could be detected on KIR3DL2 domain 1 (FIG. 9) or domain 2 (FIG. 10). Therefore, it can be concluded from this flow cytometry experiment that the chAZ158 antibody binds to the KIR3DL2 extracellular domain 0 but not to domains 1 and 2.

Example 3

Chimerization of AZ158 Heavy and Light Chain Variable Regions

Frozen cell pellets of mouse hybridoma line, AZ158, were thawed and processed using the RNeasy Midi Kit (Qiagen cat. No. 75142) to isolate total RNA. About 5 micrograms of AZ158 RNA was subjected to reverse transcription to produce AZ158 cDNA using the Amersham Biosciences 1st strand synthesis kit (Amersham Biosciences, Cat. No. 27-9261-01). Immunoglobulin heavy chain variable region (VH) cDNA was amplified by PCR using 12 different IgH primers in combination with a constant region primer in order to determine which primer pair was the most suitable for PCR. Similarly, immunoglobulin kappa chain variable region (VK) was amplified using multiple IgK primers in combination with a kappa constant region primer.

Only a single set of primers gave an amplification product for the heavy chain variable regions. The amplification products were ligated separately into pCR2.1®-TOPO Vectors® for transformation into *E. coli* TOP10 bacteria, amplification and sequencing (using the BigDye® Terminator v3.0 Cycle Sequencing Ready Reaction Kit (ABI). The amino acid sequence of the heavy chain variable region (AZ158 VH) is set forth in SEQ ID NO: 8.

For the light chain, three single amplification products were obtained, designated MKV2, MKV6 and MKV7, with the remaining primers yielding no products. The amino acid sequence of the light chain variable region (AZ158 VK) arising from MKV6 is set forth in SEQ ID NO: 10. MKV2 light chain corresponded to a sterile kappa transcript originating from a myeloma cell fusion partner. As described further below, MKV7 light chain was non-functional in antigen binding assays. The MKV2 product was a sterile transcript common to most hybridomas.

Chimerization of the AZ158 VK products derived using MKV6 and MKV7 involved introducing via the appropriate primers and PCR, a Hind III restriction site, a Kozak translation initiation site and the PC613 (for MKV6) kappa leader sequence selected for similarity from the Kabat database at the 5' end and a splice donor site and Bam HI restriction site at the 3' end of the AZ158 VK DNA sequence. The resulting PCR product was cloned into a vector encoding the constant region of the human kappa light chain so as to encode a full-length chimeric light chain containing the variable region of the AZ158 light chain.

Chimerization of AZ158 VH involved introducing, by PCR and the appropriate primers, a Hind III restriction site, a Kozak translation initiation site and the H26 leader sequence at the 5' end, and, at the 3' end, the human gamma1 C region 5' fragment up to a natural Apa I restriction site. The resulting PCR product was cloned into a vector encoding the constant region of the human IgG1 heavy chain so as to encode a full-length chimeric IgG1 heavy chain containing the variable region of the AZ158 heavy chain.

The resulting plasmids encoding: a/ the chimeric heavy and b/ one of the two kappa chains; were electroporated together into COS 7 cells. Conditioned media from these cells contained the resulting chimerized IgG1-kappa antibody, chAZ158, which was then protein A purified. The purified antibodies were tested for binding to KIR3DL2-expressing Cou-L cells. The chAZ158 antibody including the MKV6-derived kappa chain, bound Cou-L cells. However the antibody including the MKV7-derived kappa chain did not bind these cells and therefore this kappa chain was not derived from the mouse anti-KIR3DL2 antibody.

AZ158 is unusual in that it produces multiple kappa transcripts, with apparently functional coding sequences. We therefore expressed two chimeric antibodies with the two different kappa leader and variable region sequences. The good expression of the chimeric version of these two kappa chains in association with the single chimeric heavy chain in COS cells after three days of culture indicated that these kappa coding sequences are functional. However, only chAZ158 antibody including the MKV6 light chain bound KIR3DL2-expressing cells. The reason for this complex situation may be due to expression failure due to the non-coding region of the MKV7 transcript such that the $2^{nd}$ allele producing the MKV6 transcript was rearranged in the parental B cell line. Alternatively, the hybridoma may be a product of a 3-cell fusion, from which the chromosomes bearing both the functionally rearranged light chains were retained, but from which, one of the rearranged heavy chain chromosomes was expelled.

Example 4

AZ158 Inhibits Tumor Growth In Vivo

AZ158 (murine IgG2b) was tested for inhibition of tumor growth in a syngeneic mouse model. Briefly, different B16 murine melanoma cell lines were transfected with KIR3DL2, yielding clone A1+ having about 90% cells AZ158+, clone A1− having about 20% cells AZ158+ and clone A3 having about 3% cells AZ158, as well as a mock transfected control.

Figure 2:
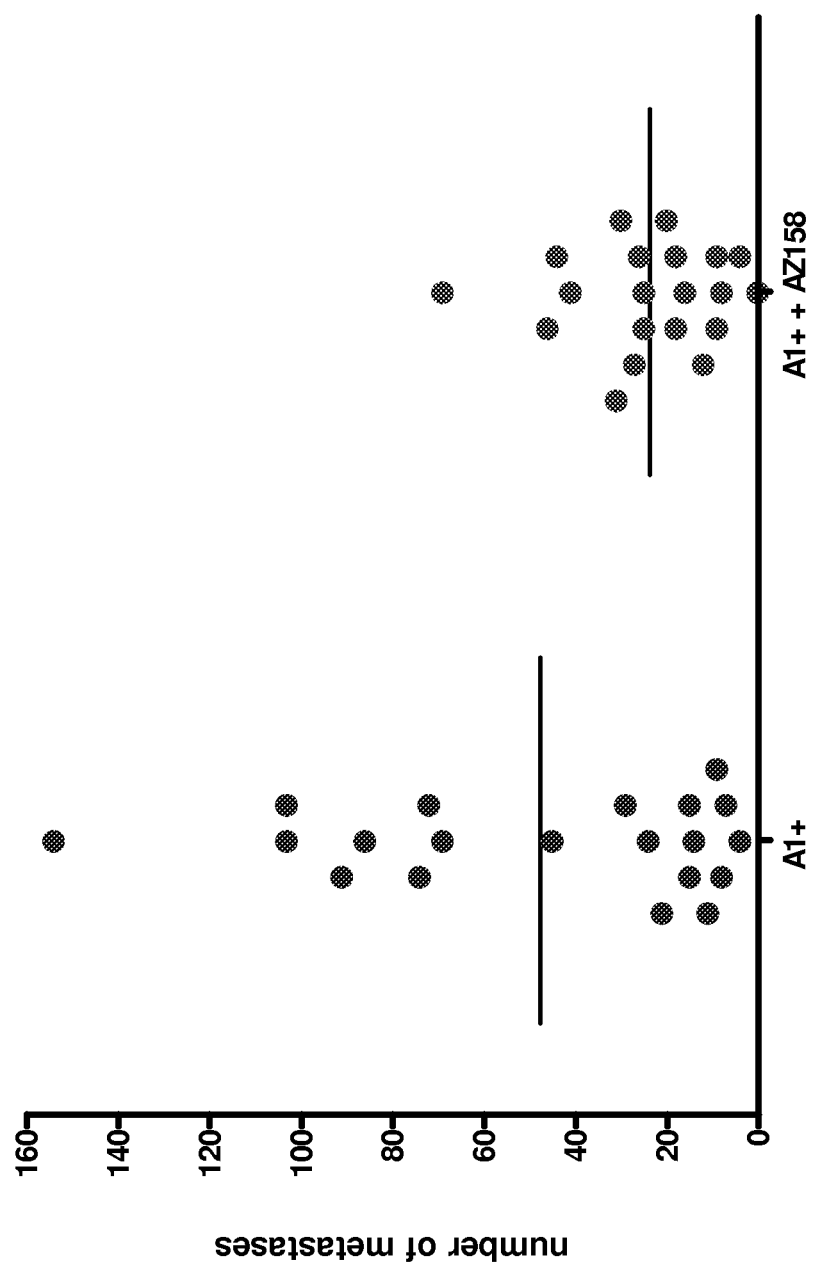
Figure 3:
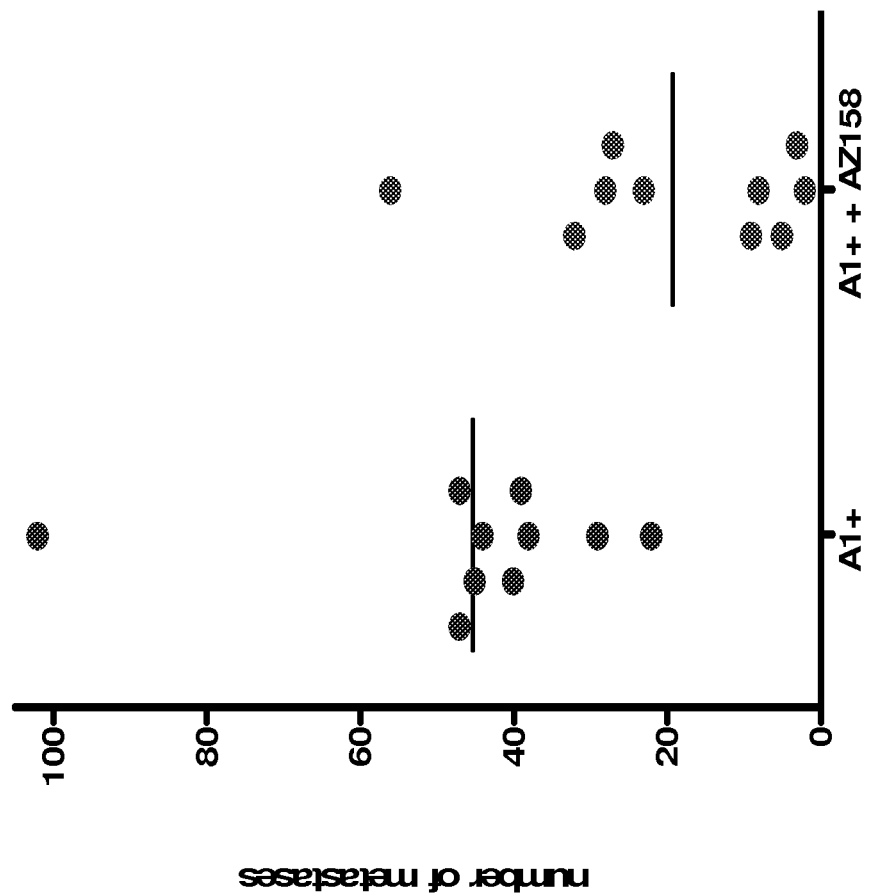

C57B16 mice were then treated with A1+ cells and AZ158 in three series of experiments and the number of lung metastases was assessed at day 20 as a measure of tumor progression. In a first experiment (FIG. 1), A1+ cells were injected at 0.3 $10^6$ cells/mouse IV "tail" 100 μl, to 12 week old female mice, followed by AZ158 via intraocular injection. Mice received either A1+ cells only on day 0 (6 mice) or A1+ on day 0, 250 μg/mouse AZ158 on day −1, and 100 μg/mouse on days 1, 5 and 7) (8 mice). Results in FIG. 1 demonstrate that AZ158 decreased the number of metastases significantly. In a second experiment (FIG. 2), A1+ cells were injected at 0.3 $10^6$ cells/mouse IV "tail" 200 μl, to 12 week old female mice, followed by AZ158 via intraocular injection. Mice received either A1+ cells only on day 0 (20 mice) or A1+ on day 0, 250 μg/mouse AZ158 on day −1, and 100 μg/mouse on days 1, 5 and 7) (20 mice). Results in FIG. 2 again demonstrate that AZ158 decreased the number of metastases significantly. In a third experiment (FIG. 3), A1+ cells were injected at 0.3 $10^6$ cells/mouse IV "tail" 200 μl, to 13 week old female mice, followed by AZ158 via intraocular injection. Mice received either A1+ cells only on day 0 (10 mice) or A1+ on day 0, 250 μg/mouse AZ158 on day −1, and 100 μg/mouse on days 1, 5 and 7) (10 mice). Results in FIG. 3 again demonstrate that AZ158 decreased the number of metastases significantly.

Example 5 chAZ158 Directly Inhibits Cell Proliferation in CD4+ Cou-L Cells

To investigate the mode of action of antibody AZ158, the antibody was assessed for its direct effect on Cou-L cells (Sezary Syndrome cells; KIR3DL2 positive) in a cell proliferation assay. Cou-L cells were cultured in RPMI (Gibco) supplemented with sodium pyruvate (1 mM), 100 IU/ml Pen/Strep), 2 mM L-glutamine, IL-2 (200 U/ml) and 10% heat inactivated AB serum into 24 well plates (Falcon, reference 353047). Antibodies were incubated overnight in 1×PBS at 4° C. into white opaque 96 well plates (Falcon, reference 353296). The chAZ158 antibody (human IgG1 produced in EB66 cells) was used at 20 or 100 µg/ml. A chimeric isotypic control produced in the same condition was used at the same concentrations. Finally, anti-Class I antibody (W6.32 clone, 100 µg/ml) was also used as another control. Cou-L cells (1.000/well) were seeded into the wells previously washed once with 1×PBS. Proliferation was assessed after two, five and eight days using the CellTiter-Glo Luminescent Cell Viability Assay (Promega) according to the manufacturer's instruction. Luminescence was measured using a Mithras LB940 (Berthold Technologies).

Figure 11:
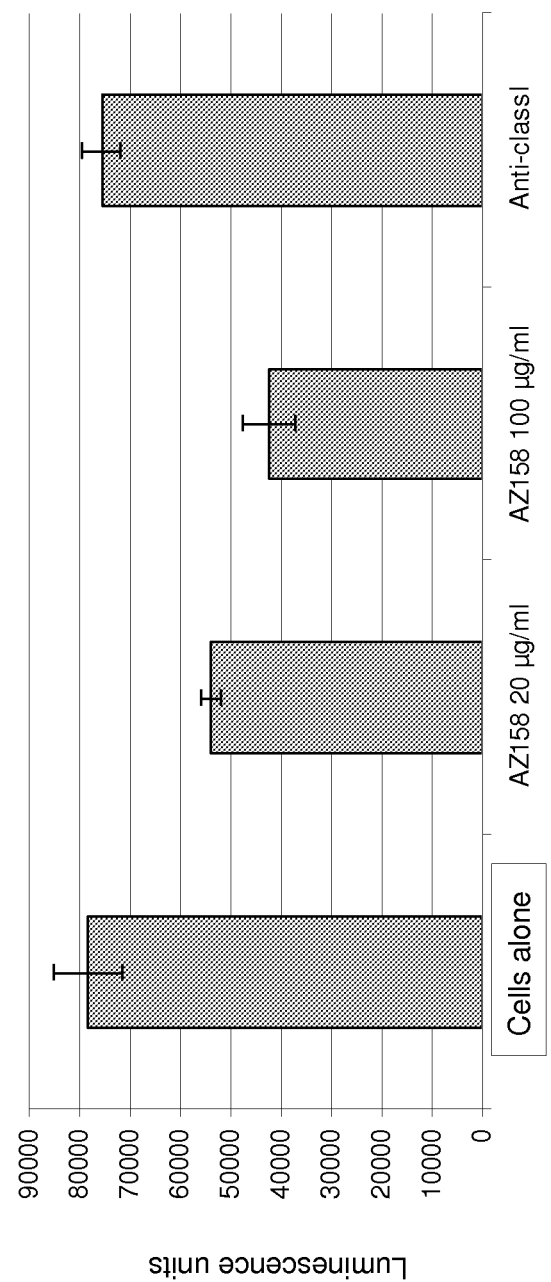
FIG. 11 shows a direct effect on Cou-L cells (Sezary Syndrome cells; KIR3DL2 positive) in a cell proliferation assay where Cou-L cells were cultured with chAZ158 antibody, a chimeric isotypic control produced in the same conditions or anti-Class I antibody. Results show that chAZ158 has a strong direct inhibitory effect on Cou-L cell proliferation.

The results are shown in FIG. 11. Luminescence units are shown on the y-axis; luminescence depends on the quantity of ATP present, which in turn is proportional to the number of metabolically active cells at the time proliferation is assessed. ChAZ158 but not control antibody significantly inhibited Cou-L cell proliferation in vitro.

Example 6

Expression of chAZ158 in CHO and EB66 Cells

ChAZ158 was expressed in both CHO and EB66 cells. Chicken EB14 and duck EB66 cells were grown in serum free medium (Excell—from SAFC Biosciences) supplemented with 2.5 mM glutamine. CHO-K1 cells were transfected in suspension using CHO PFM serum free medium (Gibco, BRL, Gaithersburg) supplemented with 8 mM glutamine. During the selection phase, the CHO-K1 cells were cultured in DMEM DF12 (Gibco, BRL, Gaithersburg), supplemented with 5% FBS and Geneticin.

Immunoglobulin heavy chain variable region (VH) cDNA and immunoglobulin kappa chain variable region (VK) cDNA encoding the VH and VK amino acid sequence set forth in SEQ ID NO: 8 and SEQ ID NO: 10 were cloned into expression vectors pVVS620 (pEF1/HTLV) and pVVS623 (pRSV). The cDNA sequences encoding the full chimeric AZ158 heavy and light chains are shown in SEQ ID NOS 17 and 19, respectively, and corresponding amino acid sequences in SEQ ID NOS 18 and 20. Expression vectors pVVS620 (pEF1/HTLV) and pVVS623 (pRSV) were transfected in serum-free medium into EB14, EB66 and CHO-K1 cells by electroporation (Amaxa). Three days post-transfection, the selection agent (0.25 mg/ml of geneticin for EB14 cells, 0.15 mg/mL for EB66 cells and 0.5 mg/mL for CHO-K1) is added to the cell culture medium. The geneticin resistant clones were isolated, picked up and cultured in larger vessels (microplates, flasks, then bioreactors).

An ELISA screening assay was performed on stably transfected clones to detect antibody expression level in supernatant. This assay employs the quantitative sandwich enzyme immuno assay technique. An anti IgG-Fc specific antibody is pre-coated onto a 96 well-plate. Standards, samples and conjugates are added to the wells and any IgG present is sandwiched by the immobilized antibody and a second enzyme-linked monoclonal antibody specific for IgG-kappa. Following a wash to remove any unbound substances and/or antibody-enzyme reagent, a substrate solution is added to the wells and coloration develops in proportion to the amount of IgG bound. Reaction is stopped and coloration intensity is measured (O.D. 490 nm). A standard curve is constructed by plotting the mean absorbance for each standard on the y-axis against the concentration on the x-axis and draw a best fit curve through the points of the graph. The concentration of each unknown sample is determined by calculating the concentration of the IgG corresponding to the mean absorbance from the standard curve. For samples, the concentration determined from the standard curve must be multiplied by the dilution factor.

Example 7 chAZ158 Produced in EB66 Cells Induces ADCC of Target Cells

Materials and Methods

Cells and reagents. Cou-L cells were cultured in RPMI (Gibco) supplemented with sodium pyruvate (1 mM), 100 IU/ml Pen/Strep), 2 mM L-glutamine, IL-2 (200 U/ml) and 10% heat inactivated AB serum into 24 well plates (Falcon, reference 353047). B221 cells were cultured in RPMI-1640 media supplemented with 10% heat inactivated FBS, 2 mM L-glutamine, 100 IU/ml Pen/Strep, and 1 mM Sodium Pyruvate into T75 flak.

Flow cytometric assay for CD107 mobilization and IFN-γ production. Thawed human PBMC stimulated or not overnight with 100 UI/mL of IL-2 were mixed with Cou-L cells (Sezary Syndrome patient PBMC kindly provided by A. Bensussan) or B221 cell lines at an effector/target ratio equal to 10, alone or in the presence of mouse AZ158, chAZ158 produced in CHO, chiAZ158 produced in EB14 or chiAZ158 produced in EBX (EB66) (used at 25 µg/mL) or rituxan (25 µg/mL). Cells were then incubated for 4 hours at 37° C. in the presence of FITC conjugated anti-CD107 mAbs (Becton Dickinson) and monensin (sigma). After incubation, cells were washed in PBS containing 2 mM EDTA to disrupt cell conjugates and stained for extracellular markers (PC5 conjugated anti-CD56 and PC7 conjugated anti-CD3 purchased from Beckman coulter). Cells were then fixed and permeabilized using IntraPrep reagent (Beckman Coulter). Intracellular IFN-γ was revealed using PE conjugated anti-IFN-γ purchased from Becton Dickinson. Samples were then analysed on FACScanto (Becton Dickinson).

Chromium release assay. The cytolytic activity of human PBMC was assessed in a classical 4-h $^{51}$Cr-release assay in 96 well plates V from (Greiner). Briefly, Cou-L cells were labeled with $^{51}$Cr (100 µCi (3.7 MBq)/1×10$^6$ cells), then mixed with PBMC stimulated or not overnight with 10 UI/mL of IL-2 at an effector/target ratio equal to 50, in the presence of chiAZ158 produced in CHO, chAZ158 produced in EB14 or chAZ158 produced in EBX (concentration ranging from 0 to 50 µg/mL). After brief centrifugation and 4 hours of incubation at 37° C., 50 µL supernatant were removed, and the $^{51}$Cr release was measured with a TopCount NXT beta detector (PerkinElmer Life Sciences, Boston, Mass.). All experimental groups were analyzed in duplicate or triplicate, and the percentage of specific lysis was determined as follows: 100×(mean cpm experimental release−mean cpm spontaneous release)/(mean cpm total release−mean cpm spontaneous release). Percentage of total release obtained by lysis of target cells with 2% Triton X100 (Sigma).

Results

Results are shown in FIGS. 12 to 16, demonstrating a remarkable increase in ADCC of Sezary Syndrome cells for chAZ158 produced in EB14 or EBX (EB66) cells, compared to the same antibody produced in CHO cells.

Figure 12:
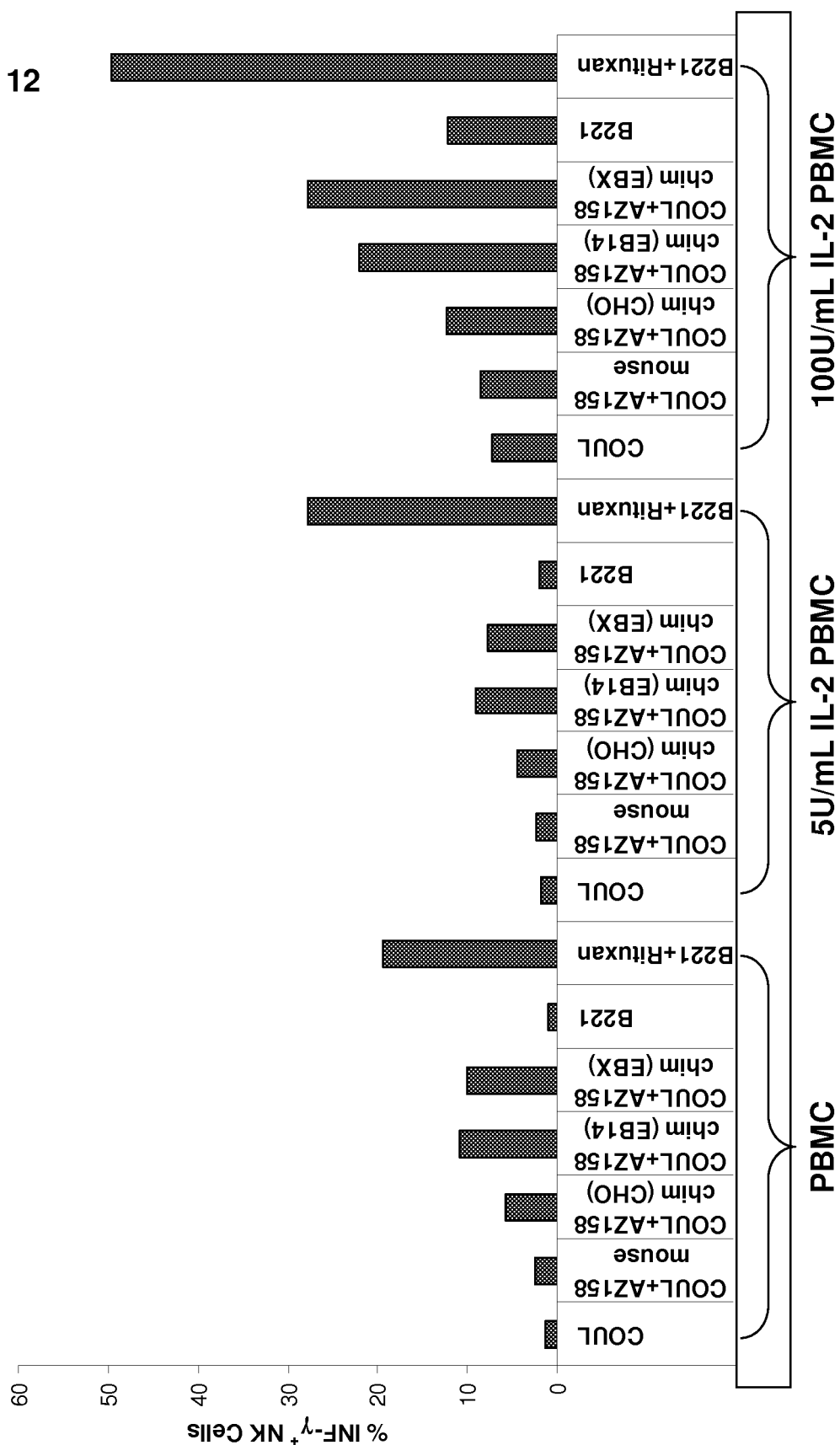
FIG. 12 shows chAZ158-induced IFN-γ production by human NK cells against Cou-L cell targets. ChAZ158 produced by EB14 or EBX cells showed a strong increase of IFN-γ producing NK cells compared to chAZ158 produced by CHO.

FIG. 12 shows chAZ158-induced IFN-γ production by human NK cells against Cou-L cell targets. Thawed PBMC were incubated (overnight) OVN with or without IL-2 (5 or 100 U/mL) then mixed with Cou-L or B221 cells (E/T ratio=10) alone or in the presence of 25 µg/mL of mentioned mAbs (i.e. Mouse or chimeric AZ158 or Rituxan). After 4 h incubation in the presence of anti-CD107, cells were stained with anti-CD3, anti-CD56 and anti-IFN-γ. Percentages of IFN-γ producing NK cells (defined as CD3$^-$CD56$^+$ lymphocytes) are shown. Results are representative of 2 independent experiments, made with 2 different sets of PBMC. In each case, and independent of IL-2 pre-treatment, chAZ158 produced by EB14 or EBX cells showed a strong increase of IFN-γ producing NK cells compared to chAZ158 produced by CHO.

Figure 13:
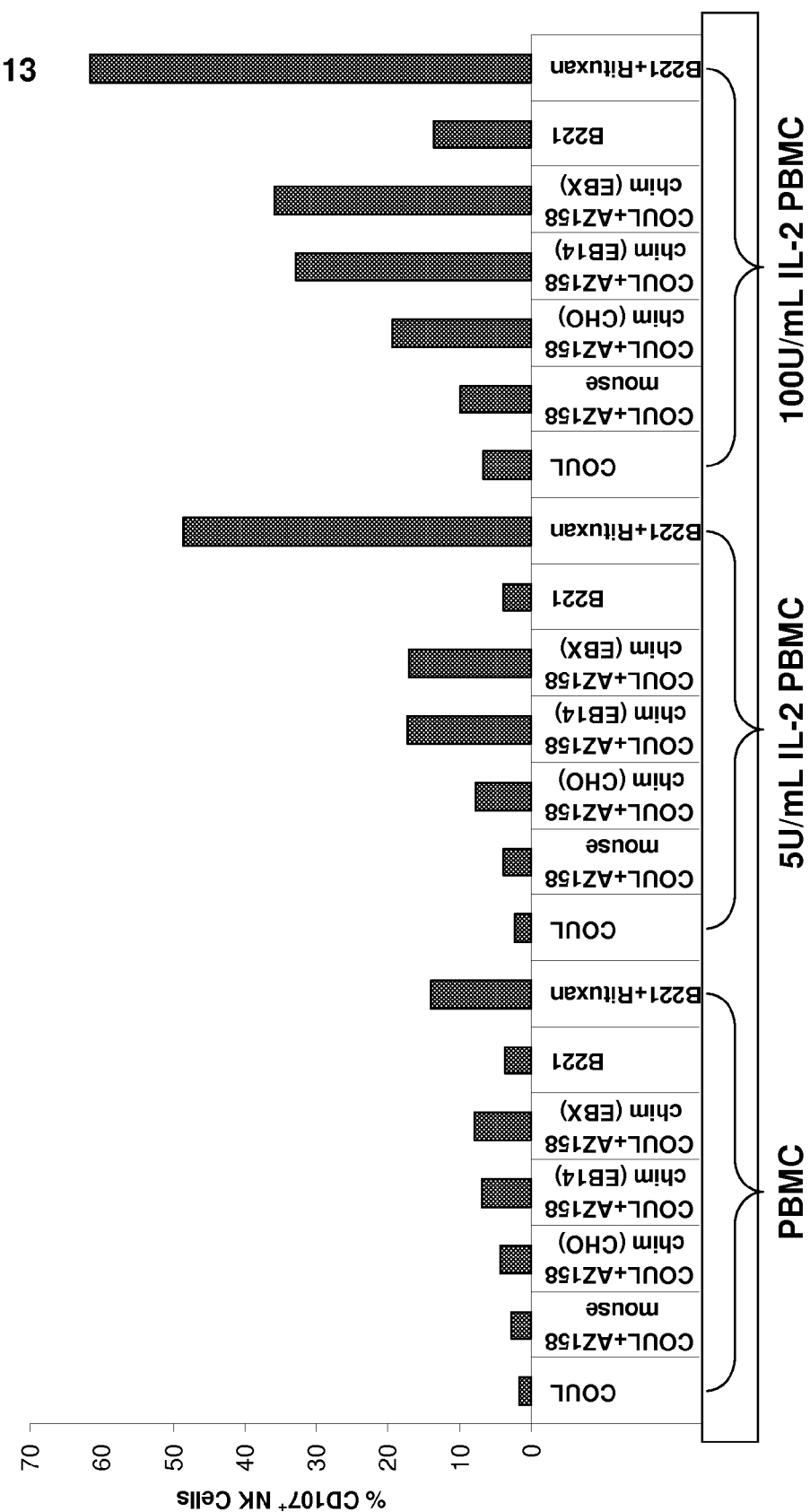
FIG. 13 shows chAZ158-induced CD107 mobilization by human NK cells against Cou-L cells. ChAZ158 produced by EB14 or EBX cells showed a strong increase in percentages of CD107 positive NK cells compared to chAZ158 produced by CHO.

FIG. 13 shows chAZ158-induced CD107 mobilization by human NK cells against Cou-L cells. Thawed PBMC were incubated OVN with or without IL-2 (5 or 100 U/mL) then mixed with Cou-L or B221 cells (E/T ratio=10) alone or in the presence of 25 µg/mL of mentioned mAbs (i.e. Mouse or chimeric AZ158 or Rituxan). After 4 h incubation in the presence of anti-CD107, cells were stained with anti-CD3, anti-CD56 and anti-IFN-γ. Percentages of CD107 positive NK cells (defined as CD3$^-$CD56$^+$ lymphocytes) are shown. Results are representative of 2 independent experiments, made with 2 different sets of PBMC. In each case, and independent of IL-2 pre-treatment, chAZ158 produced by EB14 or EBX cells showed a strong increase in percentages of CD107 positive NK cells compared to chAZ158 produced by CHO.

Figure 14:
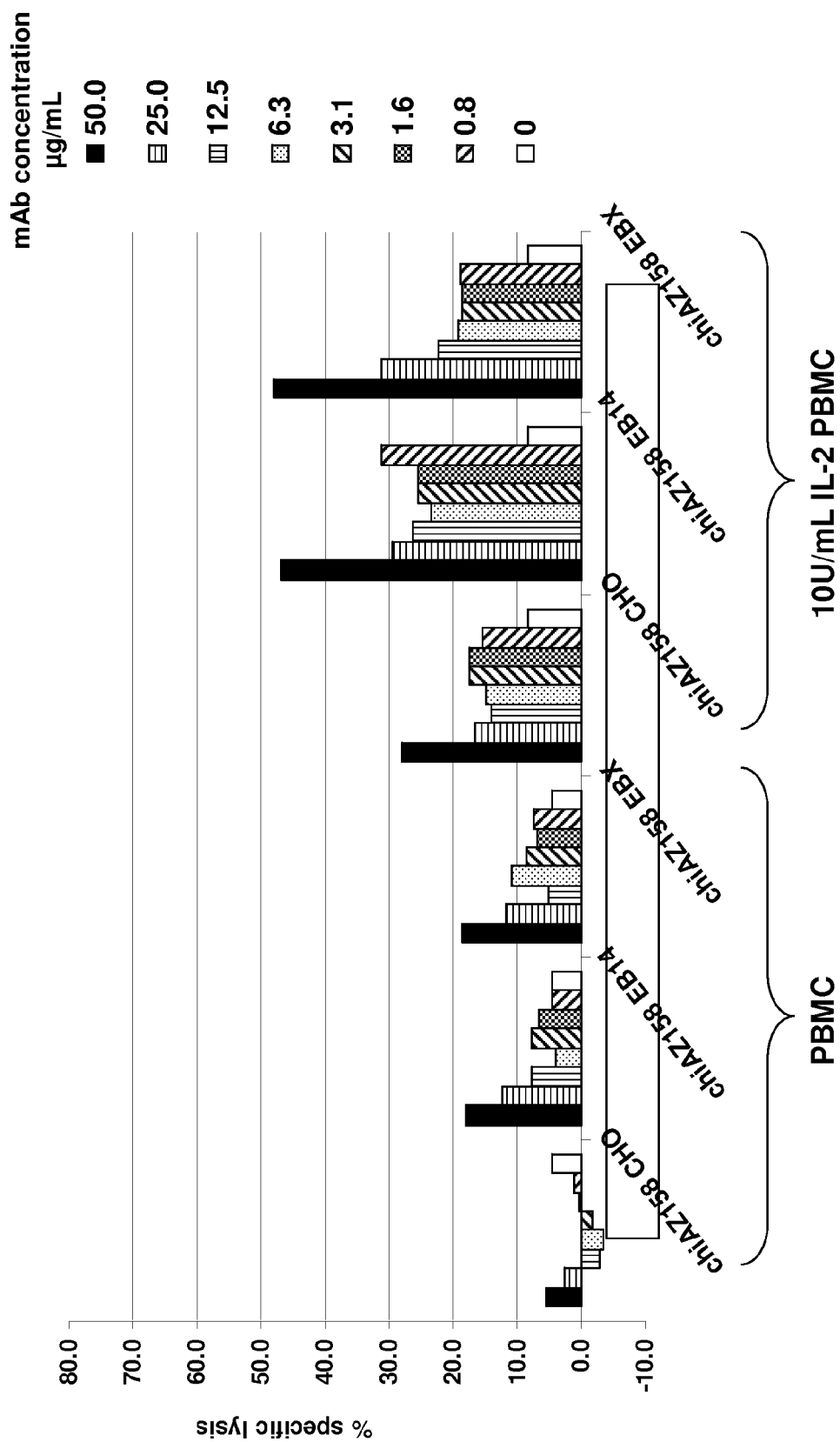
FIG. 14 shows chAZ158-induced induced specific lysis of Cou-L cells by human NK cells. ChAZ158 produced by EB14 or EBX cells showed a strong increase in percentages of specific lysis compared to chAZ158 produced by CHO.

FIG. 14 shows chAZ158-induced specific lysis of Cou-L cells by human NK cells. Thawed PBMC were incubated OVN with or without IL-2 (10 U/mL) then mixed with radio-labeled Cou-L cells (E/T ratio=50) alone or in the presence of increasing concentration (up to 50 µg/mL) of mentioned chimeric AZ158 mAbs. After 4 h incubation, chromium release was measured in culture supernatant. Shown specific lysis percentages were calculated as described in M&M. Results are representative of 2 independent experiments. For each concentration of antibody, and independent of IL-2 pre-treatment, chAZ158 produced by EB14 or EBX cells showed a strong increase in percentages of specific lysis compared to chAZ158 produced by CHO.

Figure 15:
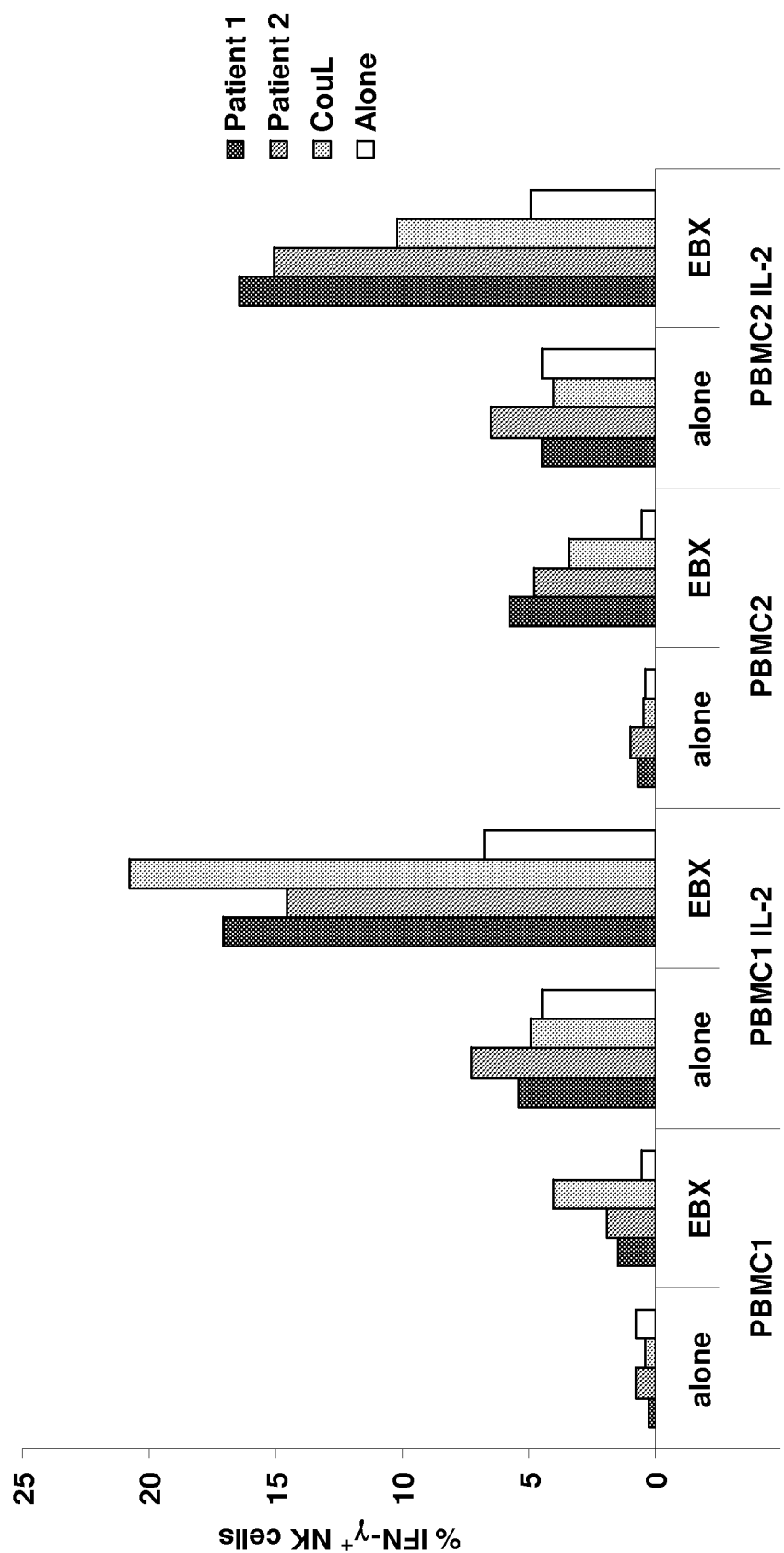
FIG. 15 shows chAZ158-induced IFN-γ production by heterologous NK cells against Sezary syndrome patient PBMC. ChAZ158 produced by EBX cells induced a strong increase in IFN-γ producing NK cells compared to NK cells in the absence of chAZ158.

FIG. 15 shows chAZ158-induced IFN-γ production by heterologous NK cells against Sezary syndrome patient PBMC. Thawed PBMC were incubated OVN with or without IL-2 (5 or 100 U/mL) then mixed with Sezary syndrome patient PBMC or Cou-L cells (E/T ratio=10) alone or in the presence of 25 µg/mL of chimeric AZ158 produced in EBX. After 4 h incubation in the presence of anti-CD107, cells were stained with anti-CD3, anti-CD56 and anti-IFN-γ. Percentages of IFN-γ producing NK cells (defined as CD3$^-$CD56$^+$ lymphocytes) are shown. Results are representative of 2 independent experiments, made with 2 different sets of effector PBMC as well as 2 different sets of target patient PBMC. For each effector-target set, and again independently of IL-2 pre-treatment, chAZ158 produced by EBX cells induced a strong increase in IFN-γ producing NK cells compared to NK cells in the absence of chAZ158.

Figure 16:
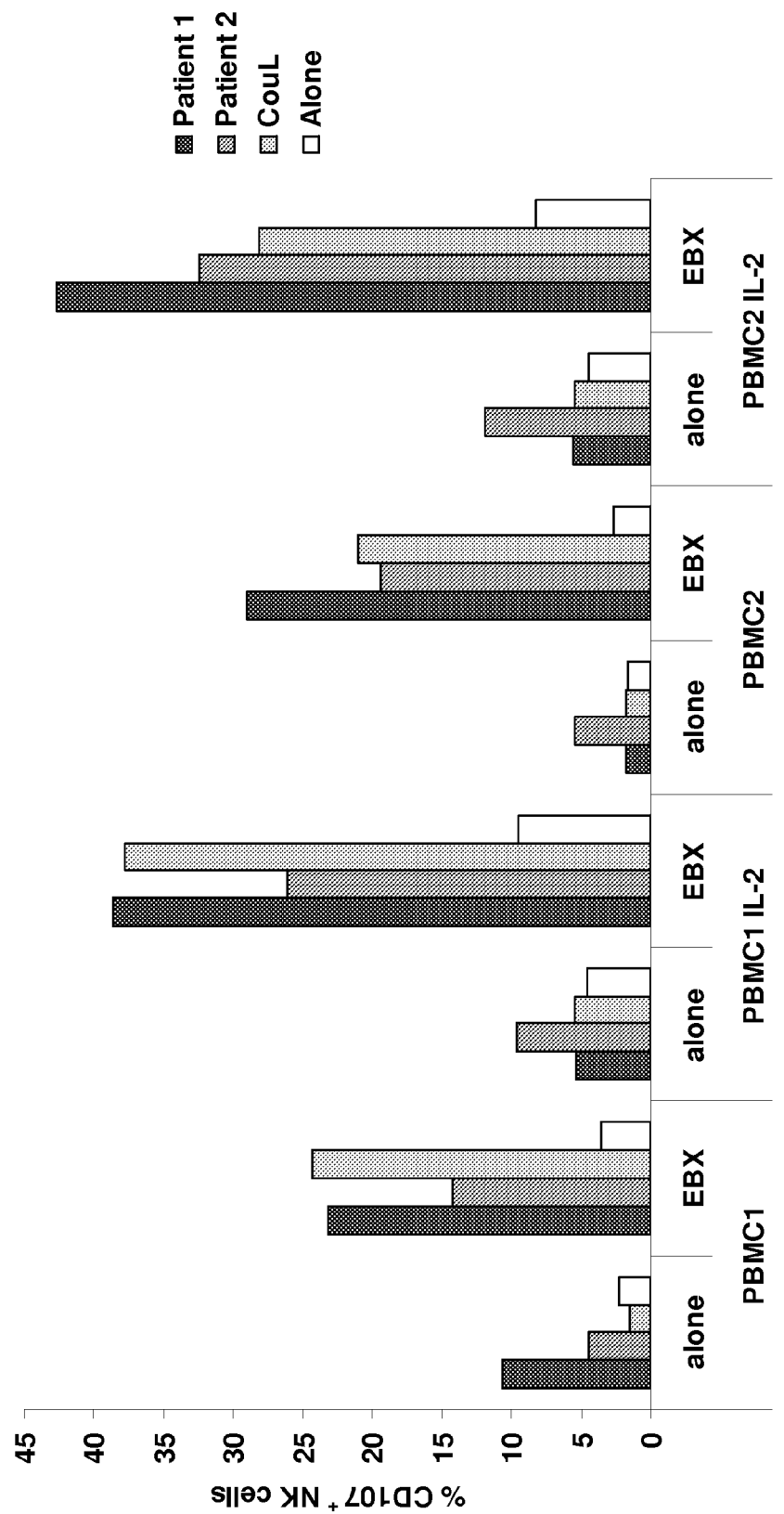
FIG. 16 shows chAZ158-induced CD107 mobilization by heterologous NK cells against Sezary syndrome patient PBMC. ChAZ158 produced by EBX cells induced a strong increase in CD107 positive NK cells compared to NK cells in the absence of chAZ158.

FIG. 16 shows chAZ158-induced CD107 mobilization by heterologous NK cells against Sezary syndrome patient PBMC. Thawed PBMC were incubated OVN with or without IL-2 (5 or 100 U/mL) then mixed with Sezary syndrome patient PBMC or Cou-L cells (E/T ratio=10) alone or in the presence of 25 µg/mL of mentioned mAbs (i.e. Mouse or chimeric AZ158 or Rituxan). After 4 h incubation in the presence of anti-CD107, cells were stained with anti-CD3, anti-CD56 and anti-IFN-γ. Percentages of CD107 positive NK cells (defined as CD3$^-$CD56$^+$ lymphocytes) are shown. Results are representative of 2 independent experiments, made with 2 different sets of effector PBMC as well as 2 different sets of target patient PBMC. For each effector-target set, and again independently of IL-2 pre-treatment, chAZ158 produced by EBX cells induced a strong increase in CD107 positive NK cells compared to NK cells in the absence of chAZ158.

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All publications and patent applications cited in this specification are herein incorporated by reference in their entireties as if each individual publication or patent application were specifically and individually indicated to be incorporated by reference.

This invention includes all modifications and equivalents of the subject matter recited in the aspects or claims presented herein to the maximum extent permitted by applicable law.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of producing an antibody suitable for use as a medicament in the treatment of a disorder characterized by pathogenic killer immunoglobulin-like receptor, three domains, long cytoplasmic tail, 2 (KIR3DL2)-expressing cells, said method comprising: i) producing an antibody that specifically binds to a KIR3DL2 and comprises an Fc region that is an IgG4 isotype or an IgG isotype modified to decrease binding to Fc receptors, ii) contacting the antibody with proliferating KIR3DL2-expressing CD4+ T cells and measuring the ability of the antibody to inhibit proliferation of KIR3DL2-expressing CD4+ T cells, said measuring being carried out in the absence of immune effector cells; and iii) selecting an antibody that inhibits proliferation of KIR3DL2-expressing CD4+ T cells for use as a medicament and/or in the manufacture of a medicament.

2. The method of claim 1, wherein said pathogenic KIR3DL2-expressing cells are KIR3DL2-expressing CD4+ T cells.

3. The method of claim 1, wherein the ability of the antibody to inhibit proliferation of KIR3DL2-expressing CD4+ T cells is measured in the absence of natural killer (NK) cells as the immune effector cells.

4. The method of claim 1, wherein said disorder is an autoimmune or inflammatory disorder.

5. The method of claim 4, wherein said disorder is selected from the group consisting of arthritis, rheumatoid arthritis and spondylarthritis.

6. The method of claim 1, wherein said disorder is a T cell malignancy.

7. The method of claim 1, wherein said antibody comprises an Fc region that is an IgG4 isotype.

8. The method of claim 1, wherein said IgG isotype modified to decrease binding to Fc receptors is a human IgG1 isotype.

9. The method of claim 1, said method further comprising formulating the antibody selected for its ability to inhibit proliferation of KIR3DL2-expressing CD4+ T cells with a pharmaceutically acceptable carrier to form a pharmaceutical composition.

10. The method of claim 1, wherein the antibody does not comprise a radioactive isotope, a toxic polypeptide, or a toxic small molecule.

11. The method of claim 1, wherein the antibody comprises an Fc region that is an IgG isotype modified to decrease binding to Fc receptors.

* * * * *

UNITED STATES PATENT AND TRADEMARK OFFICE
CERTIFICATE OF CORRECTION

PATENT NO. : 9,181,341 B2
APPLICATION NO. : 13/145224
DATED : November 10, 2015
INVENTOR(S) : Nicolas Anfossi et al.

It is certified that error appears in the above-identified patent and that said Letters Patent is hereby corrected as shown below:

IN THE SPECIFICATION

Column 39,
Line 53, "positions×" should read --positions x--.

Column 43,
Line 48, "07/084,926A2 (Biolex Inc.), 08/006,554" should read
--07/084926A2 (Biolex Inc.), 08/006554--.

Column 44,
Line 48, ""ayes"" should read --"aves"--.

Column 54,
Line 47, "PBS1×/BSA" should read --PBS 1X / BSA--.
Line 52, "($^1/_{200}$)." should read --(1/200).--.

Column 57,
Line 13, "1×PBS" should read -- 1x PBS--.
Line 20, "1×PBS." should read -- 1x PBS.--.

Signed and Sealed this
Twenty-ninth Day of March, 2016

Michelle K. Lee
*Director of the United States Patent and Trademark Office*